United States Patent [19]

Okada et al.

[11] Patent Number: 5,334,716
[45] Date of Patent: Aug. 2, 1994

[54] HETEROCYCLIC DERIVATIVES

[75] Inventors: Satoshi Okada; Kozo Sawada; Akio Kuroda, all of Tsukuba; Shinya Watanabe; Hirokazu Tanaka, both of Tsuchiura, all of Japan

[73] Assignee: Fujisawa Pharmaceutical Co., Ltd., Osaka, Japan

[21] Appl. No.: 892,453

[22] Filed: Jun. 2, 1992

[30] Foreign Application Priority Data

Jun. 17, 1991 [GB] United Kingdom ............... 9113027
Sep. 30, 1991 [GB] United Kingdom ............... 9120764
Nov. 15, 1991 [GB] United Kingdom ............... 9124345
Feb. 21, 1992 [GB] United Kingdom ............... 9203809

[51] Int. Cl.$^5$ ............... C07D 417/07; C07D 405/14; A61K 31/41
[52] U.S. Cl. ............................................. 546/112
[58] Field of Search ........................ 546/112; 514/299

[56] References Cited

U.S. PATENT DOCUMENTS 4,205,074  5/1980  Kato ........................... 546/112

FOREIGN PATENT DOCUMENTS 0294035  7/1988  European Pat. Off. .
0458207  11/1991  European Pat. Off. .
1268424  3/1972  United Kingdom .

OTHER PUBLICATIONS

C. Casagrande et al., "Indolizine analogues of indomethacin", Dec. 1971, Farmaco, Edizione Scientifica, vol. 26, No. 12, pp. 1059–1073.

*Primary Examiner*—David B. Springer
*Attorney, Agent, or Firm*—W. Dennis Drehkoff

[57] ABSTRACT

This invention relates to heterocyclic derivatives useful for treating or preventing testosteron 5α-reductase mediated diseases such as alopecia, ache, prostatism and the like, which can be represented by the following formula:

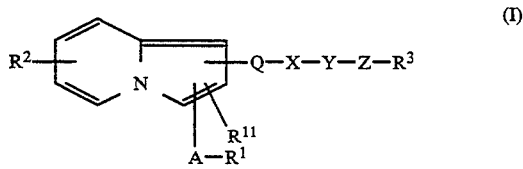

(I)

to a process for their production, to a pharmaceutical composition containing the same and to uses thereof.

12 Claims, No Drawings

HETEROCYCLIC DERIVATIVES

The present invention relates to novel heterocyclic derivatives and a pharmaceutically acceptable salt thereof. More particularly, it relates to novel heterocyclic derivatives and a pharmaceutically acceptable salt thereof which have pharmacological activities such as inhibitory activity on testosteron 5α-reductase and the like, to process for preparation thereof, to a pharmaceutical composition comprising the same and to a use of the same as a medicament.

Accordingly, one object of the present invention is to provide novel heterocyclic derivatives and a pharmaceutically acceptable salt thereof, which are useful as a testosteron 5α-reductase inhibitor.

Another object of the present invention is to provide process for preparation of said heterocyclic derivatives or a salt thereof.

A further object of the present invention is to provide a pharmaceutical composition comprising, as an active ingredient, said heterocyclic derivatives or a pharmaceutically acceptable salt thereof. Still further object of the present invention is to provide a use of said heterocyclic derivatives or a pharmaceutically acceptable salt thereof as a medicament such as testosteron 5α-reductase inhibitor useful for treating or preventing testosteron 5α-reductase mediated diseases such as alopecia, acnes, prostatism, and the like in human being or animals.

The heterocyclic derivatives of the present invention are novel and can be represented by the formula (I):

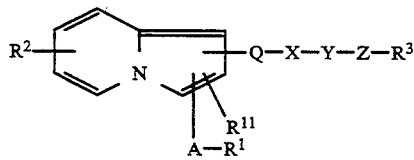

(I)

wherein
R$^1$ is carboxy or protected carboxy,
R$^2$ is hydrogen, lower alkyl or halogen,
R$^3$ is aryl or ar(lower)alkyl, each of which may have suitable substituent(s), [substituted carbamoyl](lower)alkyl, or a group of the formula:

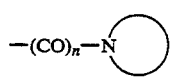

in which

is heterocyclic group containing nitrogen atom, and n is 0 or 1,
R$^{11}$ is hydrogen or lower alkyl,
A is lower alkylene which may be substituted by oxo, or lower alkenylene,
Q is carbonyl or lower alkylene, X is 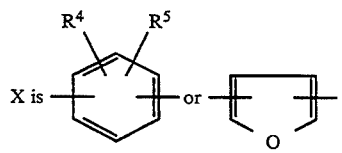

in which
R$^4$ is hydrogen or lower alkyl, and
R$^5$ is hydrogen, lower alkyl or Y—Z—R$^3$,
Y is bond or lower alkylene,
Z is lower alkylene, lower alkenylene,

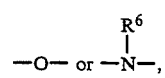

in which R$^6$ is hydrogen, lower alkyl, ar(lower)alkyl which may have suitable substituent(s) or amino protective group.

According to the present invention, the object compound (I) and the salt thereof can be prepared by the following processes.

Process 1

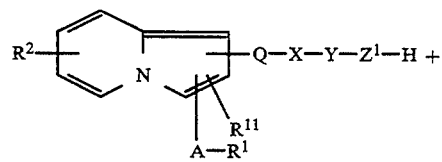

(II)
or a salt thereof

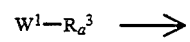

(III)
or a salt thereof

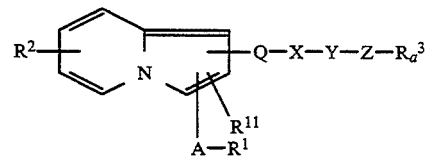

(I-a)
or a salt thereof

Process 2

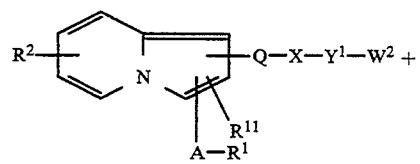

(IV)
or a salt thereof

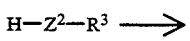

(V)
or a salt thereof

-continued

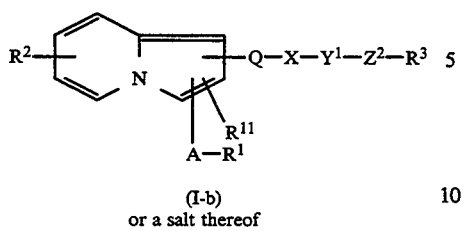

(I-b)
or a salt thereof

Process 3

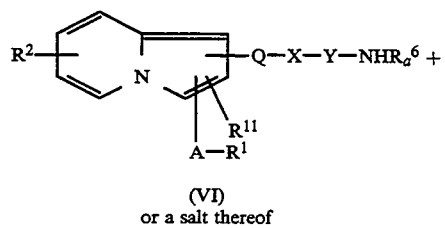

(VI)
or a salt thereof

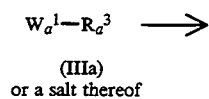

(IIIa)
or a salt thereof

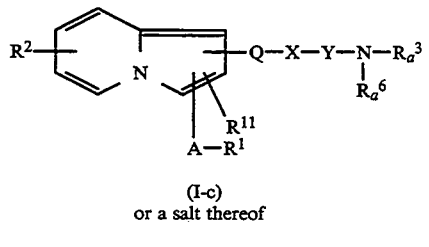

(I-c)
or a salt thereof

Process 4

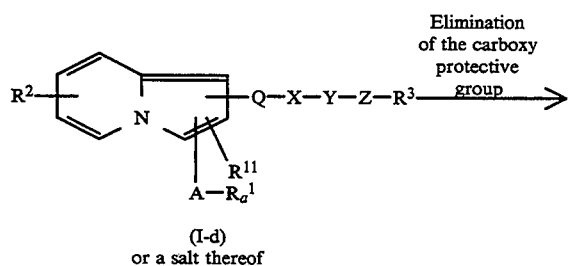

(I-d)
or a salt thereof

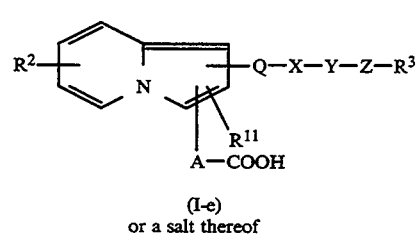

(I-e)
or a salt thereof

Process 5

-continued

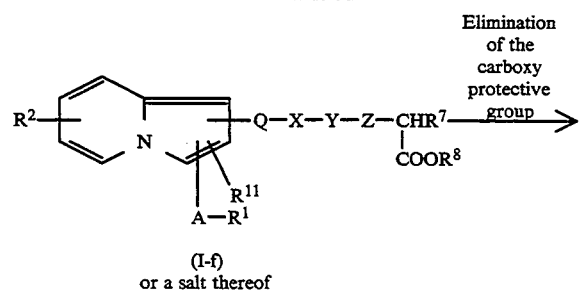

(I-f)
or a salt thereof $$R^2 \text{—} \underset{\underset{A-R^1}{R^{11}}}{\text{ring}} \text{—} Q\text{—}X\text{—}Y\text{—}Z\text{—}\underset{COOH}{CHR^7}$$

(I-g)
or a salt thereof

Process 6

$$R^2 \text{—} \underset{\underset{A-R^1}{R^{11}}}{\text{ring}} \text{—} Q\text{—}X\text{—}Y\text{—}Z\text{—}\underset{COOH}{CHR^7} +$$

(I-g)
or its reactive derivative
at the carboxy group
or a salt thereof $$H\text{—}R^9 \longrightarrow$$

(VII)
or its reactive derivative at the
amino group
or a salt thereof $$R^2 \text{—} \underset{\underset{A-R^1}{R^{11}}}{\text{ring}} \text{—} Q\text{—}X\text{—}Y\text{—}Z\text{—}\underset{COR^9}{CHR^7}$$

(I-h)
or a salt thereof

Process 7

$$R^2 \text{—} \underset{\underset{A-R^1}{R^{11}}}{\text{ring}} \text{—} Q\text{—}X\text{—}Y\text{—}\underset{R_b^6}{N}\text{—}R^3 \xrightarrow{\text{Elimination of the amino protective group}}$$

(I-i)
or a salt thereof

5

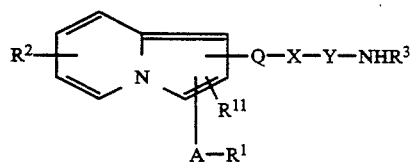

(I-j) or a salt thereof

Process 8

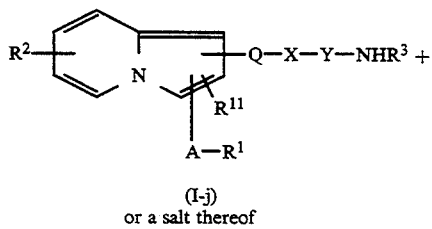

(I-j) or a salt thereof

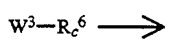

(VIII) or a salt thereof

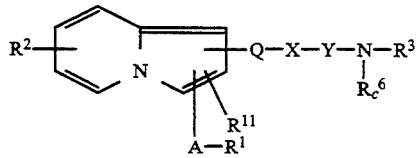

(I-k) or a salt thereof

Process 9

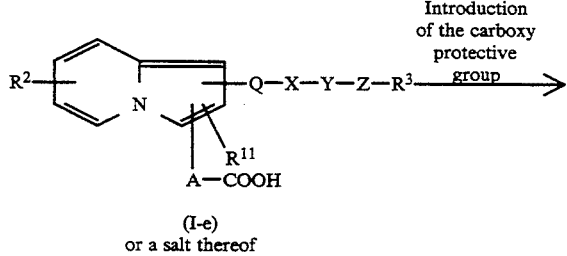

(I-e) or a salt thereof

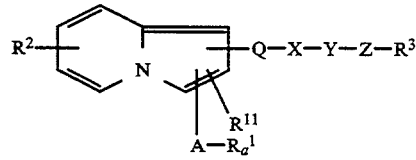

(I-d) or a salt thereof

Process 10

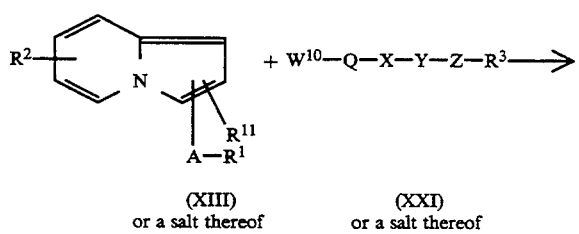

(XIII) or a salt thereof      (XXI) or a salt thereof

6

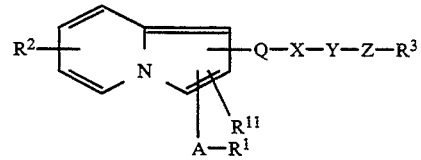

(I) or a salt thereof wherein $R^1$, $R^2$, $R^3$, $R^4$, $R^5$, $R^{11}$, A, Q, X, Y and Z are each as defined above, $R_a^1$ is protected carboxy, $R_a^3$ is ar(lower)alkyl which may have suitable substituent(s), [substituted carbamoyl]-(lower)alkyl, or a group of the formula:

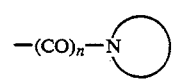

in which

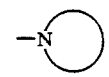

and n are each as defined above, $R_b^6$ is amino protective group, $R_c^6$ is lower alkyl, ar(lower)alkyl which may have suitable substituent(s) or amino protective group, $R^7$ is aryl which may have suitable substituent(s), $R^8$ is carboxy protective group, $R^9$ is amino which may have suitable substituent(s), $W^1$ is a leaving group, $W_a^1$, $W^2$, $W^3$ and $W^{10}$ are each acid residue, $Y^1$ is lower alkylene, $Z^1$ is

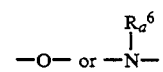

in which $R_a^6$ is hydrogen lower alkyl or amino protective group, and $Z^2$ is

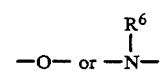

in which $R^6$ is as defined above.

Suitable salts of the compounds (I) are conventional non-toxic, pharmaceutically acceptable salt and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate; benzenesulfonate, p-toluenesulfonate, etc.); a salt with a basic or acidic amino acid (e.g. arginine, aspartic acid, glutamic acid, etc.); and the like, and the preferable example thereof is an acid addition salt.

With respect to the salt of the compounds (I-a) to (I-k), (II), (III), (IIIa), (IV), (V), (VI), (VII), (VIII), (XII) and (XXI), in Processes 1 to 10, the suitable examples of the salts of these compounds are to be referred to those as exemplified for the object compound In the above and subsequent descriptions of the (I).

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" may include straight or branched one, having 1 to 10 carbon atom(s), such as methyl, ethyl, propyl, isopropyl, butyl, isobutyl, t-butyl, pentyl, hexyl, heptyl, octyl, nonyl, decyl, and the like, preferably one having 1 to 6 carbon atoms, and more preferably one having 1 to 4 carbon atoms.

The term "halogen" means fluoro, chloro, bromo and iodo.

Suitable "lower alkylene" means straight or branched bivalent lower alkane such as methylene, ethylene, trimethylene, tetramethylene, pentamethylene, hexamethylene, propylene, and the like, which may be substituted by oxo.

Suitable "leaving group" may include hydroxy, reactive group derived from hydroxy, and the like.

Suitable "reactive group derived from hydroxy" may include acid residue and the like.

Suitable "acid residue" may include halogen e.g. fluoro, chloro, bromo, iodo), acyloxy (e.g. acetoxy, tosyloxy, mesyloxy, etc.) and the like.

Suitable "lower alkenylene" may include one having 2 to 6 carbon atoms such as vinylene, propenylene, and the like.

Suitable "aryl" which may have suitable substituent(s)" may include a conventional group such as aryl (e.g. phenyl, naphthyl, etc.), substituted aryl, for example, lower alkylaryl (e.g. tolyl, xylyl, mesityl, cumenyl, isobutylphenyl, etc.), haloaryl (e.g. chlorophenyl, etc.), and the like.

"Ar(lower)alkyl" in the "ar(lower)alkyl which may have suitable substituent(s)" means straight or branched $C_1$–$C_{10}$ alkyl substituted by aryl group(s), and suitable "ar(lower)alkyl which may have suitable substituent(s)" may include a conventional group such as ar(lower)alkyl (e.g. trityl, benzhydryl, benzyl, phenethyl, naphthylmethyl, 1-phenylethyl, phenylpropyl, phenylbutyl, phenylpentyl, phenylhexyl, phenylheptyl, phenyloctyl, phenyldecyl, 2,2-dimethyl-1-phenylpropyl, etc.), substituted [ar(lower)alkyl], for example, ar(lower)alkyl substituted by one or more substituents such as lower alkyl as mentioned above, halogen as mentioned above, cyano, carboxy, protected carboxy as mentioned below, aryl which may have suitable substituent(s) as mentioned above, amidated carboxy as mentioned below, lower alkoxy (e.g. methoxy, ethoxy, propoxy, etc.), hydroxy(lower)alkyl (e.g. hydroxyisobutyl, etc.), protected hydroxy(lower)alkyl as lower alkanoyloxy(lower)alkyl (e.g. acetoxyisobutyl, etc.), cyclo(lower)alkyl(lower)alkyl (e.g. cyclopropylmethyl), cyclobutylmethyl, etc.), lower alkenyl (e.g. vinyl, propenyl, butenyl, etc.), and lower alkynyl (e.g. ethynyl, propynyl, butynyl, etc.). Specific examples of thus defined "ar(lower)alkyl which may have suitable substituents" may be methylbenzyl, isobutylbenzyl, (methylphenyl)ethyl, (isobutylphenyl)ethyl, (methylphenyl)propyl, (isobutylphenyl)propyl, (isobutylphenyl)butyl, (methylphenyl)pentyl, (isobutylphenyl)pentyl, (isobutylphenyl)hexyl, (isobutylphenyl)heptyl, (isobutylphenyl)octyl, bis(methylphenyl)methyl, bis(propylphenyl)methyl, bis(butylphenyl)methyl, bis(isobutylphenyl)methyl, bis(chlorophenyl)methyl, (cyano)(isobutylphenyl)methyl, (carboxy)(isobutylphenyl)methyl, (benzyloxycarbonyl)(isobutylphenyl)methyl, (N,N-diethylcarbamoyl)(isobutylphenyl)methyl, (t-butylcarbamoyl)(isobutylphenyl)methyl, (phenylcarbamoyl)(isobutylphenyl)methyl, (isobutylphenylcarbamoyl)(isobutylphenyl)methyl, (butylcarbamoyl)(isobutylphenyl)methyl, (heptylcarbamoyl)(isobutylphenyl)methyl, (ethoxy)(isobutylphenyl)ethyl, (isobutylphenyl)trifluorobutyl, (phenyl)(isobutylphenyl)methyl, [(isobutyl)(methoxy)phenyl]pentyl, [(fluoro)(isobutyl)phenyl]pentyl, [(fluoro) (hydroxyisobutyl)phenyl]pentyl, [(fluoro) (acetoxyisobutyl)phenyl]pentyl, cyclopropylmethylphenyl) butenyl, (isobutylphenyl)butynyl, (isobutylphenyl) butenyl, (isobutylphenyl)pentenyl, etc.], and the like.

Suitable "amino protective group" may be a conventional protective group, which is used in the field of organic chemistry, that is, may include acyl such as lower alkanoyl (e.g. formyl, acetyl, propionyl, butyryl, isobutyryl, valeryl, isovaleryl, pivaloyl, hexanoyl, etc.), lower alkoxycarbonyl (e.g. methoxycarbonyl, ethoxycarbonyl, propoxycarbonyl, butoxycarbonyl, t-butoxycarbonyl, etc.), and the like.

Suitable "protected carboxy" may include an esterified carboxy group.

Suitable examples of the ester moiety of an "esterified carboxy" may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.) lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phtahlidylidene(lower) alkyl ester, or (5-lower alkyl-2-oxo-1,3-dioxol-4-yl) (lower)alkyl ester (e.g. (5-methyl-2-oxo-1,3-dioxol- 4-yl)methyl ester, 5-ethyl-2-oxo-1,3- dioxol-4 -yl)methyl ester, 5-propyl-2-oxo-1,3-dioxol-4-yl) ethyl ester, etc.; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Preferable examples of the esterified carboxy as mentioned above may include lower alkoxycarbonyl (e.g. methoxycarbonyl, ethoxycarbonyl, propoxycarbonyl, isopropoxycarbonyl butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.).

Suitable "carboxy protective group" may be the ester moiety of the above defined "protected carboxy" and may include lower alkyl (e.g. methyl, ethyl, etc.), ar(lower)alkyl (e.g. benzyl, etc.), and the like.

Suitable "amino which may have suitable substituent(s)" is conventional one used in a pharmaceutical field and may include amino, mono or di(lower)alkylamino (e.g. methylamino, dimethylamino, ethylamino, diethylamino, butylamino, t-butylamino, heptylamino, etc.), arylamino (e.g. phenylamino, etc.), lower alkylarylamino (e.g. isobutylphenylamino, etc.), and the like.

Suitable "heterocyclic group containing nitrogen atom" may include saturated or unsaturated monocyclic or polycyclic heterocyclic group containing at least one nitrogen atom. Especially preferable heterocyclic group may be 5- or 6- membered aliphatic heteromonocyclic group (e.g. morpholinyl, pyrrolidinyl, imidazolidinyl, piperidyl, piperazinyl, etc.), unsaturated condensed heterocyclic group such as dibenzo[6 or 7-membered unsaturated]heteromonocyclic group (e.g. phenoxazinyl, phenothiazinyl, 10,11-dihydro-5H-dibenzoazepinyl, etc.), and the like. Suitable "amidated carboxy" may carbamoyl which may have suitable substituent(s) and may include carbamoyl, mono or di(-lower)alkylcarbamoyl (e.g. methylcarbamoyl, dimethylcarbamoyl, ethylcarbamoyl diethylcarbamoyl, butylcarbamoyl, t-butylcarbamoyl, heptylcarbamoyl, etc.), lower alkylarylcarbamoyl (e.g. isobutylphenylcarbamoyl, etc.), and the like.

Suitable "[substituted carbamoyl](lower)alkyl" means carbamoyl(lower)alkyl, in which the carbamoyl moiety is substituted by one or two substituent(s), and suitable substituent may include a conventional group such as lower alkyl as mentioned above, aryl which may have suitable substituent(s) as mentioned above. Specific examples of thus defined "[substituted carbamoyl](lower)alkyl" may be butylcarbamoylmethyl, 1-(heptylcarbamoyl)ethyl, isobutylphenylcarbamoylmethyl, 1-(isobutylphenylcarbamoyl)ethyl, and the like.

Particularly, the preferred embodiments of $R^1$, $R^2$, $R^3$, $R^{11}$, A, Q, X, Y and Z are as follows.

$R^1$ is carboxy; esterified carboxy such as lower alkoxycarbonyl, more preferably $C_1$-$C_4$ alkoxycarbonyl (e.g. methoxycarbonyl, ethoxycarbonyl, etc.); or ar(-lower)alkoxycarbonyl, more preferably mono- or di- or triphenyl($C_1$-$C_4$)alkoxycarbonyl (e.g. benzyloxycarbonyl, etc.), $R^2$ is hydrogen; lower alkyl, more preferably $C_1$-$C_4$ alkyl (e.g. methyl, etc.); or halogen (e.g. chloro, etc.), $R^3$ is aryl which may be substituted by lower alkyl, more preferably phenyl substituted by $C_1$-$C_4$ alkyl (e.g. isobutylphenyl, etc.); ar(lower)alkyl which may be substituted by one or more substituents selected from the group consisting of lower alkyl, halogen, cyano, carboxy, protected carboxy, amidated carboxy, lower alkoxy, hydroxy(lower)alkyl, protected hydroxy(lower)alkyl, cyclo(lower)alkyl, lower alkenyl, and lower alkynyl, more preferably mono- or di- or triphenyl(lower)alkyl which may be substituted by one to four groups selected from lower alkyl, halogen, cyano, carboxy, phenyl(lower)alkoxycarbonyl, mono or di(lower)alkylcarbamoyl, phenylcarbamoyl, lower alkylphenylcarbamoyl, lower alkoxy, hydroxy(lower)alkyl, lower alkanoyloxy(lower)alkyl, cyclo(lower)alkyl(lower)alkyl, lower alkenyl, and lower alkynyl, most preferably mono- or di- or triphenyl($C_1$-$C_{10}$)alkyl which may be substituted by one to four groups selected from ($C_1$-$C_{10}$)alkyl, halogen, cyano, carboxy, phenyl($C_1$-$C_4$)alkoxycarbonyl, mono or di($C_1$-$C_{10}$)alkylcarbamoyl, phenylcarbamoyl, ($C_1$-$C_4$)alkylphenylcarbamoyl, ($C_1$-$C_4$)alkoxy, hydroxy($C_1$-$C_4$)alkyl, ($C_1$-$C_4$)alkanoyloxy($C_1$-$C_4$)alkyl, cyclo($C_3$-$C_6$)alkyl($C_1$-$C_4$)alkyl, ($C_2$-$C_4$)alkenyl and ($C_2$-$C_4$)alkynyl, (e.g. benzyl, isobutylbenzyl, (isobutylphenyl)ethyl, (isobutylphenyl)propyl, (isobutylphenyl)butyl, (isobutylphenyl)pentyl, (isobutylphenyl)hexyl, (isobutylphenyl)heptyl, (isobutylphenyl)octyl, bis(isobutylphenyl)methyl, bis(chlorophenyl)methyl, (cyano)(isobutylphenyl)methyl, (carboxy)(isobutylphenyl)methyl, (benzyloxycarbonyl)-(isobutylphenyl)methyl, (N,N-diethylcarbamoyl)-(isobutylphenyl)methyl, (t-butylcarbamoyl)(isobutylphenyl)methyl, (phenylcarbamoyl)(isobutylphenyl)methyl, (isobutylphenylcarbamoyl)(isobutylphenyl)methyl, (butylcarbamoyl)(isobutylphenyl)methyl, (heptylcarbamoyl)(isobutylphenyl)methyl, (ethoxy)-(isobutylphenyl)ethyl, (isobutylphenyl)(trifluoro)butyl, (phenyl)(isobutylphenyl)methyl, [(isobutyl)(methoxy)-phenyl]pentyl, [(fluoro)(isobutyl)phenyl]pentyl, [(fluoro)(hydroxyisobutyl)phenyl]pentyl, [(fluoro)(acetoxyisobutyl)phenyl]pentyl, (cyclopropylmethylphenyl)-butenyl, (isobutylphenyl)butynyl, (isobutylphenyl)butenyl, (isobutylphenyl)pentenyl, etc.); carbamoyl(lower)alkyl, in which the carbamoyl moiety is substituted by one or two substituent(s) selected from the group consisting of lower alkyl and lower alkylphenyl, more preferably ($C_1$-$C_{10}$)alkylcarbamoyl($C_1$-$C_4$)alkyl or ($C_1$-$C_4$)alkylphenylcarbamoyl($C_1$-$C_4$)alkyl (e.g. heptylcarbamoylethyl, isobutylphenylcarbamoylmethyl, isobutylphenylcarbamoylethyl, etc.); 5- or 6- membered aliphatic heteromonocycliccarbonyl (e.g. piperidylcarbonyl, etc.); or unsaturated condensed heterocyclic group (e.g. phenoxazinyl, phenothiazinyl, 10,11-dihydro-5H-dibenzo[b,f]azepinyl, etc.), $R^{11}$ is hydrogen; or lower alkyl, more preferably $C_1$-$C_4$ alkyl (e.g. methyl, etc.), A is lower alkylene which may be substituted by oxo, more preferably $C_1$-$C_4$ alkylene which may be substituted by oxo (e.g. ethylene, trimethylene, oxotrimethylene, etc.); or lower alkenylene, more preferably $C_2$-$C_4$ alkenylene (e.g. propenylene, etc.), Q is carbonyl; or lower alkylene, more preferably $C_1$-$C_4$ alkylene (e.g. methylene, etc.), X is

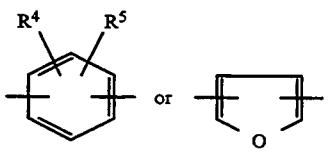

in which

R⁴ is hydrogen; or lower alkyl, more preferably $C_1-C_4$ alkyl (e.g. methyl, etc.), R⁵ is hydrogen; lower alkyl, more preferably $C_1-C_4$ alkyl (e.g. methyl, etc.); or ar(lower)alkylamino which may be substituted by the group(s) selected from lower alkyl or lower alkoxycarbonyl, more preferably $C_1-C_4$ alkylbenzylamino or N-$C_1$-$C_4$alkoxycarbonyl-N-$C_1$-$C_4$alkylbenzylamino (e.g. isobutylbenzylamino, N-t-butoxycarbonyl-N-isobutylbenzylamino, etc.), Y is bond; or lower alkylene, more preferably $C_1-C_4$ alkylene (e.g. methylene, etc.), and Z is lower alkylene, more preferably $C_1-C_4$ alkylene (e.g. methylene, etc.); lower alkenylene, more preferably $C_2-C_4$ alkenylene (e.g. vinylene, etc.);

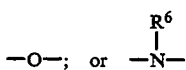

in which

R⁶ is hydrogen; lower alkyl, preferably $C_1-C_4$ alkyl (e.g. methyl, ethyl, etc.); lower alkoxycarbonyl, preferably $C_1-C_4$ alkoxycarbonyl (e.g. t-butoxycarbonyl, etc.); ar(lower)alkyl which may be substituted by lower alkyl, more preferably mono- or di- or triphenyl(lower)alkyl which may be substituted by lower alkyl, most preferably mono- or di- or triphenyl($C_1$-$C_6$)alkyl which may be substituted by $C_1$-$C_4$alkyl (e.g. benzyl, isobutylbenzyl, etc.).

The processes 1 to 10 for preparing the object compound (I) of the present invention are explained in detail in the following.

Process 1

The object compound (I-a) or a salt thereof can be prepared by reacting the compound (II) or a salt thereof with the compound (III) or a salt thereof.

This reaction is usually carried out in a solvent such as alcohol [e.g. methanol, ethanol, etc.], dichloromethane, benzene, N,N-dimethylformamide, tetrahydrofuran, diethyl ether, toluene or any other solvent which does not adversely affect the reaction.

In this reaction, when W¹ in the compound (III) is acid residue, the reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], alkali metal hydride (e.g. sodium hydride, potassium hydride, etc.), tri(lower)alkylamine e.g. trimethylamine, triethylamine, diisopropylethylamine, etc.], pyridine or its derivative e.g. picoline, lutidine, 4-dimethylaminopyridine, etc.], or the like. In case that the base to be used is liquid, it can also be used as a solvent.

When W¹ in the compound (III) is hydroxy, this reaction is usually carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide, N,N'-carbonyl-bis(2-methylimidazole); pentamethylene-ketene-N-cyclohexylimine, diphenyl-ketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; a combination of triarylphosphine [e.g. triphenylphosphine, etc.]or tri(lower)alkylphosphine [e.g. triethylphosphine, etc.], and di(lower)alkyl azodicarboxylate [e.g. diethyl azodicarboxylate, etc.]; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction temperature is not critical, and the reaction can be carried out under cooling, at room temperature or under warming or heating.

Process 2

The object compound (I-b) or a salt thereof can be prepared by reacting the compound (IV) or a salt thereof with the compound (V) or a salt thereof.

This reaction is usually carried out in a solvent such as alcohol [e.g. methanol, ethanol, etc.], dichloromethane, benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], alkali metal hydride (e.g. sodium hydride, potassium hydride, etc.), tri(lower)alkylamine [e.g. trimethylamine, triethylamine, diisopropylethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at room temperature or under warming or heating.

Process 3

The object compound (I-C) or a salt thereof can be prepared by reacting the compound (VI) or a salt thereof with the compound (IIIa) or a salt thereof.

This reaction can be carried out in substantially the same manner as Process 2, and therefore the reaction mode and reaction conditions [e.g. solvents, reaction temperature, etc.]of this reaction are to be referred to those as explained in Process 2.

The present reaction includes, within its scope, the case that when R¹ is carboxy, it is protected during the reaction or at the post-treating step of the present process.

Process 4

The object compound (I-e) or a salt thereof can be prepared by subjecting the compound (I-d) or a salt thereof to elimination reaction of the carboxy protective group.

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4.3.0]non-5-one, 1,4-diazabicyclo[2.2.-2]octane, 1,5-diazabicyclo[5.4.0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitable be selected in accordance with the kind of the carboxy protective group and the elimination method.

The elimination using Lewis acid is preferable to eliminate substituted or unsubstituted ar(lower)alkyl ester and carried out by reacting the compound (Ig) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), water, alcohol [e.g. methanol, ethanol, etc.], dioxane, diethyl ether, carbon disulfide or any other solvent which does not adversely affect the reaction. These solvents may be used as a mixture thereof.

The reduction elimination can be applied preferably for elimination of the protective group such as halo(-lower)alkyl (e.g. 2-iodoethyl, 2,2,2-trichloroethyl, etc.) ester, ar(lower)alkyl (e.g. benzyl, etc.) ester or the like.

The reduction method applicable for the elimination reaction may include, for example, reduction by using a combination of a metal (e.g. zinc, zinc amalgam, etc.) or a salt of chromium compound (e.g. chromous chloride, chromous acetate, etc.) and an organic or an inorganic acid (e.g. acetic acid, propionic acid, hydrochloric acid, etc.); and conventional catalytic reduction in the pressure of a conventional metallic catalyst (e.g. palladium carbon, Raney nickel, etc.).

The reaction temperature is not critical, and the reaction is usually carried out under cooling, at ambient temperature or under warming.

Process 5

The object compound (I-g) or a salt thereof can be prepared by subjecting the compound (I-p) or a salt thereof to elimination reaction of the carboxy protective group.

This reaction can be carried out in substantially the same manner as Process 4, and therefore the reaction mode and reaction conditions [e.g. bases, acids, reducing agents, catalysts, solvents, reaction temperature, etc.] of this reaction are to be referred to those as explained in Process 4.

Process 6

The object compound (I-h) or a salt thereof can be prepared by reacting a compound (I-g) or its reactive derivative at the carboxy group or a salt thereof with a compound (VII) or its reactive derivative at the amino group or a salt thereof.

Suitable reactive derivative at the amino group of the compound (VII) may include Schiff's base type imino or its tautomeric enamine type isomer formed by the reaction of the compound (VII) with a carbonyl compound such as aldehyde, ketone or the like; a silyl derivative formed by the reaction of the compound (VII) with a silyl compound such as bis(trimethylsilyl)acetamide, mono(trimethylsilyl)acetamide, bis(trimethylsilyl)urea or the like; a derivative formed by reaction of the compound (IX) with phosphorus trichloride or phosgene, and the like.

Suitable reactive derivative at the carboxy group of the compound (I-g) may include an acid halide, an acid anhydride, an activated amide, an activated ester, and the like. Suitable examples of the reactive derivatives may be an acid chloride; an acid azide; a mixed acid anhydride within acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (I-g) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (I-g) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower-)alkylmorpholine, N,N-di(lower)alkylbenzylamine, or the like.

The reaction temperature is not critical, and the reaction is usually carried out under cooling to warming.

Process 7

The object compound (I-j) or a salt thereof can be prepared by subjecting the compound (I-i) or a salt thereof to elimination reaction of the amino protective group.

This reaction can be carried out in substantially the same manner as Process 4, and therefore the reaction mode and reaction conditions [e.g. bases, acids, reducing agents, catalysts, solvents, reaction temperature, etc.] of this reaction are to be referred to those as explained in Process 4.

Process 8

The object compound (I-k) or a salt thereof can be prepared by reacting the compound (I-j) or a salt thereof with the compound (VIII) or a salt thereof.

This reaction can be carried out in substantially the same manner as Process 2, and therefore the reaction mode and reaction conditions [e.g. solvents, reaction temperature, etc.] of this reaction are to be referred to those as explained in Process 2.

The present reaction includes, within its scope, the case that when $R^1$ is carboxy, it is protected during the reaction or at the post-treating step of the present process.

Process 9

The object compound (I-d) or a salt thereof can be prepared by subjecting the compound (I-e) or a salt thereof to introduction reaction of the carboxy protective group.

The reaction can be carried out in substantially the same manner as Process 2, and therefore the reaction mode and reaction conditions [e.g. solvents, reaction temperature, etc.] of this reaction are to be referred to those as explained in Process 2.

Process 10

The object compound (I) or a salt thereof can be prepared by reacting the compound (XII) or a salt thereof with the compound (XXI) or a salt thereof.

This reaction can be carried out in substantially the same manner as Process 2, and therefore the reaction mode and reaction conditions [e.g. solvents, reaction temperature, etc.] of this reaction are to be referred to those as explained in Process 2.

The present reaction includes, within its scope, the case that when $R^1$ is protected carboxy, it is eliminated during the reaction or at the post-treating step of the present process.

The starting compounds (II) and (IV) can be prepared by the following methods, the details of which are shown in Preparations mentioned below, or a conventional manner.

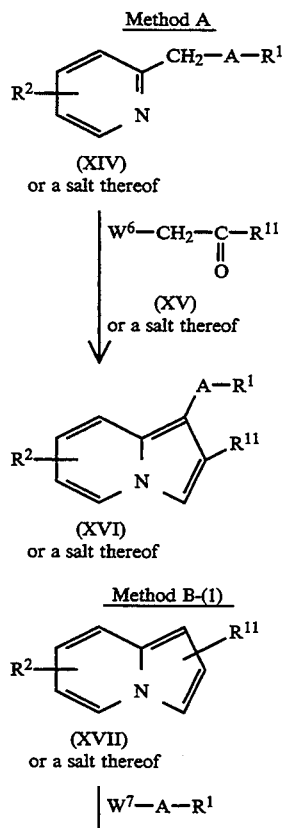

Method A (XIV) or a salt thereof (XV) or a salt thereof (XVI) or a salt thereof

Method B-(1)

(XVII) or a salt thereof (XVIII) or a salt thereof

-continued

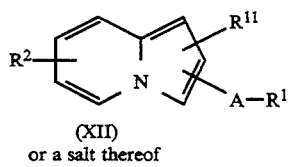

(XII)
or a salt thereof

Method B-(2)

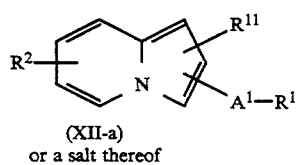

(XII-a)
or a salt thereof

↓ reduction

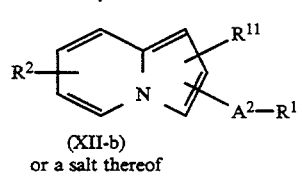

(XII-b)
or a salt thereof

Method C-(1)

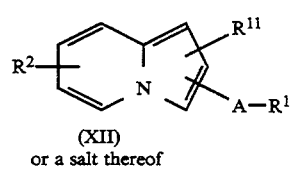

(XII)
or a salt thereof

↓ $W^8$—Q—X—Y—NO$_2$
(XIX)
or a salt thereof

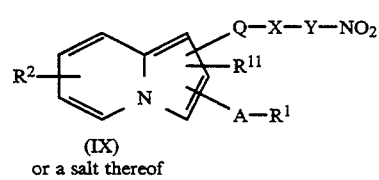

(IX)
or a salt thereof

Method C-(2)

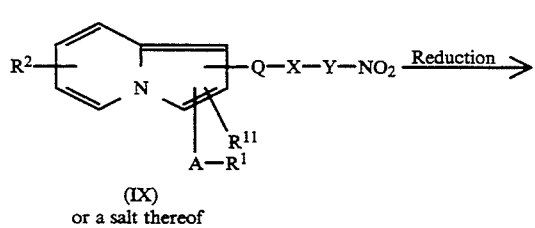 Reduction →

(IX)
or a salt thereof

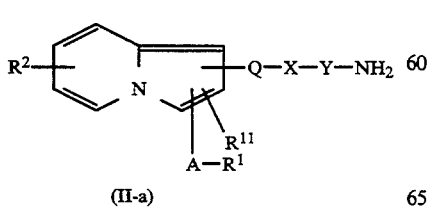

(II-a)
or a salt thereof

Method C-(3)

-continued

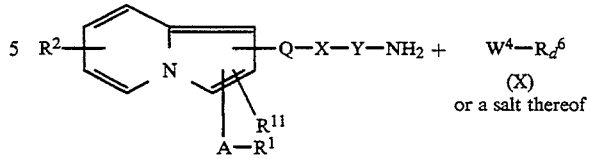

(II-a)
or a salt thereof

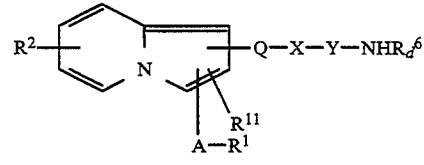

(II-b)
or a salt thererof

Method C-(4)

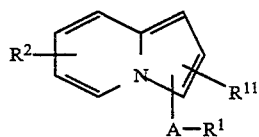

(XII)
or a salt thereof

↓ $W^9$—Q—X—Y—$R^{10}$
(XX)
or a salt thereof

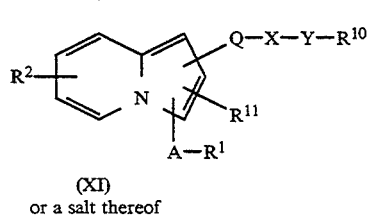

(XI)
or a salt thereof

Method C-(5)

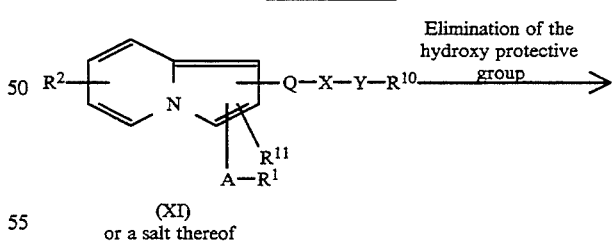 Elimination of the hydroxy protective group →

(XI)
or a salt thereof

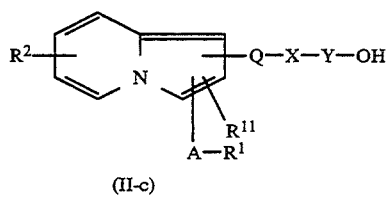

(II-c)
or a salt thereof

Method C-(6)

-continued

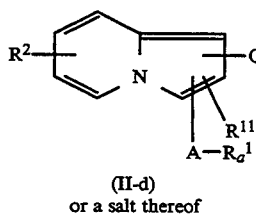

(II-d)
or a salt thereof

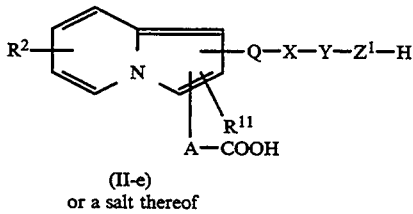

(II-e)
or a salt thereof

Method D

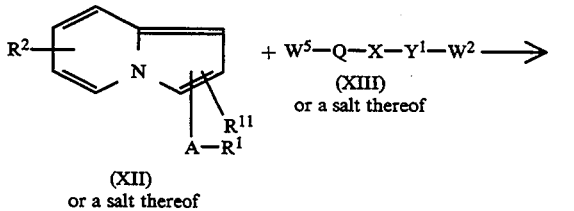

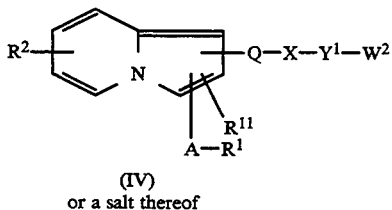

(IV)
or a salt thereof wherein $R^1$, $R_a^1$, $R^2$, $R_d^6$, $R^{11}$, A, Q, X, Y, $Y^1$, $Z^1$, and $W^2$ are each as defined above, $R_d^6$ is lower alkyl or amino protective group, $R^{10}$ is protected hydroxy, $W^4$, $W^5$, $W^6$, $W^7$, $W^8$ and $W^9$ are each acid residue, $A^1$ is lower alkylene having oxo, and $A^2$ is lower alkylene.

Methods A~D can be carried out in a conventional manner.

The object compound (I) of the present invention can be isolated and purified in a conventional manner, for example, extraction, precipitation, fractional crystallization, recrystallization, chromatography, and the like.

The object compound (I) thus obtained can be converted to its salt by a conventional method.

The object compound (I) of the present invention is useful as a testosteron 5α-reductase inhibitor and effective to testosteron 5α-reductase mediated diseases such as prostatism, prostatic hypertrophy, prostatic cancer, alopecia, hirsutism (e.g. female hirsutism, etc.), androgenic alopecia (or male-pattern baldness), acne (e.g. acne vulgaris, pimple etc.), other hyperandrogenism, and the like.

In order to illustrate the usefulness of the object compounds (I), pharmacological activity of representative compounds of the present invention is shown below.

[1] Test Compound (1) 4-[3-[3-[Bis(4-isobutylphenyl)methylamino]benzoyl-]indolizin-1-yl]butyric acid
(2) 4-[1-[4-[Bis(4-isobutylphenyl)methylamino]benzoyl-]indolizin-3-yl]butyric acid
(3) 4-[3-[3-[Bis(4-isobutylphenyl)methoxy]benzoyl]indolizin-1-yl]butyric acid
(4) 4-[1-[4-[1-(4-Isobutylphenyl)propyloxy]benzoyl]indolizin-3-yl]butyric acid
(b 5) 4-[1-[4-[1-(4-Isobutylphenyl)pentyloxy]benzoyl]indolizin-3-yl]butyric acid

[2] Inhibitory activity on testosterone 5α-reductase in rats

Test Methods i) Materials 1,2,6,7-$^3$H-Testosterone (85-105 Ci/mmol):

1,2,6,7-$^3$H-Testosterone (85-105 Ci/mmol) is a mixture of 1,2,6,7-$^3$H-testosterone and testosterone which includes 85-105 Ci of 1,2,6,7-$^3$H-testosterone per mmol of testosterone and is purchased from New England Nuclear, Boston, Mass., U.S.A.

Aquazol-2 (Aquazol-2 Universal LSC Cocktail): trademark, purchased from New England Nuclear, Boston, Mass., U.S.A.

ii) Preparation of prostatic testosterone 5α-reductase

Mature Spraque-Dawley male rats (7-8 weeks old) were sacrificed by diethyl ether. The ventral prostates were dissected to be free of their capsules and their combined volume was measured by displacement in several milliliters of ice-cold medium A (0.32M sucrose, 0.1 mM dithiothreitol and 20 mM sodium phosphate, pH 6.5). Unless specified, all the following procedures were carried out at 0°-4° C. The prostates were drained, minced, and then homogenized in 3-4 tissue volumes of medium A with Pyrex-glass homogenizer. The homogenate was fractioned by differential centrifugations at 3,000 g for minutes. The resulting pellets were resuspended in medium A. The suspension (20-30 mg protein/ml) was stored at −80° C.

iii) Testosterone 5α-reductase assay

The reaction solution contains 1 mM dithiothreitol, 40 mM sodium phosphate pH 6.5, 50 μM NADPH, 1,2,6,7-$^3$H-testosterone/testosterone (2.2×10$^{-9}$ M) and the suspension prepared above (0.8 mg of protein) in a total volume of 565 μl. Test Compound was added in 10 μl of 10% ethanol whereas control tubes received the same volume of 10% ethanol. The reaction was started with the addition of the enzyme suspension. After incubation at 37° C. for 30 minutes, the reaction was extracted with 1 ml of ethyl acetate. Fifty μl of ethyl acetate phase was chromatographed on a Merck silica plastic sheet Kieselgel 60 F$_{254}$, using ethyl acetate: cyclohexane (1:1) as the developing solvent system. The plastic sheet was air dried and cut the testosterone and the 5α-dihydrotestosterone areas. The radioactivity was counted in 5 ml of Aquazol-2 in Packard scintillation counter (PACKARD TRI - CARB 4530), and an inhibitory ratio was calculated.

| [3] Test Results: | |
|---|---|
| Compound | IC$_{50}$ (M) |
| (1) | 2.3 × 10$^{-9}$ |
| (2) | 4.4 × 10$^{-10}$ |
| (3) | 6.7 × 10$^{-9}$ |
| (4) | 5.5 × 10$^{-10}$ |

| -continued | |
|---|---|
| [3] Test Results: | |
| Compound | IC$_{50}$ (M) |
| (5) | 1.8 × 10$^{-9}$ |

For therapeutic or preventive administration, the object compound (I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparation may be in solid form such as tablet, granule, powder, capsule, or liquid form such as solution, suspension, syrup, emulsion, lemonade, lotion and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases or conditions, a kind of the compound (I) to be applied, etc. In general amounts between 0.01 mg and about 500 mg or even more per day may be administered to a patient. An average single dose of about 0.05 mg, 0.1 mg, 0.25 mg, 0.5 mg, 1 mg, 20 mg, 50 mg, 100 mg of the object compound (I) of the present invention may be used in treating diseases.

The following Preparations and Example are given for the purpose of illustrating the present invention.

Preparation 1

To a solution of ethyl 3-chloroformylpropionate (1.65 g) and aluminum chloride (1.78 g) in methylene chloride (20 ml) was added indolizine (977 mg) in methylene chloride (5 ml) at ambient temperature. After stirring for 1 hour, ice was added and extracted with chloroform. The organic layers were washed with saturated sodium bicarbonate and brine, and dried over sodium sulfate. After evaporation of the solvent, the residue was chromatographed on silica gel eluting with hexane-ethyl acetate (3:2) to give the following compounds.

Ethyl 4-(3-indolizinyl)-4-oxobutyrate (0.74 g)
NMR (CDCl$_3$, δ): 1.28 (3H, t, J=7 Hz), 2.79 (2H, t, J=7 Hz), 3.29 (2H, t, J=7 Hz), 4.18 (2H, q, J=7 Hz), 6.51 (1H, d, J=5 Hz), 6.84 (1H, dt, J=1 Hz, 6 Hz), 7.12 (1H, m), 7.52 (1H, m), 7.58 (1H, d, J=5 Hz), 9.83 (1H, dd, J=1 Hz, 6 Hz)

Ethyl 4-(1-indolizinyl)-4-oxobutyrate (0.26 g)
NMR (CDCl$_3$, δ): 1.28 (3H, t, J=7 Hz), 2.78 (2H, t, J=7 Hz), 3.25 (2H, t, J=7 Hz), 4.17 (2H, q, J=7 Hz), 6.77 (1H, dt, J=1 Hz, 7 Hz), 7.12 (1H, m), 7.22 (2H, m), 8.03 (1H, dt, J=7 Hz, 1 Hz), 8.44 (1H, dt, J=9 Hz, 1 Hz)

Preparation 2

To a solution of ethyl 4-(3-indolizinyl)-4-oxobutyrate (556 mg) in tetrahydrofuran (5 ml) was added borane in tetrahydrofuran (1M solution, 3.6 ml) at 0° C. After stirring at room temperature for 10 minutes, the reaction was quenched by aqueous potassium dihydrogen phosphate at 0° C., and the resulting mixture was extracted with ether. The organic layers were washed with water, aqueous sodium bicarbonate and brine, dried over sodium sulfate. After evaporation of the solvent, the residue was chromatographed on alumina (Hexane-methylene chloride=1:1) to give ethyl 4-(3-indolizinyl)butyrate (294 mg).

NMR (CDCl$_3$, δ): 1.26 (3H, t, J=7 Hz), 2.08 (2H, m), 2.43 (2H, t, J=7 Hz), 2.89 (2H, t, J=7 Hz), 4.14 (2H, q, J=7 Hz), 6.3–6.7 (4H, m), 7.37 (1H, dt, J=9 Hz, 1 Hz), 7.78 (1H, dt, J=6 Hz, 1 Hz)

Preparation 3

The following compound was obtained according to a similar manner to that of Preparation 2.

Ethyl 4-(1-indolizinyl)butyrate
NMR (CDCl$_3$, δ): 1.23 (3H, t, J=7 Hz), 1.98 (2H, m), 2.34 (2H, t, J=7 Hz), 2.79 (2H, t, J=7 Hz), 4.12 (2H, q, J=7 Hz), 6.37 (1H, dt, J=1 Hz, 7 Hz), 6.56 (1H, m), 6.62 (1H, d, J=3 Hz), 7.21 (1H, d, J=3 Hz), 7.29 (1H, d, J=9 Hz), 7.84 (1H, d, J=7 Hz)

Preparation 4

To a solution of 3-nitrobenzoyl chloride (314 mg) in methylene chloride (20 ml) was added aluminum chloride (305 mg) at room temperature. After stirring for 10 minutes, a solution of ethyl 4-(3-indolizinyl)butyrate (297 mg) in methylene chloride (3 ml) was added thereto. After 1 hour, ice was added and the resulting mixture was extracted with chloroform. The organic layers were washed with water, aqueous sodium bicarbonate and brine, dried over sodium sulfate. After evaporation of the solvent, the residue was chromatographed on silica gel (hexane:ethyl acetate=2:3) to give ethyl 4-[1-(3-nitrobenzoyl)indolizin-3-yl]butyrate (353 mg).

NMR (CDCl$_3$, δ): 1.23 (3H, t, J=7 Hz), 2.08 (2H, m), 2.46 (2H, t, J=7 Hz), 2.93 (2H, t, J=7 Hz), 4.13 (2H, q, J=7 Hz), 6.80 (1H, s), 6.98 (1H, dt, J=1 Hz, 7 Hz), 7.30 (1H, m), 7.69 (1H, t, J=8 Hz), 8.10 (1H, d, J=7 Hz), 8.16 (1H, m), 8.39 (1H, m), 8.53 (1H, dt, J=9 Hz, 1 Hz), 8.57 (1H, m)

Preparation 5

The following compounds were obtained according to a similar manner to that of Preparation 4.

(1) Ethyl 4-[1-(4-nitrobenzoyl)indolizin-3-yl]butyrate
NMR (CDCl$_3$, δ): 1.25 (3H, t, J=7 Hz), 2.04 (2H, m), 2.46 (2H, t, J=7 Hz), 2.90 (2H, t, J=7 Hz), 4.13 (2H, q, J=7 Hz), 6.76 (1H, s), 6.99 (1H, dt, J=1 Hz, 7 Hz), 7.32 (1H, m), 7.95 (2H, d, J=9 Hz), 8.10 (1H, d, J=7 Hz), 8.35 (2H, d, J=9 Hz), 8.54 (1H, d, J=8 Hz)

(2) Ethyl 4-[3-(3-nitrobenzoyl)indolizin-1-yl]butyrate
NMR (CDCl$_3$, δ): 1.23 (3H, t, J=7 Hz), 2.01 (2H, m), 2.37 (2H, t, J=7 Hz), 2.81 (2H, t, J=7 Hz), 4.12 (2H, q, J=7 Hz), 7.02 (1H, dt, J=1 Hz, 7 Hz), 7.11 (1H, s), 7.28 (1H, dt, J=1 Hz, 8 Hz), 7.62 (1H, dt, J=8 Hz, 1 Hz), 7.69 (1H, t, J=7 Hz), 8.12 (1H, m), 8.38 (1H, m), 8.63 (1H, m), 9.98 (1H, d, J=7 Hz)

(3) Ethyl 4-[3-(4-nitrobenzoyl)indolizin-1-yl]butyrate
NMR (CDCl$_3$, δ): 1.23 (3H, t, J=7 Hz), 2.00 (2H, m), 2.36 (2H, t, J=7 Hz), 2.79 (2H, t, J=7 Hz), 4.12 (2H, q, J=7 Hz), 7.02 (1H, dt, J=1 Hz, 7 Hz), 7.07 (1H, s), 7.28 (1H, m), 7.61 (1H, dt, J=9 Hz, 1 Hz), 7.93 (2H, d, J=9 Hz), 8.36 (2H, d, J=9 Hz), 9.98 (1H, d, J=7 Hz)

(4) Ethyl 4-[1-(4-methoxybenzoyl)indolizin-3-yl]butyrate
NMR (CDCl$_3$, δ): 1.25 (3H, t, J=7 Hz), 1.98–2.17 (2H, m), 2.45 (2H, t, J=7 Hz), 2.90 (2H, t, J=7 Hz), 3.89

(3H, s), 4.14 (2H, q, J=7 Hz), 6.84–7.04 (4H, m), 7.12–7.22 (1H, m), 7.80–7.90 (2H, m), 8.01 (1H, d, J=7 Hz), 8.48 (1H, d, J=9 Hz)

(5) Ethyl 4-[1-(3-methoxybenzoyl) indolizin-3-yl]butyrate

NMR (CDCl$_3$, δ): 1.26 (3H, t, J=7 Hz), 1.97–2.15 (2H, m), 2.44 (2H, t, J=7 Hz), 2.89 (2H, t, J=7 Hz), 3.88 (3H, s), 4.13 (2H, q, J=7 Hz), 6.87–6.97 (2H, m), 7.03–7.12 (1H, m), 7.16–7.26 (1H, m), 7.32–7.43 (3H, m), 8.03 (1H, d, J=7 Hz), 8.51 (1H, d, J=9 Hz)

(6) Ethyl 4-[3-(4-methoxybenzoyl)indolizin-1-yl]butyrate

NMR (CDCl$_3$, δ) : 1.23 (3H, t, J=7 Hz), 1.92–2.10 (2H, m), 2.35 (2H, t, J=7 Hz), 2.79 (2H, t, J=7 Hz), 3.90 (3H, s), 4.12 (2H, q, J=7 Hz), 6.85–7.23 (5H, m), 7.54 (1H, d, J=9 Hz), 7.77–7.88 (2H, m)

(7) Ethyl 4-[3-(3-methoxybenzoyl) indolizin-1-yl]butyrate

NMR (CDCl$_3$, δ) : 1.24 (3H, t, J=7 Hz), 1.90–2.08 (2H, m), 2.36 (2H, t, J=7 Hz), 2.78 (2H, t, J=7 Hz), 3.88 (3H, s), 4.12 (2H, q, J=7 Hz), 6.87–7.07 (3H, m), 7.13–7.40 (5H, m), 7.44 (1H, d, J=9 Hz)

Preparation 6

To a solution of ethyl 4-[1-(3-nitrobenzoyl)-indolizin-3-yl]butyrate (350 mg) in dioxane-ethanol (1:1; ml) was added 10% palladium on carbon (210 mg) and hydrogenated under 4 atm of hydrogen for 4 hours, and then filtered through a celite. Removal of the solvent gave ethyl 4-[1-(3-aminobenzoyl)indolizin-3-yl]butyrate (325 mg).

NMR (CDCl$_3$, δ): 1.23 (3H, t, J=7 Hz), 2.05 (2H, m), 2.43 (2H, t, J=7 Hz), 2.88 (2H, t, J=7 Hz), 4.12 (2H, q, J=7 Hz), 6.90 (1H, m), 6.91 (1H, s), 7.1–7.4 (5H, m), 8.01 (1H, d, J=7 Hz), 8.48 (1H, dt, J=8 Hz, 1 Hz)

Preparation 7

The following compounds were obtained according to a similar manner to that of Preparation 6.

(1) Ethyl 4-[1-(4-aminobenzoyl)indolizin-3-yl]butyrate

NMR (CDCl$_3$, δ): 1.25 (3H, t, J=7 Hz), 2.07 (2H, m), 2.44 (2H, t, J=7 Hz), 2.89 (2H, t, J=7 Hz), 4.14 (2H, q, J=7 Hz), 6.78 (2H, d, J=9 Hz), 6.86 (1H, dt, J=1 Hz, 7 Hz), 6.92 (1H, s), 7.12 (1H, m), 7.76 (2H, d, J=9 Hz), 7.99 (1H, d, J=7 Hz), 8.43 (1H, d, J=8 Hz)

(2) Ethyl 4-[3-(3-aminobenzoyl)indolizin-1-yl]butyrate

NMR (CDCl$_3$, δ): 1.23 (3H, t, J=7 Hz), 1.98 (2H, m), 2.33 (2H, t, J=7 Hz), 2.78 (2H, t, J=7 Hz), 6.8–7.0 (2H, m), 7.1–7.3 (6H, m), 7.54 (1H, dr, J=8 Hz, 1 Hz), 9.94 (1H, d, J=7 Hz)

(3) Ethyl 4-[3-(4-aminobenzoyl) indolizin-1-yl]butyrate

NMR (CDCl$_3$, δ): 1.24 (3H, t, J=7 Hz), 2.00 (2H, m), 2.35 (2H, t, J=7 Hz), 2.80 (2H, t, J=7 Hz), 4.11 (2H, q, J=7 Hz), 6.73 (2H, d, J=9 Hz), 6.87 (1H, dt, J=1 Hz, 7 Hz), 7.02 (1H, m), 7.20 (1H, s), 7.51 (1H, dt, J=9 Hz, 1 Hz), 7.72 (1H, d, J=9 Hz), 9.86 (1H, d, J=7 Hz)

Preparation 8

To a mixture of ethyl 4-[1-(4-methoxybenzoyl)-indolizin-3-yl]butyrate (640 mg) and ethanethiol (2.5 ml) in dichloromethane (8 ml) was added aluminum chloride (700 mg) at 0° C. After stirred at 0° C. for 10 minutes, the solvent was evaporated and the residue was poured into a mixture of ethyl acetate and ice-water. The organic layer was separated, washed with aqueous sodium bicarbonate and brine, dried over magnesium sulfate and evaporated. The residue was chromatographed on silica gel column eluting with a mixture of chloroform and ethyl acetate (4:1) to give ethyl 4-[1-(4-hydroxybenzoyl)indolizin-3-yl]butyrate (344 mg) as yellow solid.

NMR (DMSO-d$_6$, δ): 1.14 (3H, t, J=7 Hz), 1.85–2.03 (2H, m), 2.41 (2H, t, J=7 Hz), 2.93 (2H, t, J=7 Hz), 4.01 (2H, q, J=7 Hz), 6.84–7.06 (4H, m), 7.19–7.30 (1H, m), 7.67 (2H, d, J=8 Hz), 8.25–8.40 (2H, m)

Preparation 9

The following compounds were obtained according to a similar manner to that of Preparation 8.

(1) Ethyl 4-[1-(3-hydroxybenzoyl) indolizin-3-yl]butyrate

NMR (CDCl$_3$, δ) : 1.25 (3H, t, J=7 Hz), 1.97–2.15 (2H, m), 2.43 (2H, t, J=7 Hz), 2.88 (2H, t, J=7 Hz), 4.13 (2H, q, J=7 Hz), 6.86–6.97 (2H, m), 6.99–7.09 (1H, m), 7.16–7.37 (3H, m), 7.48 (1H, s), 8.01 (1H, d, J=7 Hz), 8.50 (2H, m, J=9 Hz)

(2) Ethyl 4-[3-(4-hydroxybenzoyl) indolizin-1-yl]butyrate

NMR (CDCl$_3$, δ): 1.24 (3H, t, J=7 Hz), 1.92–2.10 (2H, m), 2.38 (2H, t, J=7 Hz), 2.79 (2H, t, J=7 Hz), 4.13 (2H, q, J=7 Hz), 6.86–6.98 (3H, m), 7.12–7.25 (2H, m), 7.55 (1H, d, J=9 Hz), 7.67–7.78 (2H, m)

(3) Ethyl 4-[3-(3-hydroxybenzoyl) indolizin-1-yl]butyrate

NMR (CDCl$_3$, δ): 1.23 (3H, t, J=7 Hz), 1.90–2.08 (2H, m), 2.34 (2H, t, J=7 Hz), 2.76 (2H, t, J=7 Hz), 4.12 (2H, q, J=7 Hz), 6.87–7.07 (3H, m), 7.13–7.40 (5H, m), 7.55 (1H, d, J=9 Hz)

Preparation 10

To a suspension of aluminum chloride (6.67 g) in dichloromethane (70 ml) was added hexanoyl chloride (7.0 ml) at 0° C. After the mixture was stirred at 0° C. for 15 minutes, isobutylbenzene (7.9 ml) was added to the mixture. The mixture was stirred at 0° C. for 30 minutes and poured into ice water. The organic layer was washed with water, aqueous sodium bicarbonate and brine. The solution was dried over magnesium sulfate and evaporated to give 4'-isobutylhexanophenone (10.52 g) as a colorless oil.

NMR (CDCl$_3$, δ): 0.84–0.98 (9H, m), 1.30–1.43 (4H, m), 1.60–2.01 (3H, m), 2.53 (2H, d, J=8.5 Hz), 2.94 (2H, t, J=7 Hz), 7.22 (2H, d, J=8.5 Hz), 7.88 (2H, d, J=8.5 Hz)

Preparation 11

To a solution of 4'-isobutylhexanophenone (10.5 g) in 2-propanol (60 ml) was added sodium borohydride (2.05 g), and the mixture was stirred at 50° C. for 6 hours. The mixture was poured into ice water and acidified with 6N hydrochloric acid. The aqueous solution was extracted with ethyl acetate and the organic layer was washed with water and brine, dried over magnesium sulfate and evaporated to give 1-(4-isobutylphenyl)hexan-1-ol (9.32 g) as a colorless oil.

NMR (CDCl$_3$, δ): 0.83–0.96 (9H, m), 1.16–1.40 (6H, m), 1.60–1.96 (3H, m), 2.48 (2H, d, J=7 Hz), 4.64 (1H, t, J=7 Hz), 7.11 (2H, d, J=S.5 Hz), 7.25 (2H, d, J=8.5 Hz)

Preparation 12

To a solution of 1-(4-isobutylphenyl)hexan-1-ol (9.15 g) and carbon tetrabromide (25.9 g) in tetrahydrofuran (250 ml) was added triphenylphosphine (20.5 g). The mixture was stirred at room temperature for 6 hours. After the white solid was filtered off, the filtrate was evaporated. n-Hexane (300 ml) was added to the residue and the precipitate was filtered off. The filtrate was evaporated and the residual oil was distilled under reduced pressure to give 1-(1-bromohexyl)-4-isobutylbenzene (3.52 g) as a colorless oil.

NMR (CDCl$_3$, δ): 0.82–0.97 (9H, m), 1.20–1.60 (8H, m), 1.74–1.97 (1H, m), 2.00–2.38 (2H, m), 2.46 (2H, d, J=7 Hz), 4.96 (1H, t, J=7.5 Hz), 7.10 (2H, d, J=8.5 Hz), 7.29 (2H, d, J=8.5 Hz)

Preparation 13

A stirred suspension of sodium hydride (3.04 g; 60% in mineral oil) in dimethyl sulfoxide (100 ml) was heated at 80° C. for 40 minutes. Then the solution was cooled. To the solution was added (3-carboxypropyl)triphenylphosphonium chloride (15.9 g) portionwise at ambient temperature. After 30 minutes, 2-pyridinecarbaldehyde (3.96 g) was added at ambient temperature and then the mixture was stirred for 2 hours. Water was added to the mixture and acidified to pH 5 with 1N hydrochloric acid. The mixture was extracted with ethyl acetate and combined organic layer was washed with brine, dried, and concentrated. The residue was chromatographed on silica gel ethyl acetate:methanol=10:1) to give (4E)-5-(2-pyridyl)-4-pentenoic acid (1.6 g).

NMR (CDCl$_3$, δ): 2.5–2.8 (4H, m), 6.6–6.9 (2H, m), 7.19 (1H, m), 7.37 (1H, d, J=8 Hz), 7.70 (1H, dr, J=1 Hz, 8 Hz), 8.59 (1H, d, J=5 Hz)

Preparation 14

To a solution of (4E)-5-(2-pyridyl)-4-pentenoic acid (1.6 g) in ethanol (50 ml) was added d-camphor-10-sulfonic acid (2.3 g), and the mixture was heated under reflux with a reflux condenser containing 3 Å molecular sieves. After 2 hours, the mixture was evaporated, diluted with saturated aqueous sodium bicarbonate and then extracted with ethyl acetate. The organic layers were washed with brine, dried over sodium sulfate and evaporated in vacuo to give ethyl (4E)-5-(2-pyridyl)-4-pentenoate (1.84 g).

NMR (CDCl$_3$, δ): 1.26 (3H, t, J=7 Hz), 2.45–2.7 (4H, m), 4.16 (2H, q, J=7 Hz), 6.53 (1H, d, J=16 Hz), 6.75 (1H, dt, J=16 Hz, 7 Hz), 7.11 (1H, m), 7.25 (1H, d, J=8 Hz), 7.63 (1H, dt, J=1 Hz, 8 Hz), 8.55 (1H, d, J=4 Hz)

Preparation 15

To a solution of ethyl (4E)-5-(2-pyridyl)-4-pentenoate (1.84 g) in ethanol (15 ml) was added 10% palladium on carbon (145 mg), and the mixture was stirred for 3 hours under an atmosphere of hydrogen (4 atm), and then filtered through a celite pad. Removal of the solvent in vacuo gave ethyl 5-(2-pyridyl)pentanoate (1.84 g).

NMR (CDCl$_3$, δ): 1.23 (3H, t, J=7 Hz), 1.6–1.9 (4H, m), 2.34 (2H, t, J=7 Hz), 2.82 (2H, t, J=7 Hz), 4.12 (2H, q, J=7 Hz), 7.05– 7.2 (2H, m), 7.62 (1H, dt, J=1 Hz, 8 Hz), 8.52 (1H, d, J=4 Hz)

Preparation 16

To a solution of ethyl 5-(2-pyridyl)pentanoate (1.07 g) in acetone (5 ml) was added bromoacetone (0.51 ml) and the mixture was refluxed for 2 hours. After removal of the solvent, the residue was dissolved in aqueous sodium bicarbonate (1 g sodium bicarbonate/20 ml water) and then refluxed for 30 minutes. The mixture was extracted with ethyl acetate. The combined organic layers were washed with brine, dried over sodium sulfate, evaporated in vacuo, and chromatographed on silica gel (dichloromethane) to give ethyl 4-(2-methylindolizin-1-yl)butyrate (778 mg).

NMR (CDCl$_3$, δ): 1.24 (3H, t, J=7 Hz), 1.91 (2H, m), 2.23 (3H, s), 2.32 (2H, t, J=7 Hz), 2.74 (2H, t, J=7 Hz), 4.11 (2H, q, J=7 Hz), 6.32 (1H, dr, J=1 Hz, 7 Hz), 6.53 (1H, m), 7.08 (1H, s), 7.21 (1H , d, J=9 Hz), 7.76 (1H, dt, J=7 Hz, 1 Hz)

Preparation 17

The following compound was obtained according to a similar manner to that of Preparation 1.

Ethyl 4-(2-methylindolizin-3-yl)-4-oxobutyrate

NMR (CDCl$_3$, δ): 1.28 (3H, t, J=7 Hz), 2.65 (3H, s), 2.79 (2H, t, J=7 Hz), 3.19 (2H, t, J=7 Hz), 4.18 (2H, q, J=7 Hz), 6.34 (1H, s), 6.78 (1H, dr, J=1 Hz, 7 Hz), 7.10 (1H, m), 7.40 (1H, d, J=8 Hz), 9.98 (1H, d, J=7 Hz)

Preparation 18

The following compound was obtained according to a similar manner to that of Preparation 2.

Ethyl 4-(2-methylindolizin-3-yl)butyrate

NMR (CDCl$_3$, δ): 1.24 (3H, t, J=7 Hz), 1.90 (2H, m), 2.28 (3H, s), 2.35 (2H, d, J=7 Hz), 2.91 (2H, d, J=7 Hz), 4.12 (2H, q, J=7 Hz), 6.25 (1H, m), 6.47 (1H, m), 6.60 (1H, m), 7.28 (1H, d, J=8 Hz), 7.79 (1H, m)

Preparation 19

The following compounds were obtained according to a similar manner to that of Preparation 4.

(1) Ethyl 4-[2-methyl-3-(4-nitrobenzoyl)indolizin-1-yl]butyrate

NMR (CDCl$_3$, δ): 1.23 (3H, t, J=7 Hz), 1.79 (3H, s), 1.86 (2H, m), 2.34 (2H, t, J=7 Hz), 2.72 (2H, t, J=7 Hz), 4.11 (2H, q, J=7 Hz), 6.92 (1H, dt, J=1 Hz, 7 Hz), 7.24 (1H, m), 7.52 (1H, d, J=9 Hz), 7.74 (2H, d, J=9 Hz), 8.34 (2H, d, J=9 Hz), 9.87 (1H, d, J=8 Hz)

(2) Ethyl 4-[2-methyl-3-(3-nitrobenzoyl)indolizin-1-yl]butyrate

NMR (CDCl$_3$, δ): 1.24 (3H, t, J=7 Hz), 1.84 (3H, s), 1.88 (2H, m), 2.35 (2H, t, J=7 Hz), 2.73 (2H, t, J=7 Hz), 4.13 (2H, q, J=7 Hz), 6.90 (1H, dt, J=1 Hz, 7 Hz), 7.22 (1H, m), 7.52 (1H, d, J=9 Hz), 7.68 (1H, t, J=8 Hz), 7.93 (1H, m), 8.37 (1H, m), 8.46 (1H, m), 9.83 (1H, d, J=7 Hz) (3) Ethyl 4-[2-methyl-1-(4-nitrobenzoyl)indolizin-3-yl ]butyrate NMR(CDCl$_3$, δ): 1.27 (3H, t, J=7 Hz), 1.91 (2H, m), 2.19 (3H, s), 2.41 (2H, t, J=7 Hz), 2.93 (2H, t, J=7 Hz), 4.15 (2H, q, J=7 Hz), 6.84 (1H, dt, J=1 Hz, 7 Hz), 7.02 (1H, m), 7.51 (1H, dt, J=9 Hz, 1 Hz), 7.80 (2H, d, J=8 Hz), 8.09 (1H, d, J=7 Hz), 8.32 (2H, d, J=8 Hz)

(4) Ethyl 4-[2-methyl-1-(3-nitrobenzoyl)indolizin-3-yl ]butyrate

NMR (CDCl$_3$, δ): 1.26 (3H, t, J=7 Hz), 1.92 (2H, m), 2.20 (3H, s), 2.42 (2H, t, J=7 Hz), 2.94 (2H, t, J=7 Hz), 4.17 (2H, q, J=7 Hz), 6.84 (1H, dt, J=1 Hz, 7 Hz), 7.02 (1H, m), 7.53 (1H, dt, J=8 Hz, 1 Hz), 7.68 (1H, t, J=8 Hz), 8.0–8.15 (2H, m), 8.38 (1H, m), 8.50 (1H, m)

Preparation 20

The following compounds were obtained according to a similar manner to that of Preparation 6.

Ethyl 4-[3-(4-aminobenzoyl)-2-methylindolizin-1-yl]butyrate

NMR (CDCl$_3$, δ): 1.24 (3H, t, J=7 Hz), 1.88 (2H, m), 1.99 (3H, s), 2.34 (2H, t, J=7 Hz), 2.73 (2H, t, J=7 Hz), 4.11 (2H, q, J=7 Hz), 6.64–6.75 (1H, m), 6.68 (2H, d,

J=8 Hz), 7.00 (1H, m), 7.42 (1H, dt, J=9 Hz, 1 Hz), 7.53 (2H, d, J=8 Hz), 9.88 (1H, d, J=7 Hz)

(2) Ethyl 4-[3-(3-aminobenzoyl)-2-methylindolizin-1-yl]butyrate

NMR (CDCl$_3$, δ): 1.22 (3H, t, J=7 Hz), 1.75–1.95 (2H, m), 1.89 (3H, s), 2.32 (2H, t, J=7 Hz), 2.72 (2H, t, J=7 Hz), 4.11 (2H, q, J=7 Hz), 6.78 (1H, dt, J=1 Hz, 7 Hz), 6.85–7.3 (5H, m), 7.44 (1H, d, J=9 Hz), 9.69 (1H, d, J=7 Hz)

(3) Ethyl 4-[1-(4-aminobenzoyl)-2-methylindolizin-3-yl]butyrate

NMR (CDCl$_3$, δ): 1.25 (3H, t, J=7 Hz), 1.91 (2H, m), 2.29 (3H, s), 2.39 (2H, t, J=7 Hz), 2.93 (2H, t, J=7 Hz), 4.15 (2H, q, J=7 Hz), 6.69 (1H, dt, J=7 Hz), 6.7–6.9 (3H, m), 7.46 (1H, d, J=9 Hz), 7.64 (2H, d, J=8 Hz), 7.96 (1H, d, J=7 Hz)

(4) Ethyl 4-[1-(3-aminobenzoyl)-2-methylindolizin-3-yl]butyrate

NMR (CDCl$_3$, δ): 1.27 (3H, t, J=7 Hz), 1.92 (2H, m), 2.28 (3H, s), 2.39 (2H, t, J=7 Hz), 2.93 (2H, t, J=7 Hz), 4.14 (2H, q, J=7 Hz), 6.72 (1H, dt, J=1 Hz, 7 Hz), 6.8–6.95 (2H, m), 7.0–7.1 (2H, m), 7.21 (1H, t, J=8 Hz), 7.46 (1H, dt, J=8 Hz, 1 Hz), 7.99 (1H, d, J=7 Hz)

Preparation 21

N,N-Dimethylformamide (0.5 ml) was added to a solution of 4-acetoxybenzoic acid (50 g) and oxalyl chloride (27 ml) in dichloromethane (500 ml). The mixture was stirred for 2 hours at room temperature. The solvent was evaporated and the residue was dissolved in n-hexane (200 ml). After filtration, the solution was evaporated to give 4-acetoxybenzoyl chloride as a yellow oil (55.1 g).

NMR (CDCl$_3$, δ): 2.35 (3H, s), 7.27 (2H, d, J=9 Hz), 8.16 (2H, d, J=9 Hz)

Preparation 22

4-Acetoxybenzoyl chloride (53.6 g) was added to a suspension of aluminum chloride (36.5 g) in dichloromethane (500 ml). After the mixture was stirred for 20 minutes at room temperature, a solution of ethyl 4-(indolizin-3-yl)butyrate (57.8 g) in dichloromethane (50 ml) was added to the mixture. The mixture was stirred for 2 hours at room temperature and the solvent was evaporated. The residue was dissolved in ethyl acetate (500 ml) and washed with water. N,N-dimethylaminopropylamine (20 ml) was added to the solution. The mixture was washed with diluted hydrochloric acid, water, sodium bicarbonate aqueous solution and water. The solution was dried over magnesium sulfate and the solvent was removed in vacuo. The residue was washed with diisopropyl ether to give ethyl 4-[1-(4-acetoxybenzoyl)indolizin-3-yl]butyrate as yellow powder (36.5 g).

NMR (CDCl$_3$, δ): 1.25 (3H, t, J=7 Hz), 2.0–2.2 (2H, m), 2.35 (3H, s), 2.43 (2H, t, J=7 Hz), 2.90 (2H, t, J=7 Hz), 4.12 (2H, q, J=7 Hz), 6.85–7.0 (2H, m), 7.15–7.3 (1H, m), 7.25 (2H, d, J=8 Hz), 7.88 (2H, d, J=8 Hz), 8.03 (1H, d, J=7 Hz), 8.52 (1H, d, J=9 Hz)

Preparation 23

Sodium hydride (60% dispersion in mineral oil) (4.38 g) was added to an ice cold solution of ethyl 4-[1-(4-acetoxybenzoyl)indolizin-3-yl]butyrate (36.1 g) in a mixture of ethanol (200 ml) and tetrahydrofuran (200 ml). The mixture was stirred for 20 minutes at 0° C. and evaporated. The residual solution was poured into a mixture of diluted hydrochloric acid and ice, and extracted with a mixture of chloroform and methanol (10:1). The organic layer was washed with a sodium bicarbonate aqueous solution and brine, dried over magnesium sulfate and evaporated. The residue was washed with ethyl acetate and diethyl ether to give ethyl 4-[1-(4-hydroxybenzoyl)indolizin-3-yl]butyrate as yellow powder (29.3 g).

NMR (CDCl$_3$, δ): 1.25 (3H, t, J=7 Hz), 2.0–2.2 (2H, m), 2.45 (2H, t, J=7 Hz), 2.89 (2H, t, J=7 Hz), 4.15 (2H, q, J=7 Hz), 6.8–7.0 (4H, m), 7.18 (1H, t, J=9 Hz), 7.78 (2H, d, J=8.5 Hz), 8.00 (1H, d, J=5.5 Hz), 8.50 (1H, d, J=9 Hz)

Preparation 24

4'-Isobutylbutanophenone (1.2 g) was added to a solution of (+)-B-chlorodiisopinocampheylborane (2.10 g) in tetrahydrofuran (4 ml) at 25° C. After 5 hours, the solvent was removed and the residue was dissolved in ethyl ether (20 ml). Diethanolamine (1.4 ml) was added to the mixture and the mixture was stirred for 2 hours. The solid was filtered off and washed with ethyl ether. The combined filtrates were concentrated and the residue was chromatographed on silica gel (eluent:hexane:CH$_2$Cl$_2$=1:2) to give (R)-1-(4-isobutylphenyl)butan-1-ol (937 mg).

NMR (CDCl$_3$, δ): 0.89 (6H, d, J=7 Hz), 0.92 (3H, t, J=7 Hz), 1.2–1.5 (4H, m), 1.6–2.0 (3H, m), 2.47 (2H, d, J=7 Hz), 4.63 (1H, t, J=7 Hz), 7.11 (2H, d, J=8 Hz), 7.25 (2H, d, J=8 Hz)

Preparation 25

The following compound was obtained by treating 4'-isobutylbutanophenone with (−)-B-chlorodiisopinocampheylborane according to a similar manner to that of Preparation 24.

(S)-1-(4-Isobutylphenyl)butan-1-ol

NMR (CDCl$_3$, δ): 0.85–1.0 (9H, m), 1.15–1.95 (5H, m), 2.47 (2H, d, J=7 Hz), 4.66 (1H, t, J=7 Hz), 7.12 (2H, d, J=8 Hz), 7.25 (2H, d, J=8 Hz)

Preparation 26

To a solution of chlorotrimethylsilane (16.3 g) and triethylamine (30.3 g) in N,N-dimethylformamide (50 ml) was added 4'-isobutylacetophenone (22.0 g). The yellow solid was immediately filtered off, and the filtrate was refluxed for 20 hours. The mixture was cooled, diluted with hexane, and washed with cooled aqueous sodium bicarbonate. The organic layer was dried over magnesium sulfate and concentrated. The residue was distilled under reduced pressure to give 4-isobutyl-α-trimethylsilyloxystyrene (9.0 g) as an oil.

NMR (CDCl$_3$, δ): 0.16 (9H, s), 1.65–1.85 (1H, m), 2.35 (2H, d, J=7 Hz), 4.27 (1H, d, J=1.5 Hz), 4.76 (1H, d, J=1.5 Hz), 6.98 (2H, d, J=8.5 Hz), 7.38 (2H, d, J=8.5 Hz)

Preparation 27

Iodosylbenzene (2.18 g) was dissolved in ethanol (45 ml), and boron trifluoride etherate (2.55 g) was added. The mixture was stirred at −70° C., and then 4-isobutyl-α-trimethylsilyloxystyrene (2.24 g) was added. The mixture was stirred at −70° C. for 30 minutes, and then the temperature was slowly raised to room temperature. The ethanol was evaporated and water was added. The mixture was neutralized with aqueous sodium bicarbonate. The mixture was extracted with dichloromethane, and the organic phase was dried over magnesium sulfate, and concentrated. The residue was chromatographed on silica gel column eluting with hexane-ethyl acetate (94:6) to give 4'-isobutyl-2-ethoxyacetophenone (1.90 g) as an oil.

NMR (CDCl₃, δ): 0.91 (6H, d, J=7 Hz), 1.30 (3H, t, J=7 Hz), 1.80–2.0 (1H, m), 2.53 (2H, d, J=7 Hz), 3.65 (2H, q, J=7 Hz), 4.74 (2H, s), 7.24 (2H, d, J=8 Hz), 7.87 (2H, d, J=8 Hz)

Preparation 28

The following compound was obtained by treating 4'-isobutyl-2-ethoxyacetophenone with (−)-B-chlorodiisopinocampheylborane according to a similar manner to that of Preparation 24.

(R)-i-(4-Isobutylphenyl)-2-ethoxyethanol

NMR (CDCl₃, δ): 0.89 (6H, d, J=7 Hz), 1.25 (3H, t, J=7 Hz), 1.75–1.95 (1H, m), 2.47 (2H, d, J=7 Hz), 3.35–3.7 (4H, m), 4.87 (1H, dd, J=5.5 Hz, 6.5 Hz), 7.13 (2H, d, J=8.5 Hz), 7.29 (2H, d, J=8.5 Hz)

Preparation 29

The following compound was obtained by treating 4'-isobutyl-2-ethoxyacetophenone with (+)-B-chlorodiisopinocampheylborane according to a similar manner to that of Preparation 24.

(S)-1-(4-Isobutylphenyl)-2-ethoxyethanol

NMR (CDCl₃, δ): 0.89 (6H, d, J=7 Hz), 1.25 (3H, t, J=7 Hz), 1.75–1.95 (1H, m), 2.47 (2H, d, J=7 Hz), 2.79 (1H, s), 3.35–3.7 (4H, m), 4.87 (1H, dd, J=5.5 Hz, 6.5 Hz), 7.13 (2H, d, J=8.5 Hz), 7.29 (2H, d, J=8.5 Hz)

Preparation 30

The following compounds were obtained according to similar manner to that of Example 1.

Ethyl 4-[1-[3-(benzyloxycarbonylmethylamino)benzoyl]-indolizin-3-yl]butyrate

NMR (CDCl₃, δ): 1.23 (3H, t, J=7 Hz), 2.05 (2H, m), 2.42 (2H, t, J=7 Hz), 2.86 (2H, t, J=7 Hz), 4.07 (2H, s), 4.11 (2H, q, J=7 Hz), 5.21 (2H, s), 6.8–7.0 (3H, m), 7.1–7.4 (9H, m), 8.01 (1H, d, J=8 Hz), 8.48 (1H, d, J=9 Hz)

(2) Ethyl-4-[1-[3-[(1-benzyloxycarbonylethyl)amino]-benzoyl]indolizin-3-yl]butyrate NMR (CDCl₃, δ): 1.24 (3H, t, J=7 Hz), 1.52 (3H, d, J=7 Hz), 2.05 (2H, m), 2.42 (2H, t, J=7 Hz), 2.85 (2H, t, J=7 Hz), 4.12 (2H, q, J=7 Hz), 4.27 (1H, q, J=7 Hz), 5.16 (2H, s), 6.7–7.0 (3H, m), 7.1–7.4 (9H, m), 8.00 (1H, d, J=7 Hz), 8.48 (1H, d, J=9 Hz)

Preparation 31

To a solution of ethyl 4-[1-[3-[(1-benzyloxycarbonylethyl)amino]benzoyl]indolizin-3-yl]butyrate (0.20 g) in ethanol (10 ml) was added 10% palladium on carbon (0.1 g). The mixture was stirred under hydrogen atmosphere at room temperature for 2 hours. Removal of catalyst and evaporation of solvent gave ethyl 4-[1-[3-(1-carboxyethylamino)benzoyl]indolizin-3-yl]butyrate (0.15 g) as yellow powder.

NMR (CDCl₃, δ): 1.25 (3H, t, J=7 Hz), 1.57 (3H, d, J=7 Hz), 2.0–2.3 (2H, m), 2.50 (2H, t, J=7 Hz), 2.83 (2H, t, J=7 Hz), 4.16 (3H, q, J=7 Hz), 6.8–7.0 (3H, m), 7.1–7.4 (4H, m), 7.96 (1H, d, J=7 Hz), 8.55 (1H, d, J=9 Hz)

Preparation 32

The following compound was obtained according to a similar manner to that of Preparation 31.

Ethyl 4-[1-(3-carboxymethylaminobenzoyl)indolizin-3yl]butyrate

NMR (CDCl₃, δ): 1.28 (3H, t, J=7 Hz), 2.15 (2H, m), 2.50 (2H, t, J=7 Hz), 2.83 (2H, t, J=7 Hz), 4.00 (2H, s), 4.17 (2H, q, J=7 Hz), 6.8–7.1 (3H, m), 7.2–7.4 (4H, m), 7.96 (1H, d, J=7 Hz), 8.55 (1H, d, J=9 Hz)

Preparation 33

To a mixture of (cyclopropylmethyl)benzene (1.32 g) and dichloromethyl methyl ether (1.25 ml) in dichloromethane (20 ml) was added 1.0M solution of titanium-(IV) chloride in dichloromethane (15 ml) at 0° C. under nitrogen atmosphere. The mixture was stirred at 0° C. for 10 minutes, then poured into ice water. The organic layer was separated and washed with water, dried over magnesium sulfate and concentrated. The residue was chromatographed on silica gel column eluting with a mixture of hexane and ethyl acetate (9:1) to give 4-(cyclopropylmethyl)benzaldehyde (580 mg) as an oil.

NMR (CDCl₃, δ): 0.5–0.65 (2H, m), 0.9–1.2 (1H, m), 2.63 (2H, d, J=7 Hz), 7.43 (2H, d, J=8.5 Hz), 7.82 (2H, d, J=8.5 Hz), 9.99 (1H, s)

Preparation 34

To a solution of allylmagnesium bromide (1.0M in diethyl ether, 3 ml) in diethyl ether (5 ml) was added dropwise 4-(cyclopropylmethyl)benzaldehyde (240 mg) in diethyl ether (2 ml) at 0° C. After 15 minutes, the reaction mixture was quenched by aqueous ammonium chloride and the resulting mixture was extracted with ethyl acetate. The organic layer was washed with water, dried over magnesium sulfate and concentrated. The residue was chromatographed on silica gel column eluting with a mixture of hexane and ethyl acetate (85:15) to give 1-[4-(cyclopropylmethyl)phenyl]-3-buten-1-ol (229 mg) as an oil.

NMR (CDCl₃, δ): 0.45–0.6 (2H, m), 0.85–1.2 (1H, m), 2.55 (2H, d, J=6.5 Hz), 4.72 (1H, t, J=6.5 Hz), 5.1–5.25 (2H, m), 5.7–5.95 (1H, m), 7.15–7.35 (4H, m)

Preparation 35

The following compound was obtained according to a similar manner to that of Preparation 34.

1-(4-Isobutylphenyl)-3-buten-1-ol

NMR (CDCl₃, δ): 0.89 (6H, d, J=7 Hz), 1.85 (1H, m), 2.47 (2H, d, J=7 Hz), 2.52 (2H, m), 4.72 (1H, m), 5.1–5.25 (2H, m), 5.83 (1H, m), 7.13 (2H, d, J=8 Hz), 7.27 (2H, d, J=8 Hz)

Preparation 36

To a stirred solution of pyridine (1.98 ml) in dichloromethane (15 ml) was added chromium(VI) oxide (1.23 g) at 0° C. After 30 minutes, 1-(4-isobutylphenyl)-3-buten-1-ol (525 mg) in dichloromethane (2 ml) was added and stirred for 20 minutes at ambient temperature. The reaction mixture was filtered through Florisil and washed with ether. The filtrate was concentrated in vacuo and chromatographed on silica gel (hexane:dichloromethane=1:1) to give 1-(4-isobutylphenyl)-3-buten-1-one (424 mg).

NMR (CDCl₃, δ): 0.92 (6H, d, J=7 Hz), 1.90 (1H, m), 2.53 (2H, d, J=7 Hz), 3.75 (2H, dt, J=7.1 Hz), 5.18 (1H, m), 5.25 (1H, m), 6.10 (1H, m), 7.23 (2H, d, J=8 Hz), 7.89 (2H, d, J=8 Hz)

Preparation 37

A mixture of 2-hydroxy-4-methylbenzoic acid (7.61 g), iodomethane (15.6 ml) and potassium carbonate (17.3 g) in N,N-dimethylformamide (100 ml) was stirred at room temperature for 5 hours. The reaction mixture was filtered and the filtrate was poured into a mixture of ethyl acetate and water. The organic layer was separated, washed with water and brine, dried over magnesium sulfate and concentrated. The residue was chromatographed on silica gel column eluting with a mixture of n-hexane and ethyl acetate (4:1) to give methyl 2-methoxy-4-methylbenzoate (7.99 g) as an oil.

NMR (CDCl$_3$, δ): 2.39 (3H, s), 3.88 (3H, s), 3.90 (3H, s), 6.75–6.85 (2H, m), 7.73 (1H, d, J=8.5 Hz)

Preparation 38

The following compound was obtained according to a similar manner to that of Preparation 37.
Methyl 3-methoxy-4-methylbenzoate
NMR (CDCl$_3$, δ): 2.27 (3H, s), 3.88 (3H, s), 3.91 (3H, s), 7.18 (1H, d, J=8 Hz), 7.45–7.6 (2H, m)

Preparation 39

A mixture of methyl 2-methoxy-4-methylbenzoate (6.95 g), N-bromosuccinimide (8.24 g) and catalytic amount of benzoyl peroxide (20 mg) in carbon tetrachloride (100 ml) was heated at reflux for 2 hours. The reaction mixture was cooled to room temperature and filtered. The filtrate was concentrated and the residue was chromatographed on silica gel column eluting with a mixture of n-hexane and ethyl acetate (85:15) to give methyl 4-bromomethyl-2methoxybenzoate (2.92 g) as an oil.

NMR (CDCl$_3$, δ): 3.89 (3H, s), 3.93 (3H, s), 4.47 (2H, s), 6.95–7.05 (2H, m), 7.77 (1H, d, J=8.5 Hz)

Preparation 40

The following compound was obtained according to a similar manner to that of Preparation 39.
Methyl 4-bromomethyl-3-methoxybenzoate
NMR (CDCl$_3$, δ): 3.93 (3H, s), 3.97 (3H, s), 4.56 (2H, s), 7.40 (1H, d, J=8 Hz), 7.5–7.65 (2H, m)

Preparation 41

A mixture of methyl 4-bromomethyl-3-methoxybenzoate (1.55 g) and triethyl phosphite (1.54 ml) was heated under nitrogen atmosphere at 50° C. for 30 minutes. The temperature was then raised to 200° C. for 2 hours. The bright yellow liquid was then cooled and chromatographed on silica gel column eluting with ethyl acetate to give diethyl (3-methoxy-4-methoxycarbonylbenzyl)phosphonate (1.28 g) as an oil.

NMR (CDCl$_3$, δ): 1.2–1.4 (6H, m), 3.18 (2H, d, J=22 Hz), 3.88 (3H, s), 3.92 (3H, s), 3.95–4.2 (4H, m), 6.85–7.0 (2H, m), 7.77 (1H, d, J=8 Hz)

Preparation 42

The following compound was obtained according to a similar manner to that of Preparation 41.
Diethyl (2-methoxy-4-methoxycarbonylbenzyl)phosphonate
NMR (CDCl$_3$, δ): 1.24 (6H, t, J=7 Hz), 3.29 (2H, d, J=22 Hz), 3.89 (3H, s), 3.91 (3H, s), 3.95–4.1 (4H, m), 7.38 (1H, dd, J=8 Hz, 3 Hz), 7.5–7.65 (2H, m)

Preparation 43

To a mixture of diethyl (3-methoxy-4-methoxycarbonylbenzyl)phosphonate (1.28 g) and acetone (1.5 ml) in N,N-dimethylformamide (5 ml) was added 60% sodium hydride-oil dispersion (162 mg). The reaction mixture was stirred at room temperature for 14 hours and then poured into ice-cooled 10% citric acid. The mixture was extracted with ether and the organic layer was washed with water and brine, dried over magnesium sulfate and concentrated. The residue was chromatographed on silica gel column eluting with a mixture of n-hexane and ethyl acetate (85:15) to give methyl 2-methoxy-4-(2-methyl-1propenyl)benzoate (184 mg) as an oil.

NMR (CDCl$_3$, δ): 1.89 (3H, d, J=1.5 Hz), 1.93 (3H, d, J=1.5 Hz), 3.89 (3H, s), 3.91 (3H, s), 6.27 (1H, s), 6.8–6.9 (2H, m), 7.78 (1H, d, J=8 Hz)

Preparation 44

The following compound was obtained according to a similar manner to that of Preparation 43.
Methyl 3-methoxy-4-(2-methyl-1-propenyl)benzoate
NMR (CDCl$_3$, δ): 1.83 (3H, d, J=1.5 Hz), 1.97 (3H, d, J=1.5 Hz), 3.89 (3H, s), 3.92 (3H, s), 6.33 (1H, s), 7.25 (1H, d, J=8 Hz), 7.52 (1H, d, J=1.5 Hz), 7.62 (1H, dd, J=8 Hz, 1.5 Hz)

Preparation 45

To a solution of methyl 2-methoxy-4-(2-methyl-1propenyl)benzoate (178 mg) in methanol (3 ml) and 1,4-dioxane (3 ml) was added 1N aqueous solution of sodium hydroxide (2 ml). The mixture was stirred at 50° C. for 3 hours, and then poured into a mixture of ethyl acetate and 0.5N hydrochloric acid. The organic layer was separated, washed with water and brine, dried over magnesium sulfate. Evaporation of the solvent gave 2-methoxy-4-(2-methyl-1propenyl)benzoic acid (142 mg) as solid.

NMR (CDCl$_3$, δ): 1.91 (3H, d, J=1.5 Hz), 1.95 (3H, d, J=1.5 Hz), 4.08 (3H, s), 6.27 (1H, s), 6.87 (1H, s), 7.01 (1H, dd, J=1.5 Hz, 8 Hz), 8.12 (1H, d, J=8 Hz)

Preparation 46

The following compound was obtained according to a similar manner to that of Preparation 45.
3-Methoxy-4-(2-methyl-1-propenyl)benzoic acid
NMR (CDCl$_3$, δ): 1.85 (3H, s), 1.97 (3H, s), 3.90 (3H, s), 6.34 (1H, s), 7.28 (1H, d, J=8 Hz), 7.58 (1H, s), 7.70 (1H, d, J=8 Hz)

Preparation 47

A mixture of 1-iodobutane (185 mg) and zinc-copper couple (101 mg) in benzene (3 ml) and N,N-dimethylformamide (0.2 ml) was stirred at 60° C. for 2 hours. To the mixture, a solution of tetrakis(triphenylphosphine)palladium (31 mg) and 2-methoxy-4-(2-methyl-1-propenyl)benzoyl chloride (prepared from 138 mg of 2-methoxy-4-(2-methyl-1propenyl)benzoic acid and 0.07 ml of oxalyl chloride) in benzene (2 ml) was added, and the reaction mixture was stirred at room temperature for 30 minutes. The mixture was filtered and the filtrate was concentrated. The residue was dissolved in ethyl acetate and the organic solution was washed with water and brine, dried over magnesium sulfate and concentrated. The residue was chromatographed on silica gel column eluting with a mixture of hexane and ethyl acetate (9:1) to give 2'-methoxy-4'-(2-methyl-1-propenyl)valerophenone (91 mg) 10 as an oil.

NMR (CDCl$_3$, δ): 0.93 (3H, t, J=7.5 Hz), 1.25–1.5 (2H, m), 1.55–1.75 (2H, m), 1.90 (3H, d, J=1.5 Hz), 1.93 (3H, d, J=1.5 Hz), 2.97 (2H, t, J=7.5 Hz), 3.89 (3H, s), 6.27 (1H, s), 6.78 (1H, s), 6.87 (1H, d, J=8 Hz), 7.66 (1H, d, J=8 Hz)

Preparation 48

The following compound was obtained according to a similar manner to that of Preparation 47.

3'-Methoxy-4'-(2-methyl-7-propenyl)valerophenone

NMR (CDCl$_3$, δ): 0.97 (3H, t, J=7.5 Hz), 1.3–1.55 (2H, m), 1.6–1.8 (2H, m), 1.84 (3H, d, J=1.5 Hz), 1.97 (3H, d, J=1.5 Hz), 2.97 (2H, t, J=7.8 Hz), 3.90 (3H, s), 6.33 (1H, s), 7.26 (1H, d, J=8 Hz), 7.45–7.6 (2H, m)

Preparation 49

A mixture of 2'-methoxy-4'-(2-methyl-1-propenyl)-valerophenone (88 mg) and 10% palladium on carbon (30 mg) was stirred under hydrogen atmosphere for 30 minutes. Catalyst was removed by filtration and the filtrate was concentrated. The residue was dissolved in methanol (5 ml) and then sodium borohydride (16 mg) was added. The reaction mixture was stirred at room temperature for 30 minutes. The mixture was poured into ice water and acidified with 6N hydrochloric acid and extracted with ethyl acetate. The organic layer was washed with water and brine, dried over magnesium sulfate and concentrated to give 1-(4-isobutyl-2-methoxyphenyl)pentanol (88 mg) as an oil.

NMR (CDCl$_3$, δ): 0.8–0.95 (9H, m), 1.2–1.55 (4H, m), 1.65–2.0 (3H, m), 2.46 (2H, d, J=7 Hz), 2.54 (1H, d, J=6.5 Hz), 3.85 (3H, s), 4.81 (1H, dd, J=6 Hz, 13 Hz), 6.65 (1H, s), 6.73 (1H, d, J=8 Hz), 7.17 (1H, d, J=8 Hz)

Preparation 50

The following compound was obtained according to a similar manner to that of Preparation 49.

1-(4-Isobutyl-3-methoxyphenyl)pentanol

NMR (CDCl$_3$, δ): 0.8–0.95 (9H, m), 1.2–1.5 (4H, m), 1.65–2.0 (4H, m), 2.47 (2H, d, J=7 Hz), 3.82 (3H, s), 4.55–4.7 (1H, m), 6.75–6.9 (2H, m), 7.04 (1H, d, J=7 Hz)

Preparation 51

A mixture of (4-bromo-2-fluorobenzyl)triphenylphosphonium bromide (3.82 g) and potassium t-butoxide (786 mg) was stirred at room temperature for 30 minutes. Then acetone (1.0 ml) was added and the reaction mixture was heated at reflux for 40 hours. The mixture was filtered, and the filtrate was concentrated. The residue was dissolved in ethyl acetate, washed with water and brine, dried over magnesium sulfate and the solvent was evaporated. The residue was chromatographed on silica gel column eluting with hexane to give 1-(4-bromo-2-fluorophenyl)-2-methyl-1-propene (0.70 g) as an oil.

NMR (CDCl$_3$, δ): 1.77 (3H, s), 1.92 (3H, s), 6.12 (1H, s), 7.0–7.3 (3H, m)

Preparation 52

A solution of 3-fluoro-4-(2-methyl-1-propenyl)-phenylmagnesium bromide was prepared in the usual manner with ether (10 ml), magnesium (82 mg) and 1-(2-fluoro-4-bromophenyl)-2-methyl-1-propene (0.70 g). A solution of valeraldehyde (526 mg) in ether (5 ml) was added dropwise to the Grignard solution and the mixture was stirred at room temperature for 30 minutes. Aqueous ammonium chloride was added to the mixture and organic layer was separated, washed with water and brine, dried over magnesium sulfate and concentrated. The residue was chromatographed on silica gel column eluting with a mixture of hexane and ethyl acetate (85:15) to give 1-[3-fluoro-4-(2-methyl-1-propenyl)-phenyl]pentanol (369 mg) as an oil.

NMR (CDCl$_3$, δ): 0.88 (3H, t, J=6.5 Hz), 1.15–1.5 (4H, m), 1.6–1.85 (5H, m), 1.92 (3H, s)

Preparation 53

A mixture of 1-[3-fluoro-4-(2-methyl-1-propenyl)-phenyl]pentanol (300 mg) and 10% palladium on carbon (90 mg) in methanol (10 ml) was stirred under hydrogen atmosphere for 30 minutes at room temperature. Catalyst was removed by filtration and the solvent was evaporated. The residue was chromatographed on silica gel column eluting with a mixture of hexane and ethyl acetate (85:15) to give 1-(3-fluoro-4-isobutylphenyl)-pentanol (167 mg) as an oil.

NMR (CDCl$_3$, δ): 0.8–0.95 (9H, m), 1.15–1.5 (4H, m), 1.6–2.0 (4H, m), 2.49 (2H, dd, J=1 Hz, 7.5 Hz), 4.55–4.7 (1H, m), 6.95–7.2 (3H, m)

Preparation 54

Sodium (317 mg) was dissolved in ethanol (30 ml), then 2-nitropropane (1.24 ml) was added. To the mixture 4-bromo-2-fluorobenzyl bromide (3.55 g) in ethanol (10 ml) was added. The reaction mixture was stirred at room temperature for 3 hours, and insoluble materials were filtered off. The filtrate was concentrated and the residue was dissolved in diethyl ether and water. The organic layer was washed with 1N sodium hydroxide and water, dried over magnesium sulfate and concentrated. The residue was chromatographed on silica gel column eluting with a mixture of hexane and ethyl acetate (20:1) to give 4-bromo-2-fluorobenzaldehyde (2.28 g) as solid.

NMR (CDCl$_3$, δ): 7.35–7.55 (2H, m), 7.7–7.85 (1H, m)

Preparation 55

A solution of butylmagnesium bromide was prepared in the usual manner with diethyl ether (5 ml), magnesium (111 mg) and 1-bromobutane (624 mg). A solution of 4-bromo-2-fluorobenzaldehyde (925 mg) in diethyl ether (5 ml) was added dropwise to the Grignard solution. After the addition was completed, the reaction mixture was stirred for 30 minutes at room temperature. The reaction was quenched with aqueous ammonium chloride and the organic layer was separated, washed with water and brine, dried over magnesium sulfate and concentrated. The residue was chromatographed on silica gel column eluting with a mixture of hexane and ethyl acetate (85:15) to give 1-(4-bromo-2-fluorophenyl)pentanol (635 mg) as an oil.

NMR (CDCl$_3$, δ): 0.90 (3H, t, J=7 Hz), 1.2–1.5 (4H, m), 1.65–1.9 (3H, m), 4.9–5.05 (1H, m), 7.15–7.45 (3H, m)

Preparation 56

A mixture of 1-(4-bromo-2-fluorophenyl)pentanol (630 mg), chloromethyl methyl ether (196 mg) and triethylamine (246 mg) was stirred at room temperature for 3 hours. The mixture was poured into ice water and extracted with ethyl acetate. The organic layer was washed with 0.5N hydrochloride acid, water and brine, dried over magnesium sulfate and concentrated. The residue was chromatographed on silica gel column eluting with a mixture of hexane and ethyl acetate (19:1) to give 1-(4-bromo-2-fluorophenyl)-l(methoxymethoxy)-pentane (558 mg) as an oil.

NMR (CDCl$_3$, δ): 0.89 (3H, t, J=7 Hz), 1.2-1.5 (4H, m), 1.6-1.9 (2H, m), 3.36 (3H, s), 4.5-4.6 (2H, m), 4.88 (1H, dd, J=5.5 Hz, 8 Hz), 7.15-7.35 (3H, m)

Preparation 57

To a solution of 1-(4-bromo-2-fluorophenyl)-1-methoxymethoxy)pentane (368 mg) in diethyl ether (5 ml) was added 1.6M solution of n-butyl lithium (1.4 ml) in hexane. The reaction mixture was stirred at −60° C. for 1 hour, then a solution of isobutylaldehyde (161 mg) in diethyl ether (1 ml) was added. After 30 minutes, aqueous ammonium chloride was added to the mixture. The organic layer was separated, washed with water and brine, dried over magnesium sulfate and concentrated. The residue was chromatographed on silica gel column eluting with a mixture of hexane and ethyl acetate (4:1) to give 1-[3-fluoro-4-[1-(methoxymethoxy)-pentyl]phenyl]-2methylpropanol (108 mg) as an oil.

NMR (CDCl$_3$, δ): 0.8-1.05 (9H, m), 1.15-2.05 (8H, m), 3.37 (3H, s), 4.38 (1H, d, J=6.5 Hz), 4.5-4.6 (2H, m), 4.92 (1H, dd, J=5.5 Hz, 8 Hz), 6.95-7.15 (2H, m), 7.3-7.4 (1H, t, J=8 Hz)

Preparation 58

A mixture of 1-[3-fluoro-4-[1-(methoxymethoxy)pentyl]phenyl]-2-methylpropanol (104 mg), acetic anhydride (66 mg) and N,N-dimethylaminopyridine (2 mg) was stirred at room temperature for 1 hour. The mixture was poured into ice water and extracted with ethyl acetate. The organic layer was washed with water and brine, dried over magnesium sulfate and concentrated. The residue was chromatographed on silica gel column eluting with a mixture of hexane and ethyl acetate (85:15) to give 1-[3-fluoro-4-[1-(methoxymethoxy)pentyl]phenyl]-2-methylpropyl acetate (113 mg) as an oil.

NMR (CDCl$_3$, δ): 0.75-1.0 (9H, m), 1.2-1.5 (4H, m), 1.6-1.9 (2H, m), 1.95-2.15 (4H, m), 3.36 (3H, s), 4.5-4.6 (2H, m), 4.90 (1H, dd, J=5.5 Hz, 8 Hz), 5.44 (1H, d, J=6.5 Hz), 6.95 (1H, dd, J=1 Hz, 10.5 Hz), 7.05 (1H, dd, J=1 Hz, 8 Hz), 7.35 (1H, t, J=8 Hz)

Preparation 59

A mixture of 1-[3-fluoro-4-[1-(methoxymethoxy)pentyl]phenyl]-2-methylpropyl acetate (110 mg) and 1N hydrochloric acid (0.3 ml) in acetic acid (3 ml) was stirred at room temperature for 1 hour. The solvent was evaporated under reduced pressure, and the residue was dissolved in ethyl acetate. The organic solution was washed with aqueous sodium bicarbonate, water and brine, dried over magnesium sulfate and concentrated. The residue was chromatographed on silica gel column eluting with a mixture of hexane and ethyl acetate to give 1-[3-fluoro-4-(1-hydroxypentyl)phenyl]-2-methylpropyl acetate (70 mg) as an oil.

NMR (CDCl$_3$, δ): 0.75-1.0 (9H, m), 1.2-1.5 (4H, m), 1.65-1.95 (2H, m), 2.0-2.15 (4H, m), 4.97 (1H, t, J=7 Hz), 5.43 (1H, d, J=7.5 Hz), 6.96 (1H, d, J=10.5 Hz), 7.06 (1H, d, J=8 Hz), 7.41 (1H, t, J=8 Hz)

Preparation 60

To a solution of (3-methoxycarbonylbenzyl)triphenylphosphonium chloride (6.0g) in tetrahydrofuran (120 ml) was added a solution of potassium tert-butoxide (2.0 g) in tetrahydrofuran (50 ml) at 0° C. After the mixture was stirred for 30 minutes, 4-isobutylbenzaldehyde (2.2 g) was added to the mixture. The mixture was allowed to stir for hours and poured into ice and diluted hydrochloric acid. The organic layer was extracted with ethyl acetate, washed with water, dried over magnesium sulfate and evaporated. The residue was purified by column chromatography on silica gel (300 g) eluting with a mixture of ethyl acetate and n-hexane (1:50) to give methyl 3-trans-[2-(4isobutylphenyl)vinyl]benzoate (2.23 g) as a white powder and methyl 3-cis-[2-(4-isobutylphenyl)vinyl]benzoate (1.25 g) as colorless oil.

Methyl 3-trans-[2-(4-isobutyl)vinyl]benzoate

NMR (CDCl$_3$, δ): 0.92 (6H, d, J=7 Hz), 1.88 (1H, m), 2.50 (2H, d, J=7 Hz), 3.95 (3H, s), 7.08 (1H, d, J=16 Hz), 7.15 (2H, d, J=9 Hz), 7.20 (1H, d, J=16 Hz), 7.43 (1H, m), 7.45 (2H, d, J=9 Hz), 7.68 (1H, d, J=7 Hz), 7.92 (1H, d, J=8 Hz), 8.20 (1H, s)

Methyl 3-cis-[2-(4-isobutyl)vinyl]benzoate

NMR (CDCl$_3$, δ): 0.90 (6H, d, J=7 Hz), 1.85 (1H, m), 2.43 (2H, d, J=7 Hz), 3.87 (3H, s), 6.55 (1H, d, J=1 Hz), 6.65 (1H, d, J=1 Hz), 7.00 (2H, d, J=8 Hz), 7.12 (2H, d, J=8 Hz), 7.28 (1H, t, J=8 Hz), 7.45 (1H, d, J=8 Hz), 7.85 (1H, d, J=8 Hz), 7.92 (1H, s)

Preparation 61

The following compounds were obtained according to a similar manner to that of Preparation 60.

Methyl 4-trans-[2-(4-isobutylphenyl)vinyl]benzoate

NMR (CDCl$_3$, δ): 0.90 (6H, d, J=7 Hz), 1.88 (1H, m), 2.50 (2H, d, J=7 Hz), 3.93 (3H, s), 7.08 (1H, d, J=16 Hz), 7.15 (2H, d, J=9 Hz), 7.20 (1H, d, J=16 Hz), 7.45 (2H, d, J=9 Hz), 7.55 (2H, d, J=9 Hz), 8.03 (2H, d, J=9 Hz)

Methyl 4-cis-[2-(4-isobutylphenyl)vinyl]benzoate

NMR (CDCl$_3$, δ): 0.90 (6H, d, J=7 Hz), 1.83 (1H, m), 2.43 (2H, d, J=7 Hz), 3.90 (3H, s), 6.55 (1H, d, J=1 Hz), 6.68 (1H, d, J=1 Hz), 7.00 (2H, d, J=9 Hz), 7.13 (2H, d, J=9 Hz), 7.32 (2H, d, J=9 Hz), 7.89 (2H, d, J=9 Hz)

Preparation 62

To a solution of methyl 3-trans-[2-(4-isobutylphenyl)-vinyl]benzoate (2.23 g) in dioxane (20 ml) was added 1N sodium hydroxide aqueous solution (10 ml). The mixture was stirred for 45 minutes at 100° C. and poured into ice and diluted hydrochloric acid. The organic layer was extracted with ethyl acetate, washed with water, dried over magnesium sulfate and evaporated. The residue was washed with n-hexane to give 3-trans-[2-(4-isobutylphenyl)vinyl]benzoic acid as white powder (1.74 g).

NMR (CDCl$_3$+CD$_3$OD, δ): 0.92 (6H, d, J=7 Hz), 1.89 (1H, m), 2.50 (2H, d, J=7 Hz), 7.08 (1H, d, J=16 Hz), 7.21 (1H, d, J=16 Hz), 7.15 (2H, d, J=8 Hz), 7.45 (2H, d, J=8 Hz), 7.43 (1H, m), 7.69 (1H, d, J=8 Hz), 7.95 (1H, d, J=8 Hz), 8.22 (1H, s)

Preparation 63

The following compounds were obtained according to a similar manner to that of Preparation 62.

(1) 4-trans-[2-(4-Isobutylphenyl)vinyl]benzoic acid

NMR (CDCl$_3$+CD$_3$OD, δ): 0.90 (6H, d, J=7 Hz), 1.88 (1H, m), 2.50 (2H, d, J=7 Hz), 7.08 (1H, d, J=16 Hz), 7.15 (2H, d, J=9 Hz), 7.22 (1H, d, J=16 Hz), 7.45 (2H, d, J=9 Hz), 7.56 (2H, d, J=9 Hz), 8.02 (2H, d, J=9 Hz)

(2) 3-cis-[2-(4-Isobutylphenyl)vinyl]benzoic acid

NMR (CDCl$_3$, δ): 0.90 (6H, d, J=7 Hz), 1.85 (1H, m), 2.45 (2H, d, J=7 Hz), 6.58 (1H, d, J=12 Hz), 6.70 (1H, d, J=12 Hz), 7.00 (2H, d, J=9 Hz), 7.13 (2H, d, J=9 Hz), 7.31 (1H, t, J=8 Hz), 7.50 (1H, d, J=8 Hz), 7.93 (1H, d, J=8 Hz), 8.00 (1H, s)

(3) 4-cis-[2-(4-Isobutylphenyl)vinyl]benzoic acid

NMR (CDCl$_3$, δ): 0.90 (6H, d, J=7 Hz), 1.87 (1H, m), 2.45 (2H, d, J=7 Hz), 6.55 (1H, d, J=1 Hz), 6.70 (1H, d, J=1 Hz), 7.02 (2H, d, J=9 Hz), 7.14 (2H, d, J=9 Hz), 7.36 (2H, d, J=9 Hz), 7.97 (2H, d, J=9 Hz)

Preparation 64

To a suspension of 3-trans-[2-(4-isobutylphenyl)-vinyl]benzoic acid (0.56 g) in dichloromethane (10 ml) was oxalyl chloride (0.5 ml) and N,N-dimethylformamide (0.05 ml). The mixture was stirred for 30 minutes at room temperature and evaporated. The residue was dissolved in n-hexane (10 ml) and filtered off. The filtrate was evaporated to give 3-trans-[2-(4-isobutylphenyl)vinyl]benzoyl chloride (0.54 g) as white powder.

NMR (CDCl$_3$, δ): 0.93 (6H, d, J=7 Hz), 1.90 (1H, m), 2.50 (2H, d, J=7 Hz), 7.08 (1H, d, J=16 Hz), 7.18 (2H, d, J=9 Hz), 7.21 (1H, d, J=16 Hz), 7.45 (2H, d, J=9 Hz), 7.5 (1H, m), 7.81 (1H, d, J=7 Hz), 8.00 (1H, d, J=9 Hz), 8.22 (1H, s)

Preparation 65

The following compounds were obtained according to a similar manner to that of Preparation 64.

(1) 4-cis-[2-(4-Isobutylphenyl)vinyl]benzoyl chloride

NMR (CDCl$_3$, δ): 0.90 (6H, d, J=7 Hz), 1.83 (1H, m), 2.45 (2H, d, J=7 Hz), 6.55 (1H, d, J=1 Hz), 6.77 (1H, d, J=1 Hz), 7.02 (2H, d, J=9 Hz), 7.13 (2H, d, J=9 Hz), 7.38 (2H, d, J=9 Hz), 7.97 (2H, d, J=9 Hz)

(2) 4-trans-[2-(4-Isobutylphenyl)vinyl]benzoyl chloride

NMR (CDCl$_3$, δ): 0.92 (6H, d, J=7 Hz), 1.38 (1H, m), 2.50 (2H, d, J=7 Hz), 7.08 (1H, d, J=16 Hz), 7.18 (2H, d, J=9 Hz), 7.30 (1H, d, J=16 Hz), 7.48 (2H, d, J=9 Hz), 7.60 (2H, d, J=9 Hz), 8.10 (2H, d, J=9 Hz)

(3) 3-cis-[2-(4-Isobutylphenyl)vinyl]benzoyl chloride

NMR (CDCl$_3$, δ): 0.90 (6H, d, J=7 Hz), 1.85 (1H, m), 2.43 (2H, d, J=7 Hz), 6.55 (1H, d, J=12 Hz), 6.72 (1H, d, J=12 Hz), 7.02 (2H, d, J=9 Hz), 7.12 (2H, d, J=9 Hz), 7.34 (1H, t, J=8 Hz), 7.55 (1H, d, J=8 Hz), 7.92 (1H, d, J=8 Hz), 8.02 (1H, s)

Preparation 66

The following compound was obtained by treating 1-(4-isobutylphenyl)-3-buten-1-one with (+)-B-chlorodiisopinocampheylborane according to a similar manner to that of Preparation 24.

(R)-1-(4-Isobutylphenyl)-3-buten-1-ol

NMR (CDCl$_3$, δ): 0.90 (6H, d, J=7 Hz), 1.86 (1H, m), 2.46 (2H, d, J=7 Hz), 2.52 (2H, m), 4.71 (1H, t, J=7 Hz), 5.12 (1H, m), 5.18 (1H, m), 5.83 (1H, m), 7.13 (2H, d, J=8 Hz), 7.27 (2H, d, J=7 Hz)

Preparation 67

The following compound was obtained according to a similar manner to that of Preparation 10.
4-Isobutylbenzophenone NMR (CDCl$_3$, δ): 0.94 (6H, d, J=7 Hz), 1.75-2.05 (1H, m), 2.57 (2H, d, J=7 Hz), 7.27 (2H, d, J=9 Hz), 7.35-7.85 (7H, m)

Preparation 68

To the solution of 4,4,4-trifluorobutyric acid (4.15 g) in dichloromethane (50 ml) was added oxalyl chloride (2.55 ml) and several drops of N,N-dimethylformamide. After the mixture was stirred at room temperature for 1 hour, the solvent was evaporated. The residue was dissolved in dichloromethane (100 ml), and then aluminum chloride (3.89 g) was added to the solution at 0° C. After the mixture was stirred at 0° C. for 30 minutes, isobutylbenzene (3.92 g) was added. The mixture was stirred at 0° C. for 1 hour and poured into ice water. The organic layer was separated, washed with water, aqueous sodium bicarbonate and brine, dried over magnesium sulfate. Evaporation of the solvent gave 4'-isobutyl-4,4,4-trifluorobutyrophenone (6.80 g) as an oil.

NMR (CDCl$_3$, δ): 0.91 (6H, d, J=7 Hz), 1.75-2.05 (1H, m), 2.45-2.7 (4H, m), 3.25 (2H, t, J=8 Hz), 7.26 (2H, d, J=8 Hz), 7.39 (2H, d, J=8 Hz)

Preparation 69

The following compounds were obtained according to a similar manner to that of Preparation 11.

(1) (4-Isobutylphenyl)benzyl alcohol

NMR (CDCl$_3$, δ): 0.89 (6H, d, J=7 Hz), 1.7-1.95 (1H, m), 2.19 (1H, d, J=4 Hz), 2.45 (2H, d, J=7 Hz), 5.33 (1H, d, J=4 Hz), 7.11 (2H, d, J=8 Hz), 7.15-7.45 (7H, m)

(2) 4,4,4-Trifluoro-1-(4-isobutylphenyl)butanol

NMR (CDCl$_3$, δ): 0.90 (6H, d, J=7 Hz), 1.75-2.4 (6H, m), 2.48 (2H, d, J=7 Hz), 4.72 (1H, t, J=6.5 Hz), 7.15 (2H, d, J=8 Hz), 7.25 (2H, d, J=8 Hz)

Preparation 70

The following compound was obtained according to a similar manner to that of Preparation 12.

(4-Isobutylphenyl)benzyl bromide

NMR (CDCl$_3$, δ): 0.90 (6H, d, J=7 Hz), 1.7-2.0 (1H, m), 2.47 (2H, d, J=7 Hz), 6.29 (1H, s), 7.10 (2H, d, J=8 Hz), 7.2-7.55 (7H, m)

EXAMPLE 1

To a stirred solution of ethyl 4-[1-(3-aminobenzoyl)indolizin-3-yl]butyrate (320 mg) in methylene chloride (10 ml) was added diisopropylethylamine (0.22 ml) and bis(4-isobutylphenyl)chloromethane (340 mg) in methylene chloride (5 ml) at room temperature. After stirring for 18 hours, the reaction mixture was evaporated and extracted with ether. The organic layers were washed with water and brine and dried over sodium sulfate. After evaporation of the solvent, the residue was chromatographed on silica gel (methylene chloride:ethyl acetate=20:1) to give ethyl 4-[1-[3-[bis(4-isobutylphenyl)methylamino]benzoyl]indolizin-3-yl]butyrate (279 mg).

NMR (CDCl$_3$, δ): 0.92 (12H, d, J=7 Hz), 1.28 (3H, t, J=7 Hz), 1.87 (2H, m), 2.08 (2H, m), 2.4-2.55 (6H, m), 2.88 (2H, t, J=7 Hz), 4.25 (2H, q, J=7 Hz), 5.56 (1H, s), 6.70 (1H, d, J=8 Hz), 6.86 (1H, s), 6.90 (1H, dt, J=1 Hz, 7 Hz), 7.0-7.4 (12H, m), 8.02 (1H, d, J=7 Hz), 8.50 (1H, d, J=9 Hz)

EXAMPLE 2

The following compounds were obtained according to a similar manner to that of Example 1.

(1) Ethyl 4-[1-[4-[bis(4-isobutylphenyl)methylamino]benzoyl]indolizin-3-yl]butyrate NMR (CDCl$_3$, δ): 0.89 (12H, d, J=7 Hz), 1.24 (3H, t, J=7 Hz), 1.85 (2H, m), 2.05 (2H, m), 2.35-2.5 (6H, m), 2.88 (2H, t, J=7 Hz), 4.12 (2H, q, J=7 Hz), 5.56 (1H, s), 6.59 (2H, d, J=9 Hz), 6.82 (1H, dt, J=1 Hz, 7 Hz), 6.92 (1H, s), 7.09 (1H, m), 7.12 (4H, d, J=8 Hz), 7.25 (4H, d, J=8 Hz), 7.72 (2H, d, J=9 Hz), 7.96 (1H, d, J=7 Hz), 8.42 (1H, d, J=8 Hz)

(2) Ethyl 4- [3-[3- [bis(4-isobutylphenyl)methylamino]benzoyl]indolizin-1-yl]butyrate NMR (CDCl₃, δ): 0.87 (12H, d, J=7 Hz), 1.22 (3H, t, J=7 Hz), 1.7-2.05 (4H, m), 2.32 (2H, t, J=7 Hz), 2.43 (4H, d, J=7 Hz), 2.73 (2H, t, J=7 Hz), 4.10 (2H, q, J=7 Hz), 5.52 (1H, s), 6.68 (1H, m), 6.88 (1H, dt, J=1 Hz, 7 Hz), 7.0-7.3 (13H, m), 7.52 (1H, dt, J=8 Hz, 1 Hz), 9.92 (1H, d, J=7 Hz)

(3) Ethyl 4-[3-[4-[bis(4-isobutylphenyl)methylamino]-benzoyl]indolizin-1-yl]butyrate NMR (CDCl₃, δ): 0.89 (12H, d, J=7 Hz), 1.22 (3H, t, J=7 Hz), 1.7-2.1 (4H, m), 2.32 (2H, t, J=7 Hz), 2.45 (4H, d, J=7 Hz), 2.76 (2H, t, J=7 Hz), 4.11 (2H, q, J=7 Hz), 5.57 (1H, s), 6.59 (2H, d, J=9 Hz), 6.83 (1H, dt, J=1 Hz, 7 Hz), 7.0-7.35 (10H, m), 7.49 (1H, d, J=9 Hz), 7.68 (2H, d, J=9 Hz), 9.93 (1H, d, J=7 Hz)

EXAMPLE 3

A mixture of ethyl 4-[1-(4-hydroxybenzoyl)indolizin-3-yl]butyrate (334 mg), bis(4-isobutylphenyl)chloromethane (599 mg) and potassium carbonate (394 mg) in N,N-dimethylformamide (5 ml) was stirred at room temperature for 20 hours. The reaction mixture was filtered and the filtrate was poured into a mixture of ethyl acetate and 0.5N hydrochloric acid. The organic layer was separated, washed with water and brine, dried over magnesium sulfate and evaporated. The residue was chromatographed on silica gel eluting with n-hexane and ethyl acetate (3:1) to give ethyl 4-[1-[4-[bis(4-isobutylphenyl)methoxy]benzoyl]indolizin-3-yl]butyrate (95 mg) as an oil.

NMR (CDCl₁₃, δ): 0.89 (12H, d, J=7 Hz), 1.26 (3H, t, J=7 Hz), 1.74-2.15 (4H, m), 2.38-2.50 (6H, m), 2.88 (2H, t, J=7 Hz), 4.13 (2H, q, J=7 Hz), 6.28 (1H, s), 6.80-6.92 (2H, m), 6.98-7.20 (7H, m), 7.32 (4H, d, J=8 Hz), 7.77 (2H, d, J=9 Hz), 7.98 (1H, d, J=8 Hz), 8.44 (1H, d, J=9 Hz)

EXAMPLE 4

A mixture of ethyl 4-[1-(4-hydroxybenzoyl)indolizin-3-yl]butyrate (61 mg), 1-bromo-1-(4-isobutylphenyl)propane (53 mg) and potassium carbonate (72 mg) in N,N-dimethylformamide (2 ml) was stirred at room temperature for 18 hours. The reaction mixture was filtered and the filtrate was poured into a mixture of ethyl acetate and 0.5N hydrochloric acid. The organic layer was separated, washed with water and brine, dried over magnesium sulfate and evaporated. The residue was chromatographed on silica gel eluting with n-hexane and ethyl acetate (2:1) to give ethyl 4-[1-[4-[1-(4-isobutylphenyl)propyloxy]benzoyl]indolizin-3-yl]butyrate (80 mg) as an oil.

TLC Rf: 0.48 (n-hexane-ethyl acetate=2:1)

EXAMPLE 5

The following compound was obtained according to a similar manner to that of Example 3.

Ethyl 4-[1-[3-[bis(4-isobutylphenyl)methoxy]benzoyl]indolizin-3-yl]butyrate

NMR (CDCl₃, δ): 0.88 (12H, d, J=7 Hz), 1.25 (3H, t, J=7 Hz), 1.74-2.11 (4H, m), 2.33-2.49 (6H, m), 2.87 (2H, t, J=7 Hz), 4.13 (2H, q, J=7 Hz), 6.28 (1H, s), 6.76-7.47 (15H, m), 8.02 (1H, d, J=9 Hz), 8.47 (1H, d, J=9 Hz)

EXAMPLE 6

The following compound was obtained according to a similar manner to that of Example 4.

Ethyl 4-[1-[3-[1-(4-isobutylphenyl)propyloxy]benzoyl]indolizin-3-yl]butyrate

NMR (CDCl₃, δ): 0.88 (6H, d, J=7 Hz), 0.99 (3H, t, J=7 Hz), 1.25 (3H, t, J=7 Hz), 1.72-2.12 (5H, m), 2.42 (2H, t, J=7 Hz), 2.87 (2H, t, J=7 Hz), 4.13 (2H, q, J=7 Hz), 5.08 (1H, t, J=7 Hz), 6.73-7.37 (1H, m), 8.01 (1H, d, J=7 Hz), 8.46 (1H, d, J=9 Hz)

EXAMPLE 7

A mixture of ethyl 4-[3-(4-hydroxybenzoyl)indolizin-1-yl]butyrate (400 mg), bis(4-isobutylphenyl)chloromethane (430 mg) and diisopropylethylamine (736 mg) in dichloromethane (20 ml) was refluxed for 14 hours and evaporated. The residue was dissolved in ethyl acetate. The solution was washed with water and brine, dried over magnesium sulfate and evaporated. The residue was chromatographed on silica gel eluting with n-hexane and ethyl acetate (4:1) to give ethyl 4-[3-[4-[bis(4-isobutylphenyl)methoxy]benzoyl]indolizin-1-yl]butyrate (158 mg) as an oil.

NMR (CDCl₃, δ): 0.89 (12H, d, J=7 Hz), 1.22 (3H, t, J=7 Hz), 1.74-2.07 (4H, m), 2.33 (2H, t, J=7 Hz), 2.46 (4H, d, J=7 Hz), 2.77 (2H, t, J=7 Hz), 4.11 (2H, q, J=7 Hz), 6.27 (1H, s), 6.82-7.20 (9H, m), 7.33 (1H, d, J=9 Hz), 7.52 (1H, d, J=9 Hz), 7.72 (1H, d, J=9 Hz)

EXAMPLE 8

The following compound was obtained according to a similar manner to that of Example 7.

Ethyl 4-[3-[3-[bis(4-isobutylphenyl)methoxy]benzoyl]indolizin-1-yl]butyrate

NMR (CDCl₃, δ): 0.88 (12H, d, J=7 Hz), 1.23 (3H, t, J=7 Hz), 1.73-2.06 (4H, m), 2.33 (2H, t, J=7 Hz), 2.45 (4H, d, J=7 Hz), 2.76 (2H, t, J=7 Hz), 4.11 (2H, q, J=7 Hz), 6.28 (1H, s), 6.86-6.96 (1H, m), 7.05-7.43 (14H, m), 7.55 (1H, d, J=9 Hz), 9.93 (1H, d, J=7 Hz)

EXAMPLE 9

To a solution of ethyl 4-[1-[3-[bis(4-isobutylphenyl)methylamino]benzoyl]indolizin-3-yl]-butyrate (279 mg) in ethanol (10 ml) was added 4N sodium hydroxide (0.44 ml). Stirring was continued for 1 hour at 40° C. The reaction mixture was evaporated in vacuo, then added a solution of potassium dihydrogen phosphate (300 mg) in water and 1N hydrochloric acid (26 ml), and extracted with ethyl acetate. The combined organic layers were dried over sodium sulfate. After evaporation of the solvent, the residue was chromatographed on silica gel eluting with ethyl acetate to give 4-[1-[3-[bis(4-isobutylphenyl)methylamino]benzoyl]indolizin-3-yl]butyric acid (229 mg).

NMR (CDCl₃, δ): 0.87 (12H, d, J=7 Hz), 1.83 (2H, m), 2.22 (2H, m), 2.4-2.5 (6H, m), 2.85, t, J=7 Hz), 5.51 (1H, s), 6.69 (1H, m), 6.82 (1H, s), 6.84 (1H, dt, J=1 Hz, 7 Hz), 7.0-7.3 (12H, m), 7.94 (1H, d, J=7 Hz), 8.46 (1H, d, J=9 Hz)

EXAMPLE 10

The following compounds were obtained according to a similar manner to that of Example 9.

(1) 4-[1-[4-[Bis(4-isobutylphenyl)methylamino)benzoyl]indolizin-3-yl]butyric acid NMR (CDCl₃, δ): 0.88 (12H, d, J=7 Hz), 1.84 (1H, m), 2.06 (2H, m), 2.4-2.55 (6H, m), 2.88 (2H, t, J=7 Hz), 5.56 (1H, s), 6.57 (2H, d, J=9 Hz), 6.80 (1H, dt, J=1 Hz, 7 Hz), 6.92 (1H, s), 7.08 (1H, m), 7.11 (4H, d, J=8 Hz), 7.23 (4H, d, J=8 Hz), 7.72 (2H, d, J=9 Hz), 7.92 (1H, d, J=7 Hz), 8.41 (1H, d, J=8 Hz)

(2) 4-[3-[3-[Bis(4-isobutylphenyl)methylamino]-benzoyl]indolizin-1-yl]butyric acid NMR (CDCl$_3$, δ): 0.86 (12H, d, J=7 Hz), 1.7–2.05 (4H, m), 2.38 (2H, t, J=7 Hz), 2.43 (4H, d, J=7 Hz), 2.76 (2H, t, J=7 Hz), 5.52 (1H, s), 6.71 (1H, m), 6.88 (1H, dt, J=1 Hz, 7 Hz), 7.0–7.3 (13H, m), 7.49 (1H, dt, J=8 Hz, 1 Hz), 9.91 (1H, d, J=7 Hz)

(3) 4-[3-[4-[Bis(4-isobutylphenyl)methylamino]benzoyl]indolizin-1-yl]butyric acid NMR (CDCl$_3$, δ): 0.88 (12H, d, J=7 Hz), 1.7–2.1 (4H, m), 2.39 (2H, t, J=7 Hz), 2.45 (4H, d, J=7 Hz), 2.79 (2H, t, J=7 Hz), 5.57 (1H, s), 6.58 (2H, d, J=9 Hz), 6.82 (1H, dt, J=1 Hz, 7 Hz), 7.0–7.3 (10H, m), 7.49 (1H, d, J=9 Hz), 7.68 (2H, d, J=7 Hz), 9.93 (1H, d, J=7 Hz)

EXAMPLE 11

To a solution of ethyl 4-[1-[bis(4-isobutylphenyl)methoxy]benzoyl]indolizin-3-yl]butyrate (90 mg) in ethanol (1 ml) and 1,4-dioxane (1 ml) was added 1N aqueous solution of sodium hydroxide (0.5 ml). The mixture was stirred at room temperature for 2 hours and then poured into a mixture of ethyl acetate and 0.5N hydrochloric acid. The organic layer was separated, washed with water and brine, dried over magnesium sulfate and evaporated to give 4-[1-[4-[bis(4-isobutylphenyl)methoxy]benzoyl]-indolizin-3-yl]butyric acid (79 mg) as powder.

NMR (CDCl$_3$, δ): 0.89 (12H, d, J=7 Hz), 1.73–1.97 (2H, m), 1.99–2.16 (2H, m), 2.40–2.55 (6H, m), 2.89 (2H, m), 6.27 (1H, s), 6.79–6.90 (2H, m), 6.98–7.18 (7H, m), 7.28–7.38 (4H, m), 7.75 (2H, d, J=9 Hz), 7.96 (1H, d, J=7 Hz), 8.43 (1H, d, J=9 Hz)

EXAMPLE 12

The following compounds were obtained according to a similar manner to that of Example 11.

(1) 4-[1-[4-[1-(4-Isobutylphenyl)propyloxy]benzoyl]indolizin- 3-yl]butyric acid

NMR (CDCl$_3$, δ): 0.88 (6H, d, J=7 Hz), 1.01 (3H, t, J=7 Hz), 1.72–2.17 (5H, m), 2.40–2.55 (4H, m), 2.88 (2H, t, J=7 Hz), 5.08 (1H, t, J=7 Hz), 6.79–6.98 (4H, m), 7.07–7.32 (5H, m), 7.73 (2H, d, J=9 Hz), 7.94 (1H, d, J=7 Hz), 8.42 (1H, d, J=9 Hz)

(2) 4-[1- [3-[Bis(4-isobutylphenyl)methoxy]benzoyl]indolizin-3-yl]butyric acid

NMR (CDCl$_3$, δ): 0.88 (12H, d, J=7 Hz), 1.76–1.92 (2H, m), 1.99–2.13 (2H, m), 2.40–2.55 (6H, m), 2.88 (2H, t, J=7 Hz), 6.27 (1H, s), 6.76–7.46 (15H, m), 7.98 (1H, d, J=7 Hz), 8.46 (1H, d, J=9 Hz)

(3) 4-[1-[3-[1-(4-Isobutylphenyl)propyloxy]benzoyl]indolizin-3-yl]butyric acid

NMR (CDCl$_3$, δ): 0.88 (6H, d, J=7 Hz), 0.99 (3H, t, J=7 Hz), 1.70–2.14 (5H, m), 2.37–2.56 (4H, m), 2.88 (2H, t, J=7 Hz), 5.08 (1H, t, J=7 Hz), 6.76–7.38 (11H, m), 7.97 (1H, d, J=7 Hz), 8.47 (1H, d, J=9 Hz)

(4) 4-[3- [4-Bis(4-isobutylphenyl)methoxy]benzoyl]indolizin-1-yl]butyric acid

NMR (CDCl$_3$, δ): 0.88 (12H, d, J=7 Hz), 1.73–2.08 (4H, m), 2.35–2.50 (6H, m), 2.80 (2H, t, J=7 Hz), 6.27 (1H, s), 6.81–7.22 (9H, m), 7.32 (4H, d, J=8 Hz), 7.51 (1H, d, J=9 Hz), 7.71 (2H, d, J=9 Hz)

(5) 4-[3- [3-[Bis(4-isobutylphenyl)methoxy]benzoyl]indolizin-1-yl]butyric acid

NMR (CDCl$_3$, δ): 0.88 (12H, d, J=7 Hz), 1.72–2.05 (4H, m), 2.33–2.48 (6H, m), 2.78 (2H, t, J=7 Hz), 6.27 (1H, s), 6.84–6.96 (9H, m), 7.04–7.42 (14H, m)

EXAMPLE 13

4N-Hydrogen chloride in ethyl acetate (0.5 ml) was added to a solution of 4-[1-[3-[bis(4-isobutylphenyl)methylamino]benzoyl]indolizin-3-yl]butyric acid (0.60 g) in ethyl acetate (5 ml). After the solution was left in a refrigerator for 16 hours, the resulting crystal was collected by filtration to give 4-[1-[3-[bis(4-isobutylphenyl)methylamino]benzoyl]indolizin-3-yl]butyric acid hydrochloride as yellow powder (0.62 g).

mp: 136°–138° C. (dec.)

NMR (DMSO-d$_6$, δ): 8.40 (1H, d, J=7 Hz), 8.30 (1H, d, J=9 Hz), 7.35 (2H, d, J=9 Hz), 7.10 (2H, d, J=9 Hz), 6.9–7.4 (6H, m), 6.72 (1H, s), 5.67 (1H, s), 2.88 (2H, t, J=7 Hz), 2.40 (4H, d, J=7 Hz), 2.33 (2H, t, J=7 Hz), 1.7–2.0 (4H, m), 0.82 (12H, d, J=7 Hz)

EXAMPLE 14

To a solution of 4-[1-[3-[bis(4-isobutylphenyl)methylamino]benzoyl]indolizin-3-yl]butyric acid (244 mg) in ethanol was added 1N sodium hydroxide. After removal of the solvent, the residue was dissolved in benzene, filtered through a cotton filter, and evaporated in vacuo to give sodium 4-[1-[3-[bis(4-isobutylphenyl)methylamino]benzoyl]indolizin-3-yl]butyrate (240 mg).

NMR (CD$_3$OD, δ): 0.88 (12H, d, J=7 Hz), 1.82 (2H, m), 1.97 (2H, m), 2.31 (2H, t, J=7 Hz), 2.44 (4H, d, J=7 Hz), 2.88 (2H, t, J=7 Hz), 5.56 (1H, s), 6.74 (1H, s), 6.81 (1H, m), 6.9–7.3 (5H, m), 7.08 (4H, d, J=8 Hz), 7.28 (1H, d, J=7 Hz), 8.25–8.35 (2H, m)

EXAMPLE 15

The following compounds were obtained according to a similar manner to that of Example 1.

(1) Ethyl 4-[3-[4-[bis(4-isobutylphenyl)methylamino]benzoyl]-2-methylindolizin-1-yl]butyrate NMR (CDCl$_3$, δ): 0.88 (12H, d, J=7 Hz), 1.23 (3H, t, J=7 Hz), 1.75–2.0 (4H, m), 2.00 (3H, s), 2.32 (2H, t, J=7 Hz), 2.46 (4H, d, J=7 Hz), 2.72 (2H, t, J=7 Hz), 4.11 (2H, q, J=7 Hz), 5.57 (1H, s), 6.55 (2H, d, J=8 Hz), 6.65 (1H, dt, J=1 Hz, 7 Hz), 6.98 (1H, m), 7.11 (4H, d, J=8 Hz), 7.24 (1H, d, J=8 Hz), 7.38 (1H, d, J=8 Hz), 7.49 (2H, d, J=8 Hz), 9.30 (1H, d, J=7 Hz)

(2) Ethyl 4-[3-[3-[bis(4-isobutylphenyl)methylamino]benzoyl]-2-methylindolizin-1-yl]butyrate NMR (CDCl$_3$, δ): 0.88 (12H, d, J=7 Hz), 1.23 (3H, t, J=7 Hz), 1.76 (3H, s), 1.83 (2H, m), 2.31 (2H, t, J=7 Hz), 2.42 (4H, d, J=7 Hz), 2.68 (2H, t, J=7 Hz), 4.12 (2H, q, J=7 Hz), 5.51 (1H, s), 6.65–6.95 (4H, m), 7.08 (4H, d, J=8 Hz), 7.0–7.3 (2H, m), 7.23 (4H, d, J=8 Hz), 7.42 (1H, d, J=9 Hz), 9.66 (1H, d, J=7 Hz)

(3) Ethyl 4-[1-[4-[bis(4-isobutylphenyl)methylamino]benzoyl]-2-methylindolizin-3-yl]butyrate NMR (CDCl$_3$, δ): 0.88 (12H, d, J=7 Hz), 1.25 (3H, t, J=7 Hz), 1.87 (4H, m), 2.27 (3H, s), 2.38 (2H, t, J=7 Hz), 2.45 (4H, d, J=7 Hz), 2.92 (2H, t, J=7 Hz), 4.14 (2H, q, J=7 Hz), 5.56 (1H, s), 6.52 (2H, d, J=9 Hz), 6.66 (1H, dt, J=1 Hz, 7 Hz), 6.80 (1H, m), 7.10 (4H, d, J=8 Hz), 7.22 (4H, d, J=8 Hz), 7.46 (1H, d, J=9 Hz), 7.59 (2H, d, J=8 Hz), 7.93 (1H, d, J=7 Hz)

(4) Ethyl 4-[1-[3-[bis(4-isobutylphenyl)methylamino]benzoyl]-2-methylindolizin-3-yl]butyrate NMR (CDCl$_3$, δ): 0.88 (12H, d, J=7 Hz), 1.27 (3H, t, J=7 Hz), 1.7–2.0 (4H, m), 2.20 (3H, s), 2.38 (2H, t, J=7 Hz), 2.43 (4H, d, J=7 Hz), 2.90 (2H, t, J=7 Hz), 4.14 (2H, q, J=7 Hz), 5.51 (1H, s), 6.63–6.78 (2H, m), 6.8–7.0 (2H, m), 7.05–7.3 (10H, m), 7.44 (1H, d, J=8 Hz), 7.97 (1H, d, J=7 Hz)

EXAMPLE 16

The following compounds were obtained according to a similar manner to that of Example 4.

(1) Ethyl 4-[1-[4-[1-(4-isobutylphenyl)hexyloxy]benzoyl]indolizin-3-yl]butyrate

NMR (CDCl$_3$, δ): 0.80–0.95 (9H, m), 1.26–1.65 (9H, m), 1.70–2.15 (4H, m), 2.35–2.50 (4H, m), 2.87 (2H, t, J=7 Hz), 4.13 (2H, q, J=7 Hz), 5.15 (1H, dd, J=2 Hz, 7 Hz), 6.80–6.97 (4H, m), 7.07–7.31 (5H, m), 7.72 (2H, d, J=9 Hz), 7.98 (1H, d, J=7 Hz), 8.43 (1H, d, J=9 Hz)

(2) Ethyl 4-[3-[4-[1-(4-isobutylphenyl)hexyloxy]benzoyl]indolizin-1-yl]butyrate

NMR (CDCl$_3$, δ): 0.80–0.95 (9H, m), 1.17–1.63 (9H, m), 1.72–2.12 (5H, m), 2.32 (2H, t, J=7 Hz), 2.46 (2H, d, J=7 Hz), 2.76 (2H, t, J=7 Hz), 4.10 (2H, q, J=7 Hz), 5.14 (1H, dd, J=1.5 Hz, 7 Hz), 6.81–6.98 (3H, m), 7.06–7.19 (4H, m), 7.27 (2H, d, J=9 Hz), 7.51 (1H, d, J=9 Hz), 7.68 (2H, d, J=9 Hz), 9.87 (1H, d, J=7 Hz)

(3) Ethyl 4-[1-[4-(1-(4-isobutylphenyl)octyloxy]benzoyl]-indolizin-3-yl]butyrate NMR (CDCl$_3$, δ): 0.8–0.95 (9H, m), 1.15–1.65 (13H, m), 1.7–2.15 (5H, m), 2.35–2.5 (4H, m), 2.88 (2H, t, J=7.5 Hz), 4.12 (2H, q, J=7 Hz), 5.15 (1H, dd, J=2 Hz, 7 Hz), 6.8–6.95 (4H, m), 7.05–7.3 (5H, m), 7.73 (2H, d, J=9 Hz), 7.98 (1H, d, J=7 Hz), 8.44 (1H, d, J=9 Hz)

(4) Ethyl 4-[1-[4-[1-(4-isobutylphenyl)heptyloxy]benzoyl]indolizin-3-yl]butyrate NMR (CDCl$_3$, δ): 0.8–1.0 (9H, m), 1.2–1.65 (11H, m), 1.7–2.15 (5H, m), 2.35–2.5 (4H, m), 2.88 (2H, t, J=7.5 Hz), 4.12 (2H, q, J=7 Hz), 5.15 (1H, dd, J=2 Hz, 7 Hz), 6.8–6.95 (4H, m), 7.05–7.3 (5H, m), 7.74 (2H, d, J=9 Hz), 7.98 (1H, d, J=7 Hz), 8.43 (1H, d, J=9 Hz)

(5) Ethyl 4-[1-[4-[1-(4-isobutylphenyl)pentyloxy]benzoyl]indolizin-3-yl]butyrate NMR (CDCl$_3$, δ): 0.8–1.0 (9H, m), 1.2–1.65 (7H, m), 1.7–2.15 (5H, m), 2.35–2.5 (4H, m), 2.88 (2H, t, J=7.5 Hz), 4.12 (2H, q, J=7 Hz), 5.15 (1H, dd, J=2 Hz, 7 Hz), 6.8–6.95 (4H, m), 7.05–7.3 (5H, m), 7.73 (2H, d, J=9 Hz), 7.99 (1H, d, J=7 Hz), 8.44 (2H, d, J=9 Hz)

(6) Ethyl 4-[1-[4-[1-(4-isobutylphenyl)butyloxy]benzoyl]indolizin-3-yl]butyrate

NMR (CDCl$_3$, δ): 0.8–1.05 (9H, m), 1.24 (3H, t, J=7 Hz), 1.3–1.65 (2H, m), 1.7–2.15 (5H, m), 2.35–2.5 (4H, m), 2.87 (2H, t, J=7.5 Hz), 4.12 (2H, q, J=7 Hz), 5.17 (1H, dd, J=2 Hz, 7 Hz), 6.8–6.95 (4H, m), 7.05–7.3 (5H, m), 7.72 (2H, d, J=9 Hz), 7.98 (1H, d, J=7 Hz), 8.44 (1H, d, J=9 Hz)

EXAMPLE 17

A mixture of ethyl 4-[1-(3-aminobenzoyl)indolizin-3-yl]butyrate (175 mg), 1-bromohexyl-4-isobutylbenzene (177 mg) and diisopropylethylamine (194 mg) in dichloromethane (3 ml) was refluxed for 20 hours. The reaction mixture was poured into a mixture of ethyl acetate and water. The organic layer was separated and washed with water and brine, dried over magnesium sulfate and evaporated. The residue was chromatographed on silica gel column eluting with n-hexane and ethyl acetate (3:1) to give ethyl 4-[1-[3-[1-(4-isobutylphenyl)hexylamino]-benzoyl]indolizin-3-yl]butyrate (170 mg) as an oil.

NMR (CDCl$_3$, δ): 0.80–0.95 (9H, m), 1.27–1.50 (9H, m), 1.68–2.12 (5H, m), 2.34–2.48 (4H, m), 2.85 (2H, t, J=7.5 Hz), 4.12 (2H, q, J=7 Hz), 4.33 (1H, t, J=7 Hz), 6.63 (1H, d, J=7.5 Hz), 6.80–6.91 (2H, m), 6.94–7.28 (9H, m), 7.98 (1H, d, J=7 Hz), 8.46 (1H, d, J=9 Hz)

EXAMPLE 18

The following compounds were obtained according to a similar manner to that of Example 17.

(1) Ethyl 4-[3-[3-[1-(4-isobutylphenyl)hexylamino]-benzoyl]indolizin-1-yl]butyrate NMR (CDCl$_3$, δ): 0.78–0.96 (9H, m), 1.20–1.50 (9H, m), 1.64–2.07 (5H, m), 2.25–2.48 (4H, m), 2.75 (2H, t, J=7.5 Hz), 4.11 (2H, q, J=7 Hz), 4.33 (1H, t, J=7 Hz), 6.64 (1H, d, J=7.5 Hz), 6.83–7.30 (11H, m), 7.52 (1H, d, J=9 Hz)

Ethyl 4-[1-[3-[1-(4-isobutylphenyl)butylamino]benzoyl]indolizin-3-yl]butyrate

NMR (CDCl$_3$, δ): 0.8–1.0 (9H, m), 1.2–1.55 (5H, m), 1.7–2.15 (5H, m), 2.35–2.55 (4H, m), 2.87 (2H, t, J=7.5 Hz), 4.13 (2H, q, J=7 Hz), 4.36 (1H, t, J=7 Hz), 6.64 (1H, d, J=8 Hz), 6.8–6.95 (2H, m), 7.0–7.35 (9H, m), 7.98 (1H, d, J=7 Hz), 8.45 (1H, d, J=9 Hz)

EXAMPLE 19

The following compounds were obtained according to similar manner to that of Example 11.

(1) 4-[3- [4-[1-(4-Isobutylphenyl)hexyloxy]benzoyl]indolizin-1-yl]butyric acid

NMR (CDCl$_3$, δ): 0.81–0.96 (9H, m), 1.20–1.62 (6H, m), 1.72–2.15 (5H, m), 2.34–2.49 (4H, m), 2.79 (2H, t, J=7 Hz), 5.14 (1H, dd, J=1.5 Hz, 7 Hz), 6.80–6.97 (3H, m), 7.06–7.18 (4H, m), 7.26 (2H, d, J=9 Hz), 7.50 (1H, d, J=9 Hz), 7.68 (2H, d, J=9 Hz), 9.87 (1H, d, J=7 Hz)

(2) 4-[1- [4-[1-(4-Isobutylphenyl)hexyloxy]benzoyl]indolizin-3-yl]butyric acid

NMR (CDCl$_3$, δ): 0.82–0.95 (9H, m), 1.23–1.65 (6H, m), 1.70–2.15 (5H, m), 2.38–2.55 (4H, m), 2.88 (2H, t, J=7 Hz), 5.14 (1H, dd, J=2 Hz, 7 Hz), 6.78–6.97 (4H, m), 7.05–7.30 (5H, m), 7.72 (2H, d, J=9 Hz), 7.94 (1H, d, J=7 Hz), 8.43 (1H, d, J=9 Hz)

(3) 4-[1-[4-[1-(4-Isobutylphenyl)octyloxy]benzoyl]indolizin-3-yl]butyric acid

NMR (CDCl$_3$, δ): 0.8–0.95 (9H, m), 1.15–1.65 (10H, m), 1.7–2.2 (5H, m), 2.4–2.55 (4H, m), 2.89 (2H, t, J=7.5 Hz), 5.15 (1H, dd, J=2 Hz, 7 Hz), 6.8–6.95 (4H, m), 7.05–7.3 (5H, m), 7.72 (2H, d, J=9 Hz), 7.96 (1H, d, J=7 Hz), 8.43 (1H, d, J=9 Hz)

(4) 4-[1-[4-[1-(4-Isobutylphenyl)heptyloxy]benzoyl]indolizin-3-yl]butyric acid

NMR (CDCl$_3$, δ): 0.8–1.0 (9H, m), 1.2–1.65 (8H, m), 1.7–2.15 (5H, m), 2.4–2.55 (4H, m), 2.89 (2H, t, J=7.5 Hz), 5.15 (1H, dd, J=2 Hz, 7 Hz), 6.8–6.95 (4H, m), 7.05–7.3 (5H, m), 7.73 (2H, d, J=9 Hz), 7.95 (1H, d, J=7 Hz), 8.43 (1H, d, J=9 Hz)

(5) 4-[1-[4-[1-(4 -Isobutylphenyl)pentyloxy]benzoyl]indolizin-3-yl]butyric acid

NMR (CDCl$_3$, δ): 0.8–1.0 (9H, m), 1.25–1.6 (4H, 1.7–2.15 (5H, m), 2.4–2.55 (4H, m), 2.88 (2H, t, J=7.5 Hz), 5.14 (1H, dd, J=2 Hz, 7 Hz), 6.8–6.95 (4H, m), 7.05–7.3 (5H, m), 7.73 (2H, d, J=9 Hz), 7.96 (1H, d, J=7 Hz), 8.43 (1H, d, J=9 Hz)

(6) 4-[1-[4-[1-(4-Isobutylphenyl)butoxy]benzoyl]indolizin-3-yl]butyric acid

NMR (CDCl$_3$, δ): 0.8–1.05 (9H, m), 1.3–1.65 (2H, m), 1.7–2.15 (5H, m), 2.4–2.55 (4H, m), 2.88 (2H, t, J=7.5 Hz), 5.16 (1H, dd, J=7 Hz), 6.8–6.95 (4H, m), 7.05–7.3 (5H, m), 7.72 (2H, d, J=9 Hz), 7.96 (1H, d, J=7 Hz), 8.42 (1H, d, J=9 Hz)

EXAMPLE 20

To a solution of ethyl 4-[3-[3-[1-(4-isobutylphenyl)-hexylamino]benzoyl]indolizin-1-yl]butyrate (117 mg) in ethanol (2 ml) and 1,4-dioxane (2 ml) was added 1N aqueous solution of sodium hydroxide (1 ml). The mixture was stirred at room temperature for 3 hours, and then poured into a mixture of ethyl acetate and 0.5N hydrochloric acid. The organic layer was separated, washed with water and brine, dried over magnesium sulfate and evaporated to give 4-[3-[3-[1-(4-isobutylphenyl)hexylamino]benzoyl]indolizin-1-yl]butyric acid (98 mg) as powder.

NMR (CDCl$_3$, δ): 0.78–0.96 (9H, m), 1.15–1.50 (6H, m), 1.68–2.07 (5H, m), 2.32–2.48 (4H, m), 2.77 (2H, t, J=7.5 Hz), 4.32 (1H, t, J=7 Hz), 6.64 (1H, d, J=7.5 Hz), 6.82–7.28 (11H, m), 7.50 (1H, d, J=9 Hz)

EXAMPLE 21

The following compounds were obtained according to a similar manner to that of Example 20.

(1) 4-[1- [3-[1-(4-Isobutylphenyl)hexylamino]benzoyl]indolizin-3-yl]butyric acid NMR (CDCl$_3$, δ): 0.78–0.93 (9H, m), 1.15–1.50 (6H, m), 1.63–2.13 (5H, m), 2.37–2.53 (4H, m), 2.87 (2H, t, J=7.5 Hz), 4.32 (1H, t, J=7 Hz), 6.62 (1H, d, J=7.5 Hz), 6.79–6.90 (2H, m), 6.94–7.27 (9H, m), 7.95 (2H, d, J=7 Hz), 8.45 (1H, d, J=9 Hz)

(2) 4- [1-[3-[1-(4-Isobutylphenyl)butylamino]benzoyl]indolizin-3-yl]butyric acid NMR (CDCl$_3$, δ): 0.8–1.0 (9H, m), 1.2–1.5 (2H, m), 1.65–2.15 (5H, m), 2.35–2.5 (4H, m), 2.86 (2H, t, J=7.5 Hz), 4.34 (1H, t, J=7 Hz), 6.64 (1H, d, J=8 Hz), 6.8–6.95 (2H, m), 7.0–7.3 (9H, m), 7.95 (1H, d, J=7 Hz), 8.44 (1H, d, J=9 Hz)

EXAMPLE 22

The following compounds were obtained according to a similar manner to that of Example 9.

(1) 4-[3-[4-[Bis(4-isobutylphenyl)methylamino]benzoyl]-2-methylindolizin-1-yl]butyric acid NMR (CDCl$_3$, δ): 0.88 (12H, d, J=7 Hz), 1.7–2.0 (4H, m), 2.01 (3H, s), 2.39 (2H, t, J=7 Hz), 2.46 (4H, d, J=7 Hz), 2.74 (2H, t, J=7 Hz), 5.57 (1H, s), 6.53 (2H, d, J=8 Hz), 6.64 (1H, dt, J=1 Hz, 7 Hz), 6.95 (1H, m), 7.11 (4H, d, J=8 Hz), 7.22 (4H, d, J=8 Hz), 7.37 (1H, d, J=9 Hz), 7.50 (2H, d, J=8 Hz), 9.30 (1H, d, J=7 Hz)

(2) 4-[3-[3-[Bis(4-isobutylphenyl)methylamino]benzoyl]-2-methylindolizin-1-yl]butyric acid NMR (CDCl$_3$, δ): 0.88 (12H, d, J=7 Hz), 1.74 (3H, s), 1.75–1.95 (2H, m), 2.37 (2H, t, J=7 Hz), 2.42 (4H, d, J=7 Hz), 2.69 (2H, t, J=7 Hz), 5.51 (1H, s), 6.6–6.8 (3H, m), 6.88 (1H, d, J=7 Hz), 7.07 (4H, d, J=7 Hz), 7.0–7.3 (2H, m), 7.23 (4H, d, J=7 Hz), 7.40 (1H, d, J=8 Hz), 9.67 (1H, d, J=7 Hz)

(3) 4- [1- [4- [Bis (4-isobutylphenyl)methylamino]benzoyl]-2-methylindolizin-3-yl]butyric acid NMR (CDCl$_3$, δ): 0.88 (12H, t, J=7 Hz), 1.7–2.0 (4H, m), 2.38 (3H, s), 2.42 (2H, t, J=7 Hz), 2.44 (4H, d, J=7 Hz), 2.93 (2H, t, J=7 Hz), 5.56 (1H, s), 6.52 (2H, d, J=9 Hz), 6.64 (1H, dt, J=7 Hz), 6.81 (1H, m), 7.09 (4H, d, J=8 Hz), 7.25 (4H, d, J=7 Hz), 7.45 (1H, d, J=8 Hz), 7.58 (2H, d, J=9 Hz), 7.90 (1H, d, J=7 Hz)

(4) 4-[1-[3-[Bis(4-isobutylphenyl)methylamino]benzoyl]-2-methylindolizin-3-yl]butyric acid NMR (CDCl$_3$, δ): 0.88 (12H, d, J=7 Hz), 1.7–2.0 (4H, m), 2.18 (3H, s), 2.42 (4H, d, J=7 Hz), 2.45 (2H, t, J=7 Hz), 2.91 (2H, t, J=7 Hz), 5.50 (1H, s), 6.6–7.3 (6H, m), 7.06 (4H, d, J=8 Hz), 7.22 (4H, d, J=8 Hz), 7.45 (1H, d, J=8 Hz), 7.92 (1H, d, J=7 Hz)

EXAMPLE 23

To a mixture of ethyl 4-[1-(4-hydroxybenzoyl)indolizin- 3-yl]butyrate (392 mg), (R)-1-(4-isobutylphenyl)butan-1-ol (230 mg) and triphenylphosphine (292 mg) in tetrahydrofuran (3 ml) and toluene (15 ml) was added diethyl azodicarboxylate (0.178 ml) at −20° C. under nitrogen atmosphere. After the mixture was stirred at −20° C. under nitrogen for 2.5 hours, acetic acid (0.05 ml) was added and the mixture was warmed up to room temperature. The solvent was evaporated under reduced pressure and the residue was poured into a mixture of ethyl acetate and water. The organic phase was separated, washed with water and brine, dried over magnesium sulfate and evaporated. The residue was chromatographed on silica gel column eluting with a mixture of n-hexane and ethyl acetate (4:1) to give ethyl 4-[1-[4-[(S)-1-(4-isobutylphenyl)butoxy]benzoyl]indolizin-3-yl]butyrate (295 mg) as an oil.

NMR (CDCl$_3$, δ): 0.8–1.05 (9H, m), 1.24 (3H, t, J=7 Hz), 1.3–1.65 (2H, m), 1.7–2.15 (5H, m), 2.35–2.5 (4H, m), 2.87 (2H, t, J=7.5 Hz), 4.12 (2H, q, J=7 Hz), 5.17 (1H, dd, J=2 Hz, 7 Hz), 6.8–6.95 (4H, m), 7.05–7.3 (5H, m), 7.72 (2H, d, J=9 Hz), 7.98 (1H, d, J=7 Hz), 8.44 (1H, d, J=9 Hz)

EXAMPLE 24

To a solution of ethyl 4-[1-[4-[(S)-1-(4-isobutylphenyl)butoxy]benzoyl]indolizin-3-yl]butyrate (282 mg) in ethanol (3 ml) and 1,4-dioxane (3 ml) was added 1N aqueous solution of sodium hydroxide (2 ml). The mixture was stirred at room temperature for 2 hours, and then poured into a mixture of ethyl acetate and 0.5N hydrochloric acid. The organic layer was separated, washed with water and brine, dried over magnesium sulfate and evaporated to give 4-[1-[4-[(S)-1-(4-isobutylphenyl)butoxy]benzoyl]- indolizin-3-yl]butyric acid (232 mg) as powder.

NMR (CDCl$_3$, δ): 0.8–1.05 (9H, m), 1.3–1.65 (2H, m), 1.7–2.15 (5H, m), 2.4–2.55 (4H, m), 2.88 (2H, t, J=7.5 Hz), 5.16 (1H, dd, J=7 Hz), 6.8–6.95 (4H, m), 7.05–7.3 (5H, m), 7.72 (2H, d, J=9 Hz), 7.96 (1H, d, J=7 Hz), 8.42 (1H, d, J=9 Hz)

$[\alpha]_D^{25} = -78.3°$ (C=0.5, CHCl$_3$)

EXAMPLE 25

The following compound was obtained according to a similar manner to that of Example 23.

Ethyl 4-[1-[4-[(R)-i-(4-isobutylphenyl)butoxy]benzoyl]indolizin-3-yl]butyrate

NMR (CDCl$_3$, δ): 0.8–1.05 (9H, m), 1.24 (3H, t, J=7 Hz·), 1.3–1.65 (2H, m), 1.7–2.15 (5H, m), 2.35–2.5 (4H, m), 2.87 (2H, t, J=7.5 Hz), 4.12 (2H, q, J=7 Hz), 5.17 (1H, dd, J=2 Hz, 7 Hz), 6.8–6.95 (4H, m), 7.05–7.3 (5H, m), 7.72 (2H, d, J=9 Hz), 7.98 (1H, d, J=7 Hz), 8.44 (1H, d, J=9 Hz)

EXAMPLE 26

The following compound was obtained according to a similar manner to that of Example 24.

4-[1-[4-[(R)-1-(4-Isobutylphenyl)butoxy]benzoyl]indolizin-3-yl]butyric acid

NMR (CDCl$_3$, δ): 0.8–1.05 (9H, m), 1.3–1.65 (2H, 1.7–2.15 (5H, m), 2.4–2.55 (4H, m), 2.88 (2H, J=7.5 Hz), 5.16 (1H, dd, J=7 Hz), 6.8–6.95 (4H, m), 7.05–7.3 (5H, m), 7.72 (2H, d, J=9 Hz), 7.96 (1H, d, J=7 Hz), 8.42 (1H, d, J=9 Hz)

$[\alpha]_D^{25} = +79.8°$ (C=0.5, CHCl$_3$)

EXAMPLE 27

To a solution of ethyl 4- [1- [3- [(1-carboxyethyl)amino]benzoyl]indolizin-3-yl]butyrate (60 mg), heptylamine (16 mg) and 1-hydroxybenzotriazole (20 mg) in dichloromethane (3 ml) was added 1-(3-dimethylaminopropyl)-3-ethylcarbodiimide hydrochloride (30 mg). The mixture was stirred for 3 hours at room temperature, evaporated and dissolved in ethyl acetate (10 ml). The solution was washed with diluted hydrochloric acid and water and dried over magnesium sulfate. The solvent was removed under reduced pressure to give ethyl 4-[1-[3-[[1(heptylcarbamoyl)ethyl]amino]-benzoyl]indolizin-3-yl]butyrate (70 mg) as a yellow oil.

NMR (CDCl$_3$, δ): 0.84 (3H, m), 1.1–1.4 (11H, m), 1.45 (2H, m), 1.54 (3H, d, J=7 Hz), 2.05 (2H, m), 2.43 (2H, t, J=7 Hz), 2.88 (2H, t, J=7 Hz), 3.23 (2H, q, J=7 Hz), 3.90 (1H, q, J=7 Hz), 4.12 (2H, q, J=7 Hz), 6.75 (1H, m), 6.88 (1H, s), 6.93 (1H, m), 7.1–7.3 (3H, m), 7.45 (1H, m), 7.7–7.9 (1H, m), 8.03 (1H, d, J=7 Hz), 8.49 (1H, d, J=9 Hz)

EXAMPLE 28

The following compounds were obtained according to a similar manner to that of Example 27.

(1) Ethyl 4-[1-[3-[(butylcarbamoyl)(4-isobutylphenyl)methyl]amino]benzoyl]indolizin-3-yl]butyrate NMR (CDCl3, δ): 0.8–1.0 (9H, m), 1.1–1.3 (5H, m), 1.43 (2H, m), 1.82 (1H, m), 2.05 (2H, m), 2.3–2.6 (4H, m), 2.87 (2H, t, J=7 Hz), 3.25 (2H, m), 4.11 (2H, q, J=7 Hz), 4.88 (1H, s), 6.7–7.0 (3H, m), 7.1–7.4 (8H, m), 8.01 (1H, d, J=7 Hz), 8.48 (1H, d, J=9 Hz)

(2) Ethyl 4-[1-[3-[(hepthylcarbamoyl)(4-isobutylphenyl)methyl]amino]benzoyl]indolizin-3-yl]butyrate NMR (CDCl$_3$, δ): 0.8–1.0 (9H, m), 1.1–1.3 (11H, m), 1.45 (2H, m), 1.85(1H, m), 2.0–2.2 (2H, m), 2.4–2.6 (4H, m), 2.88 (2H, t, J=7 Hz), 3.26 (2H, m), 4.12 (2H, q, J=7 Hz), 4.70 (1H, s), 6.6–7.0 (3H, m), 7.1–7.3 (6H, m), 7.35 (2H, d, J=9 Hz), 8.00 (1H, d, J=7 Hz), 8.47 (1H, d, J=9 Hz)

(3) Ethyl 4-[1-[3-[[N-(4-isobutylphenyl)carbamoyl]methylamino]benzoyl]indolizin-3-yl]butyrate NMR (CDCl$_3$, δ): 0.87 (6H, d, J=7 Hz), 1.25 (3H, t, J=7 Hz), 1.7–2.1 (3H, m), 2.3–2.5 (4H, m), 2.82 (2H, t, J=7 Hz), 3.95 (2H, s), 4.11 (2H, q, J=7 Hz), 6.7–7.0 (3H, m), 7.09 (2H, d, J=9 Hz), 7.1–7.4 (4H, m), 7.45 (2H, d, J=9 Hz), 8.02 (1H, d, J=7 Hz), 8.50 (1H, d, J=9 Hz), 8.58 (1H, s)

(4) Ethyl 4-[1-[3-[[1-[N-(4-isobutylphenyl)carbamoyl]ethyl]amino]benzoyl]indolizin-3-yl]butyrate NMR (CDCl$_3$, δ): 0.88 (6H, d, J=7 Hz), 1.23 (3H, t, J=7 Hz), 1.62 (3H, d, J=7 Hz), 1.70 (1H, m), 1.9–2.1 (2H, m), 2.3–2.5 (4H, m), 2.80 (2H, t, J=7 Hz), 3.96 (1H, q, J=7 Hz), 4.12 (2H, q, J=7 Hz), 6.7–7. 0 (3H, m), 7.0–7.3 (4H, m), 7.4–7.5 (3H, m), 7.76 (1H, m), 8.03 (1H, d, J=7 Hz), 8.50 (1H, d, J=9 Hz), 8.83 (1H, s)

EXAMPLE 29

The following compound was obtained according to a similar manner to that of Example 1.

Ethyl 4-[1-[3-[(benzyloxycarbonyl)(4-isobutylphenyl)methyl]amino]benzoyl]indolizin-3-yl]butyrate NMR (CDCl$_3$, δ): 0.88 (6H, d, J=7 Hz), 1.25 (3H, t, J=7 Hz), 1.83 (1H, m), 1.9–2.1 (2H, m), 2.3–2.5 (4H, m), 2.85 (2H, t, J=7 Hz), 4.12 (2H, q, J=7 Hz), 5.14 (2H, s), 5.19 (1H, s), 6.7–7.0 (3H, m), 7.0–7.3 (11H, m), 7.38 (2H, d, J=9 Hz), 8.00 (1H, d, J=7 Hz), 8.46 (1H, d, J=9 Hz)

EXAMPLE 30

The following compounds were obtained according to similar manner to that of Example 9.

(1) 4-[1-[3-[[(Heptylcarbamoyl)(4-isobutylphenyl)methyl]amino]benzoyl]indolizin-3-yl]butyric acid NMR (CDCl$_3$, δ): 0.8–1.0 (9H, m), 1.1–1.3 (11H, m), 1.40 (2H, m), 1.85 (1H, m), 2.0–2.3 (2H, m), 2.4–2.6 (4H, m), 2.95 (2H, t, J=7 Hz), 3.22 (2H, m), 4.93 (1H, s), 6.8–7.5 (11H, m), 7.96 (1H, d, J=7 Hz), 8.54 (1H, d, J=9 Hz)

(2) 4-[1-[3-[[1-(Heptylcarbamoyl)ethyl]amino]benzoyl]indolizin-3-yl]butyric acid NMR (CDCl$_3$, δ): 0.8–1.0 (5H, m), 1.1–1.5 (6H, m), 1.56 (3H, d, J=7 Hz), 2.0–2.4 (4H, m), 2.47 (2H, t, J=7 Hz), 2.95 (2H, t, J=7 Hz), 3.17 (2H, m), 3.95 (1H, q, J=7 Hz), 6.8–7.1 (3H, m), 7.2–7.4 (4H, m), 7.96 (1H, d, J=7 Hz), 8.55 (1H, d, J=9 Hz)

(3) 4-[1-[3-[[1-[N-(4-Isobutylphenyl)carbamoyl]ethyl]amino]benzoyl]indolizin-3-yl]butyric acid NMR (CDCl$_3$, δ): 0.85 (6H, d, J=7 Hz), 1.62 (3H, d, J=7 Hz), 1.78 (1H, m), 1.9–2.2 (2H, m), 2.3–2.5 (4H, m), 2.83 (2H, t, J=7 Hz), 4.05 (1H, m), 6.83 (1H, s), 6.9–7.0 (2H, m), 7.05 (2H, d, J=9 Hz), 7.1–7.5 (6H, m), 7.95 (1H, d, J=7 Hz), 8.50 (1H, d, J=9 Hz), 8.95 (1H, s)

(4) 4-[1-[3-[[(Butylcarbamoyl)(4-isobutylphenyl)methyl]amino]benzoyl]indolizin-3-yl]butyric acid NMR (CDCl$_3$,δ): 0.80 (3H, t, J=7 Hz), 0.88 (6H, d, J=7 Hz), 1.1–1.5 (4H, m), 1.34 (1H, m), 2.12 (2H, m), 2.4–2.6 (4H, m), 2.96 (2H, t, J=7 Hz), 3.24 (2H, m), 4.99 (1H, s), 6.8–7.0 (3H, m), 7.0–7.4 (8H, m), 7.96 (1H, d, J=7 Hz), 8.53 (1H, d, J=9 Hz)

(5) 4-[1-[3-[[N-(4-Isobutylphenyl)carbamoylmethyl]amino]benzoyl]indolizin-3-yl]butyric acid NMR (CDCl$_3$, δ): 0.88 (6H, d, J=7 Hz), 1.80 (1H, m), 2.02 (2H, m), 2.3–2.5 (4H, m), 2.84 (2H, t, J=7 Hz), 3.94 (2H, s), 6.8–7.0 (3H, m), 7.08 (2H, t, J=7 Hz), 7.1–7.4 (4H, m), 7.40 (2H, d, J=9 Hz), 7.95 (1H, d, J=7 Hz), 8.50 (1H, d, J=9 Hz), 8.57 (1H, s)

EXAMPLE 31

The following compounds were obtained according to a similar manner to that of Example 24.

(1) 4-[1-[4-[(S)-1-(4-Isobutylphenyl)-2-ethoxyethoxy]benzoyl]indolizin-3-yl]butyric acid NMR (CDCl$_3$, δ): 0.88 (6H, d, J=7 Hz ), 1.22 (3H, t, J=7 Hz ), 1.7–2.15 (3H, m), 2.4–2.55 (4H, m), 2.88 (2H, t, J=7.5 Hz), 3.5–3.75 (3H, m), 3.8–3.95 (1H, m), 5.41 (1H, dd, J=4.5 Hz, 6 Hz), 6.8–6.9 (2H, m), 6.97 (2H, d, J=9 Hz), 7.05–7.2 (3H, m), 7.25–7.35 (2H, m), 7.72 (2H, d, J=9 Hz), 7.94 (1H, d, J=7 Hz), 7.42 (1H, d, J=9 Hz)

(2) 4-[1-[4-[(R)-1-(4-Isobutylphenyl)-2-ethoxyethoxy]benzoyl]indolizin-3-yl]butyric acid NMR (CDCl$_3$, δ): 0.88 (6H, d, J=7 Hz), 1.22 (3H, t, J=7 Hz), 1.7–2.15 (3H, m), 2.4–2.55 (4H, m), 2.88 (2H, t, J=7.5 Hz), 3.5–3.75 (3H, m), 3.8–3.95 (1H, m), 5.41 (1H, dd, J=4.5 Hz, 6 Hz), 6.8–6.9 (2H, m), 6.97 (2H, d, J=9 Hz), 7.05–7.2 (3H, m), 7.25–7.35 (2H, m), 7.73 (2H, d, J=9 Hz), 7.98 (1H, d, J=7 Hz), 8.43 (1H, d, J=9 Hz)

EXAMPLE 32

The following compounds were obtained according to a similar manner to that of Example 23.

(1) Ethyl 4-[1-[4-[(S)-1-(4-isobutylphenyl)-2-ethoxyethoxy]benzoyl]indolizin-3-yl]butyrate NMR (CDCl$_3$, δ): 0.89 (6H, d, J=7 Hz), 1.15–1.3 (6H, m), 1.7–2.15 (3H, m), 2.35–2.5 (4H, m), 2.88 (2H, t, J=7.5 Hz), 3.5–3.75 (3H, m), 3.8–3.95 (1H, m), 4.13 (2H, q, J=7 Hz), 5.41 (1H, dd, J=4.5 Hz, 6 Hz), 6.8–6.9 (2H, m), 6.97 (2H, d, J=9 Hz), 7.05–7.2 (3H, m), 7.25–7.35 (2H, m), 7.73 (2H, d, J=9 Hz), 7.98 (1H, d, J=7 Hz), 7.43 (1H, d, J=9 Hz)

(2) Ethyl 4-[1-[4-[(R)-1-(4-isobutylphenyl)-2-ethoxyethoxy]benzoyl]indolizin-3-yl]butyrate NMR (CDCl$_3$, δ): 0.89 (6H, d, J=7 Hz), 1.15–1.3 (6H, m), 1.7–2.15 (3H, m), 2.35–2.5 (4H, m), 2.88 (2H, t, J=7.5 Hz), 3.5–3.75 (3H, m), 3.8–3.95 (1H, m), 4.13 (2H, q, J=7 Hz), 5.41 (1H, dd, J=4.5 Hz, 6 Hz), 6.8–6.9 (2H, m), 6.97 (2H, d, J=9 Hz), 7.05–7.2 (3H, m), 7.25–7.35 (2H, m), 7.73 (2H, d, J=9 Hz), 7.98 (1H, d, J=7 Hz), 8.43 (1H, d, J=9 Hz)

EXAMPLE 33

The following compound was obtained according to a similar manner to that of Preparation 31.

Ethyl 4-[1-[3-[[(carboxy)(4-isobutylphenyl)methyl]amino] benzoyl]indolizin- 3-yl]butyrate NMR (CDCl$_3$, δ): 0.89 (6H, d, J=7 Hz), 1.23 (3H, t, J=7 Hz), 1.83 (1H, m), 1.9–2.2 (2H, m), 2.3–2.6 (4H, m), 2.82 (2H, t, J=7 Hz), 4.13 (2H, q, J=7 Hz), 5.08 (1H, s), 6.7–7.0 (3H, m), 7.0–7.4 (6H, m), 7.42 (2H, d, J=9 Hz), 7.96 d, J=7 Hz), 8.52 (1H, d, J=9 Hz)

EXAMPLE 34

The following compounds were obtained according to a similar manner to that of Example 23.

(1) Ethyl 4-[1-[4-[1-(4-isobutylphenyl)-2-butynyloxy]benzoyl]indolizin-3-yl]butyrate NMR (CDCl$_3$, δ): 0.92 (6H, d, J=7 Hz), 1.25 (3H, t, J=7 Hz), 1.75–2.2 (3H, m), 1.92 (3H, d, J=3 Hz), 2.4–2.55 (4H, m), 2.91 (2H, t, J=7 Hz), 4.14 (2H, q, J=7 Hz), 5.86 (1H, m), 6.88 (1H, dt, J=2 Hz, 7 Hz), 6.93 (1H, s), 7.1–7.3 (5H, m), 7.52 (2H, d, J=9 Hz), 7.85 (2H, d, J=10 Hz), 8.01 (1H, d, J=7 Hz), 8.48 (1H, d, J=8 Hz)

(2) Ethyl 4-[1-[4-[1-(4-isobutylphenyl)-3-butenyloxy]benzoyl]indolizin-3-yl]butyrate NMR (CDCl$_3$, δ): 0.88 (6H, d, J=7 Hz), 1.25 (3H, t, J=7 Hz), 1.84 (1H, m), 2.03 (2H, m), 2.35–2.5 (4H, m), 2.5–2.9 (2H, m), 2.87 (2H, t, J=7 Hz), 4.12 (2H, q, J=7 Hz), 5.05–5.3 (3H, m), 5.87 (1H, m), 6.8–6.97 (4H, m), 7.12 (2H, d, J=8 Hz), 7.14 (1H, m), 7.28 (2H, d, J=8 Hz), 7.74 (2H, d, J=9 Hz), 7.98 (1H, d, J=8 Hz), 8.43 (1H, d, J=10 Hz)

(3) Ethyl 4-[1-[4-[1-(4-isobutylphenyl)-4-pentenyloxy]benzoyl]indolizin- 3-yl]butyrat NMR (CDCl$_3$, δ): 0.88 (6H, d, J=7 Hz), 1.25 (3H, t, J=7 Hz), 1.7–2.35 (7H, m), 2.42 (2H, t, J=7 Hz), 2.46 (2H, d, J=7 Hz), 2.88 (2H, t, J=7 Hz), 4.13 (2H, q, J=7 Hz), 4.95–5.25 (3H, m), 5.87 (1H, m), 6.85 (1H, m), 6.87 (1H, s), 6.93 (2H, d, J=9 Hz), 7.12 (1H, d, J=8 Hz), 7.04 (1H, m), 7.28 (2H, d, J=8 Hz), 7.73 (2H, d, J=9 Hz), 7.98 (1H, d, J=8 Hz), 8.43 (1H, d, J=9 Hz)

(4) Ethyl 4-[1-[4-[(S)-1-(4-isobutylphenyl)-3-butenyloxy]benzoyl]indolizin-3-yl]butyrate NMR (CDCl$_3$, δ): 0.88 (6H, d, J=7 Hz), 1.25 (3H, t, J=7 Hz), 1.7–2.15 (3H, m), 2.43 (2H, t, J=7 Hz), 2.46 (2H, d, J=7 Hz), 2.5–2.9 (2H, m), 2.87 (2H, t, J=7 Hz), 4.12 (2H, q, J=7 Hz), 5.05–5.3 (3H, m), 5.87 (1H, m), 6.8–6.97 (4H, m), 7.12 (2H, d, J=8 Hz), 7.14 (1H, m), 7.28 (2H, d, J=8 Hz), 7.74 (2H, d, J=9 Hz), 7.98 (1H, d, J=8 Hz), 8.43 (1H, d, J=10 Hz)

(5) Ethyl 4-[1-[4-[4,4,4-trifluoro-1-(4-isobutylphenyl)-butoxy]benzoyl]indolizin-3-yl]butyrate NMR (CDCl$_3$, δ): 0.89 (6H, d, J=7 Hz), 1.25 (3H, t, J=7 Hz), 1.7–2.5 (11H, m), 2.88 (2H, t, J=7.5 Hz), 4.12 (2H, q, J=7 Hz), 5.24 (1H, t, J=5.5 Hz), 6.8–6.95(4H, m), 7.1–7.2 (3H, m), 7.27 (2H, d, J=8Hz), 7.73 (2H, d, J=9 Hz), 7.99 (1H, d, J=7 Hz), 8.44 (1H, d, J=9 Hz)

(6) Ethyl 4-[1-[4-[1-(4-isobutyl-2-methoxyphenyl)-pentyloxy]benzoyl]indolizin-3-yl]butyrate NMR (CDCl$_3$, δ): 0.8–1.0 (9H, m), 1.15–1.6 (7H, m), 1.7–2.2 (5H, m), 2.35–2.5 (4H, m), 2.87 (2H, t, J=7.5 Hz), 3.91 (3H, s), 4.13 (2H, q, J=7 Hz), 5.60 (1H, dd, J=5 Hz, 8 Hz), 6.6–7.0 (6H, m), 7.05–7.35 (2H, m), 7.72 (2H, d, J=9 Hz), 7.97 (1H, d, J=7 Hz), 8.43 (1H, d, J=9 Hz)

(7) Ethyl 4-[1-[4-[1-(4-isobutyl-3-methoxyphenyl)-pentyloxy]benzoyl]indolizin-3-yl]butyrate NMR (CDCl$_3$, δ): 0.8–1.0 (9H, m), 1.2–1.7 (7H, m), 1.75–2.15 (5H, m), 2.35–2.5 (4H, m), 2.88 (2H, t, J=7.5 Hz), 3.79 (3H, s), 4.13 (2H, q, J=7 Hz), 5.12 (1H, dd, J=5 Hz, 8 Hz), 6.8–7.2 (8H, m), 7.74 (2H, d, J=9 Hz), 7.98 (1H, d, J=7 Hz), 8.44 (1H, d, J=9 Hz)

(8) Ethyl 4-[1-[4-[1-(3-fluoro-4-isobutylphenyl)pentyloxy]benzoyl]indolizin-3-yl]butyrate NMR (CDCl$_3$, δ): 0.85–1.0 (9H, m), 1.2–1.6 (7H, m), 1.75–2.15 (5H, m), 2.35–2.5 (4H, m), 2.88 (2H, t, J=7.5 Hz), 4.13 (2H, q, J=7 Hz), 5.14 (1H, dd, J=5 Hz, 8 Hz), 6.8–7.2 (8H, m), 7.74 (2H, d, J=9 Hz), 7.98 (1H, d, J=7 Hz), 8.44 (1H, d, J=9 Hz)

(9) Ethyl 4-[1-[4-[1-[4-(1-acetoxy-2-methylpropyl)-2-fluorophenyl]pentyloxy]benzoyl]indolizin-3-yl]butyrate NMR (CDCl$_3$, δ) 0.75–1.0 (9H, m), 1.25 (3H, t, J=7 Hz), 1.3–1.6 (4H, m), 1.75–2.15 (8H, m), 2.42 (2H, t, J=7 Hz), 2.88 (2H, t, J=7.5 Hz), 4.12 (2H, q, J=7 Hz), 5.44 (1H, q, J=7 Hz), 5.52 (1H, dd, J=5 Hz, 8 Hz), 6.8–7.2 (7H, m), 7.3–7.4 (1H, m), 7.75 (2H, d, J=9 Hz), 7.98 (1H, d, J=7 Hz), 8.44 (1H, d, J=9 Hz)

(10) Ethyl 4-[1-[4-[1-[4-(cyclopropylmethyl)phenyl]-3-butenyloxy]benzoyl]indolizin-3-yl]butyrate NMR (CDCl$_3$, δ): 0.45–0.6 (2H, m), 0.85–1.1 (1H, m), 1.25 (3H, t, J=7 Hz), 1.95–2.15 (2H, m), 2.35–2.95 (8H, m), 4.12 (2H, q, J=7 Hz), 5.05–5.3 (3H, m), 5.75–6.0 (1H, m), 6.8–7.0 (4H, m), 7.05–7.35 (5H, m), 7.73 (2H, d, J=9 Hz), 7.98 (1H, d, J=7 Hz), 8.44 (1H, d, J=9 Hz)

EXAMPLE 35

The following compound was obtained according to a similar manner to that of Example 1.

Ethyl 4-[1-[3-[(4-isobutylphenyl)(phenyl)methylamino]benzoyl]indolizin-3-yl]butyrate NMR (CDCl$_3$, δ): 0.88 (6H, d, J=7 Hz), 1.25 (3H, t, J=7 Hz), 1.7–2.1 (3H, m), 2.3–2.5 (4H, m), 2.82 (2H, t, J=7.5 Hz), 4.12 (2H, q, J=7 Hz), 4.40 (1H, br s), 5.55 (1H, s), 6.6–6.95 (3H, m), 7.0–7.45 (13H, m), 7.99 (1H, d, J=7 Hz), 8.48 (1H, d, J=9 Hz)

EXAMPLE 36

To a solution of ethyl 4-(3-indolizinyl)butyrate (0.20 g) and 3-trans-[2-(4-isobutylphenyl)vinyl]benzoyl chloride (0.40 g) in dichloroethane (6 ml) was added diisopropylethylamine (0.23 g). The mixture was refluxed for 8 hours, poured into ice and diluted hydrochloric acid and extracted with ethyl acetate (30 ml). The organic layer was washed with water, dried over magnesium sulfate and evaporated. The residue was chromatographed on silica gel eluting with a mixture of n-hexane and ethyl acetate (3:1) to give ethyl 4-[1-[3-trans-[2-(4-isobutylphenyl)vinyl]benzoyl]indolizin-3-yl]butyrate (0.29 g) as a yellow oil.

NMR (CDCl$_3$, δ): 0.91 (6H, d, J=7 Hz), 1.24 (3H, t, J=7 Hz), 1.88 (1H, m), 2.05 (2H, m), 2.45 (2H, t, J=7 Hz), 2.50 (2H, d, J=7 Hz), 2.90 (2H, t, J=7 Hz), 4.13 (2H, q, J=7 Hz), 6.90 (1H, s), 7.14 (2H, d, J=8 Hz), 7.16 (2H, s), 7.23 (1H, m), 7.45 (2H, d, J=8 Hz), 7.5 (1H, m), 7.65 (2H, m), 7.95 (1H, s), 8.04 (1H, d, J=7 Hz), 8.52 (1H, d, J=9 Hz)

EXAMPLE 37

The following compounds were obtained according to similar manner to that of Example 36.

(1) Ethyl 4-[1-[4-trans-[2-(4-isobutylphenyl)vinyl]-benzoyl]indolizin-3-yl]butyrate mp: 94°–95° C.

NMR (CDCl$_3$, δ): 0.92 (6H, d, J=7 Hz), 1.36 (3H, t, J=7 Hz), 1.88 (1H, m), 2.0–2.2 (2H, 2.4–2.6 (4H, m), 2.90 (2H, t, J=7 Hz), 4.13 (2H, q, J=7 Hz), 6.8–7.0 (2H, m), 7.1–7.3 (5H, m), 7.47 (2H, d, J=9 Hz), 7.62 (2H, d, J=9 Hz), 7.85 (2H, d, J=9 Hz), 8.02 (1H, d, J=7 Hz), 8.51 (1H, d, J=9 Hz)

(2) Ethyl 4-[1-[4-cis-[2-(4-isobutylphenyl)vinyl]benzoyl]indolizin-3-yl]butyrate NMR (CDCl$_3$, δ): 0.90 (6H, d, J=7 Hz), 1.25 (3H, t, J=7 Hz), 1.85 (1H, m), 2.0–2.2 (2H, m), 2.4–2.5 (4H, m), 2.89 (2H, t, J=7 Hz), 4.13 (2H, q, J=7 Hz), 6.60 (1H, d, J=11Hz), 6.68 (1H, d, J=11 Hz), 6.85–7.0 (2H, m), 7.02 (2H, d, J=9 Hz), 7.15–7.3 (3H, m), 7.39 (2H, d, J=9 Hz), 7.71 (2H, d, J=9 Hz), 8.02 (1H, d, J=7 Hz), 8.50 (1H, d, J=9 Hz)

(3) Ethyl 4-[1-[3-cis-[2-(4-isobutylphenyl)vinyl]benzoyl]indolizin-3-yl]butyrate NMR (CDCl$_3$, δ): 0.85 (6H, d, J=7 Hz), 1.28 (3H, t, J=7 Hz), 1.80 (1H, m), 2.05 (2H, m), 2.40 d, J=7 Hz), 2.42 (2H, t, J=7 Hz), 2.85 (2H, t, J=7 Hz), 4.13 (2H, q, J=7 Hz), 6.62 (2H, s), 6.79 (1H, s), 6.89 (1H, t, J=7 Hz), 7.00 (2H, d, J=8 Hz), 7.18 (2H, d, J=8 Hz), 7.1–7.2 (1H, m), 7.3–7.5 (2H, m), 7.65 (1H, d, J=8 Hz), 7.71 (1H, s), 8.02 (1H, d, J=7 Hz), 8.48 (1H, d, J=9 Hz)

EXAMPLE 38

The following compounds were obtained according to a similar manner to that of Example 9.

(1) 4-[1-[4-[1-(4-Isobutylphenyl)-2-butynyloxy]benzoyl]-indolizin-3-yl]butyric acid NMR (CDCl$_3$, δ): 0.92 (6H, d, J=7 Hz), 1.87 (1H, m), 1.90 (3H, d, J=3 Hz), 2.08 (2H, m), 2.49 (2H, d, J=7 Hz), 2.50 (2H, t, J=7 Hz), 2.91 (2H, t, J=7 Hz), 5.86 (1H, m), 6.87 (1H, dt, J=2 Hz, 7 Hz), 6.92 (1H, s), 7.1–7.25 (5H, m), 7.52 (2H, d, J=9 Hz), 7.84 (2H, d, J=10 Hz), 7.97 (1H, d, J=7 Hz), 8.46 (1H, d, J=8 Hz)

(2) 4-[1-[4-[1-(4-Isobutylphenyl)-3-butenyloxy]benzoyl]-indolizin-3-yl]butyric acid NMR (CDCl$_3$, δ): 0.88 (6H, d, J=7 Hz), 1.84 (1H, m), 2.05 (2H, m), 2.44 (2H, d, J=7 Hz), 2.48 (2H, t, J=7 Hz), 2.5–2.9 (2H, m), 2.88 (2H, t, J=7 Hz), 5.03–5.27 (3H, m), 5.87 (1H, m), 6.84 (1H, m), 6.87 (1H, s), 6.92 (2H, d, J=10 Hz), 7.11 (2H, d, J=8Hz), 7.13 (1H, m), 7.27 (2H, d, J=8 Hz), 7.72 (2H, d, J=10 Hz), 7.94 (1H, d, J=7 Hz), 8.42 (1H, d, J=9 Hz)

(3) 4-[1-[4-[1-(4-Isobutylphenyl) -4-pentenyloxy]benzoyl]-indolizin-3-yl]butyric acid NMR (CDCl$_3$, δ): 0.88 (6H, d, J=7 Hz), 1.7–2.35 (7H, m), 2.43 (2H, d, J=7 Hz), 2.49 (2H, t, J=7 Hz), 2.89 (2H, t, J=7 Hz), 4.95–5.1 (2H, m), 5.18 (1H, m), 5.86 (1H, m), 6.84 (1H, m), 6.88 (1H, s), 6.92 (2H, d, J=9 Hz), 7.11 (2H, d, J=8 Hz), 7.13 (1H, m), 7.27 (2H, d, J=8 Hz), 7.73 (2H, d, J=9 Hz), 7.94 (1H, d, J=7 Hz), 8.43 (1H, d, J=9 Hz)

(4) 4-[1-[4-[(S)-i-(4-Isobutylphenyl)-3-butenyloxy]-benzoyl]indolizin-3-yl]butyric acid NMR (CDCl$_3$, δ): 0.88 (6H, d, J=7 Hz), 1.84 (1H, m), 2.05 (2H, m), 2.44 (2H, d, J=7 Hz), 2.48 (2H, t, J=7 Hz), 2.5–2.9 (2H, m), 2.88 (2H, t, J=7 Hz), 5.03–5.27 (3H, m), 5.87 (1H, m), 6.84 (1H, m), 6.87 (1H, s), 6.92 (2H, d, J=10 Hz), 7.11 (2H, d, J=8Hz), 7.13 (1H, m), 7.27 (2H, d, J=8 Hz), 7.72 (2H, d, J=10 Hz), 7.94 (1H, d, J=7 Hz), 8.42 (1H, d, J=9 Hz)

EXAMPLE 39

The following compounds were obtained according to a similar manner to that of Example 11.

(1) 4-[1-[4-[4,4,4-Trifluoro-1-(4-isobutylphenyl)-butoxy]benzoyl]indolizin-3-yl]butyric acid NMR (CDCl$_3$, δ): 0.88 (6H, d, J=7 Hz), 1.7–2.55 (11H, m), 2.39 (2H, t, J=7.5 Hz), 5.25 (1H, t, J=5.5 Hz), 6.8–7.0 (4H, m), 7.1–7.2 (3H, m), 7.27 (2H, d, J=8 Hz), 7.75 (2H, d, J=9 Hz), 8.97 (1H, d, J=7 Hz), 8.46 (1H, d, J=9 Hz)

(2) 4-[1-[3-[(4-Isobutylphenyl)(phenyl)methylamino]-benzoyl]indolizin-3-yl]butyric acid NMR (CDCl$_3$, δ): 0.88 (6H, d, J=7 Hz), 1.7–2.1 (3H, m), 2.35–2.55 (4H, m), 2.85 (2H, t, J=7.5 Hz), 5.55 (1H, s), 6.6–6.9 (3H, m), 6.95–7.45 (13H, m), 7.95 (1H, d, J=7 Hz), 8.47 (1H, d, J=9 Hz)

(3) 4-[1-[4-[1-(4-Isobutyl-2-methoxyphenyl)pentyloxy]benzoyl]indolizin-3-yl]butyric acid NMR (CDCl$_3$, δ): 0.8–1.0 (9H, m), 1.2–1.65 (4H, m), 1.7–2.2 (5H, m), 2.4–2.55 (4H, m), 2.89 (2H, t, J=7.5 Hz), 3.90 (3H, s), 5.59 (1H, dd, J=5 Hz, 8 Hz), 6.78 (2H, d, J=7 Hz), 6.8–6.95 (4H, m), 7.05–7.3 (2H, m), 7.72 (2H, d, J=9 Hz), 7.94 (1H, d, J=7 Hz), 8.42 (1H, d, J=9 Hz)

(4) 4-[1-[4-[1-(4-Isobutyl-3-methoxyphenyl)pentyloxy]benzoyl]indolizin-3-yl]butyric acid NMR (CDCl$_3$, δ): 0.8–1.0 (9H, m), 1.25–1.6 (4H, 1.75–2.15 (5H, m), 2.4–2.55 (4H, m), 2.89 (2H, t, J=7.5 Hz), 3.78 (3H, s ), 5.12 (1H, dd, J=5 Hz, 8 Hz), 6.75–7.2 (8H, m), 7.73 (2H, d, J=9 Hz), 7.95 (1H, d, J=7 Hz), 8.43 (1H, d, J=9 Hz)

(5) 4-[1-[4-[1-(3-Fluoro-4-isobutylphenyl)pentyloxy]-benzoyl]indolizin-3-yl]butyric acid NMR (CDCl$_3$, δ): 0.8–1.0 (9H, m), 1.2–1.6 (4H, m), 1.75–2.15 (5H, m), 2.4–2.55 (4H, m), 2.88 (2H, t, J=7.5 Hz), 5.13 (1H, dd, J=5 Hz, 8 Hz), 6.8–7.2 (8H, m), 7.74 (2H, d, J=9 Hz), 7.95 (1H, d, J=7 Hz), 8.44 (1H, d, J=9 Hz)

(6) 4-[1-[4-[1-[4-(Cyclopropylmethyl)phenyl]-3-butenyloxy]benzoyl]indolizin-3-yl]butyric acid NMR (CDCl$_3$, δ): 0.45–0.6 (2H, m), 0.85–1.1 (1H, m), 1.95–2.15 (2H, m), 2.4–3.0 (8H, m), 5.0–5.3 (3H, m), 5.75–6.0 (1H, m), 6.8–7.0 (4H, m), 7.05–7.4 (5H, m), 7.72 (2H, d, J=9 Hz), 7.95 (1H, d, J=7 Hz), 8.43 (1H, d, J=9 Hz)

EXAMPLE 40

To a solution of ethyl 4-[1-[3-trans-[2-(4-isobutyl-phenyl)vinyl]benzoyl]indolizin-3-yl]butyrate (0.24 g) in dioxane (5 ml) was added 1N-sodium hydroxide aqueous solution (1 ml). The mixture was stirred for 4 hours at 40° C. and poured into ice and diluted hydrochloric acid. The organic layer was extracted with ethyl acetate (15 ml), washed with water, dried over magnesium sulfate and evaporated. The residue was chromatographed on silica gel (20 g) eluting with a mixture of chloroform and methanol (50:1) to give 4-[1-[3-trans-[2-(4-isobutylphenyl)vinyl]benzoyl]indolizin-3-yl]butyric acid (0.20 g) as yellow powder.

NMR (CDCl$_3$, δ): 0.90 (6H, d, J=7 Hz), 1.85 (1H, m), 2.0–2.2 (2H, m), 2.4–2.6 (4H, m), 2.90 (2H, t, J=7 Hz), 6.8–7.0 (2H, m), 7.1–7.3 (5H, m), 7.4–7.5 (3H, m), 7.6–7.7 (2H, m), 7.93 (1H, s), 7.99 (1H, d, J=7 Hz), 8.51 (1H, d, J=9 Hz)

EXAMPLE 41

The following compounds were obtained according to a similar manner to that of Example 40.

(1) 4-[1-[4-trans-[2-(4-Isobutylphenyl)vinyl]benzoyl]indolizinyl-3-yl]butyric acid mp: 175°–176° C.

NMR (CDCl$_3$, δ): 0.92 (6H, d, J=7 Hz), 1.90 (1H, m), 2.0–2.2 (2H, m), 2.4–2.6 (4H, m), 2.90 (2H, t, J=7 Hz), 6.8–7.0 (2H, m), 7.0–7.2 (5H, m), 7.47 (2H, d, J=9 Hz), 7.60 (2H, d, J=9 Hz), 7.82 (2H, d, J=9 Hz), 7.97 (1H, d, J=7 Hz), 8.51 (1H, d, J=9 Hz)

(2) 4-[1-[4-cis-[2-(4-Isobutylphenyl)vinyl]benzoyl]indolizin-3-yl]butyric acid

NMR (CDCl$_3$, δ): 0.88 (6H, d, J=7 Hz), 1.83 (1H, m), 2.0–2.2 (2H, m), 2.4–2.6 (4H, m), 2.92 (2H, t, J=7 Hz), 6.58 (1H, d, J=11Hz), 6.68 (1H, d, J=11 Hz), 6.85–6.95 (2H, m), 7.00 (2H, d, J=9 Hz), 7.1–7.2 (1H, m), 7.20 (2H, d, J=9 Hz), 7.38 (2H, d, J=9 Hz), 7.70 (2H, d, J=9 Hz), 7.98 (1H, d, J=7 Hz), 8.49 (1H, d, J=9 Hz)

(3) 4-[1-[3-cis-[2-(4-Isobutylphenyl)vinyl]benzoyl]indolizin-3-yl]butyric acid

NMR (CDCl$_3$, δ): 0.83 (6H, d, J=7 Hz), 1.80 (1H, m), 1.9–2.15 (2H, m), 2.40 (2H, d, J=7 Hz), 2.46 (2H, t, J=7 Hz), 2.87 (2H, t, J=7 Hz), 6.62 (2H, s), 6.79 (1H, s), 6.88 (1H, t, J=7 Hz), 7.00 (2H, d, J=9 Hz), 7.1–7.3 (3H, m), 7.3–7.5 (2H, m), 7.65 (1H, d, J=7 Hz), 7.70 (1H, s), 7.96 (1H, d, J=7 Hz), 8.48 (1H, d, J=9 Hz)

EXAMPLE 42

To a solution of ethyl 4-[1-[4-[1-[4-(1-acetoxy-2-methylpropyl)-2-fluorophenyl]pentyloxy]benzoyl]indolizin-yl]butyrate (300 mg) in ethanol (3 ml) and 1,4-dioxane (3 ml) was added 1N aqueous solution of sodium hydroxide (1.5 ml). The mixture was stirred at room temperature for 1 hour, and then poured into a mixture of ethyl acetate and 0.5N hydrochloric acid. The organic layer was separated, washed with water and brine, dried over magnesium sulfate and concentrated. The residue was chromatographed on silica gel column eluting with a mixture of chloroform and methanol (25:1) to give 4-[1-[4-[1-[2-fluoro-4-(1-hydroxyl-2-methylpropyl)phenyl]-pentyloxy]benzoyl]indolizin-3-yl]butyric acid (151 mg) as powder.

NMR (CDCl$_3$, δ): 0.75–1.05 (9H, m), 1.2–1.65 (4H, m), 1.75–2.15 (5H, m), 2.45 (2H, t, J=7 Hz), 2.84 (2H, t, J=7 Hz), 4.35 (1H, d, J=6.5 Hz), 5.53 (1H, dd, J=5 Hz, 7.5 Hz), 6.75–7.2 (7H, m), 7.25–7.4 (1H, m), 7.70 (2H, d, J=9 Hz), 7.91 (1H, d, J=7 Hz), 8.42 (1H, d, J=9 Hz)

EXAMPLE 43

The following compounds were obtained according to a similar manner to that of Example 36.

(10) Ethyl 4-[1-[4-[1-(4-isobutylphenyl)butyloxy]benzoyl]indolizin-3-yl]butyrate NMR (CDCl$_3$, δ): 0.8–1.05 (9H, m), 1.24 (3H, t, J=7 Hz), 1.3–1.65 (2H, m), 1.7–2.15 (5H, m), 2.35–2.5 (4H, m), 2.87 (2H, t, J=7.5 Hz), 4.12 (2H, q, J=7 Hz), 5.17 (1H, dd, J=2 Hz, 7 Hz), 6.8–6.95 (4H, m), 7.05–7.3 (5H, m), 7.72 (2H, d, J=9 Hz), 7.98 (1H, d, J=7 Hz), 8.44 (1H, d, J=9 Hz)

(2) Ethyl 4-[1-[4-[(S)-i-(4-isobutylphenyl)butoxy]benzoyl]indolizin-3-yl]butyrate NMR (CDCl$_3$, δ): 0.8–1.05 (9H, m), 1.24 (3H, t, J=7 Hz), 1.3–1.65 (2H, m), 1.7–2.15 (5H, m), 2.35–2.5 (4H, m), 2.87 (2H, t, J=7.5 Hz), 4.12 (2H, q, J=7 Hz), 5.17 (1H, dd, J=2 Hz, 7 Hz), 6.8–6.95 (4H, m), 7.05–7.3 (5H, m), 7.72 (2H, d, J=9 Hz), 7.98 (1H, d, J=7 Hz), 8.44 (1H, d, J=9 Hz)

What we claim is:

1. A compound of the formula:

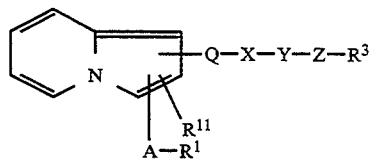

wherein $R^1$ is carboxy or pharmaceutically acceptable protected carboxy, $R^3$ is phenyl substituted by lower alkyl, mono- or di- or triphenyl(lower)alkyl which may be substituted by one to four substituents selected from the group consisting of lower alkyl, halogen, cyano, carboxy, mono- or di- or triphenyl(lower)alkoxycarbonyl, mono- or di(lower)alkylcarbamoyl, phenylcarbamoyl, lower alkylphenylcarbamoyl, lower alkoxy, hydroxy(lower)alkyl, lower alkanoyloxy(lower)alkyl, cyclo(lower)alkyl(lower)alkyl, lower alkenyl and lower alkynyl, lower alkylcarbamoyl(lower)alkyl, or lower alkylphenylcarbamoyl(lower)alkyl, $R^{11}$ is hydrogen or lower alkyl, A is lower alkylene which may be substituted by oxo, or lower alkenylene, Q is carbonyl or lower alkylene,

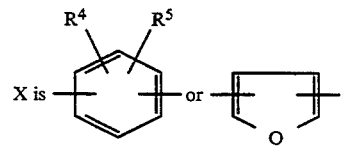

in which $R^4$ is hydrogen or lower alkyl, and $R^5$ is hydrogen, lower alkyl or Y—Z—$R^3$, Y is bond or lower alkylene, Z is lower alkylene, lower alkenylene,

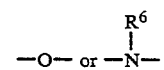

in which $R^6$ is hydrogen, lower alkyl, mono- or di- or triphenyl(lower)alkyl which may be substituted by lower alkyl, or lower alkoxycarbonyl, and pharmaceutically acceptable salts thereof.

2. A compound of claim 1, which is represented by the formula:

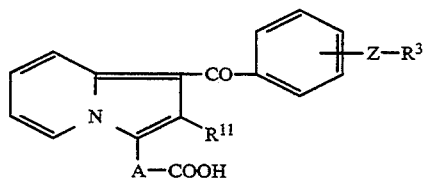

wherein $R^3$ is phenyl substituted by lower alkyl, mono- or diphenyl(lower)alkyl which may be substituted by one to four substituents selected from the group consisting of lower alkyl, halogen, cyano, carboxy, phenyl(lower)alkoxycarbonyl, mono- or di(lower-)alkylcarbamoyl, phenylcarbamoyl lower alkylphenylcarbamoyl, lower alkoxy, hydroxy(lower-)alkyl, lower alkanoyloxy(lower)alkyl, cyclo(-lower)alkyl(lower)alkyl, lower alkenyl and lower alkynyl, lower alkylcarbamoyl(lower)alkyl, lower alkylphenylcarbamoyl(lower)alkyl, $R^{11}$ is hydrogen or lower alkyl, A is lower alkylene, and Z is lower alkylene, lower alkenylene,

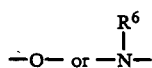

in which $R^6$ is hydrogen, lower alkyl or phenyl(lower)alkyl.

3. A compound of claim 2, wherein $R^3$ is isobutylphenyl, isobutylphenylpropyl, isobutylpenylbutyl, isobutylphenylpentyl, isobutylphenylhexyl, isobutylphenylheptyl, isobutylphenyloctyl, bis(isobutylphenyl)methyl, (carboxy)(isobutylphenyl)methyl, (benzyloxycarbonyl)(isobutylphenyl)methyl, (butylcarbamoyl)(isobutylphenyl)methyl, (heptylcarbamoyl)(isobutylphenyl)methyl, (ethoxy)(isobutylphenyl)ethyl, (isobutylphenyl)(trifluoro)butyl, (phenyl)(isobutylphenyl)methyl, [(isobutyl)(methoxy)phenyl]pentyl, [(fluoro)-(isobutyl)phenyl]pentyl, [(fluoro)(hydroxyisobutyl)phenyl]pentyl, [(fluoro)(acetoxyisobutyl)phenyl]pentyl, (cyclopropylmethylphenyl)butenyl, (isobutylphenyl)butynyl, (isobutylphenyl)butenyl, (isobutylphenyl)pentenyl, heptylcarbamoylethyl, isobutylphenylcarbamoylmethyl or isobutylphenylcarbamoylethyl, $R^{11}$ is hydrogen or methyl, A is trimethylene, and Z is vinylene, —O— or —NH—.

4. A compound of claim 3, which is selected from the group consisting of:

4-[1-[4-[bis(4-isobutylphenyl)methylamino]benzoyl]-indolizin-3-yl]butyric acid,

4-[1-[4-1-(4-isobutylphenyl)propyloxy]benzoyl]-indolizin-3-yl]butyric acid,

4-[1-[4-1-(4-isobutylphenyl)butyloxy]benzoyl]-indolizin-3-yl]butyric acid, and

4-[1-[4-[1-(4-isobutylphenyl)pentyloxy]benzoyl]-indolizin-3-yl-]butyric acid.

5. A compound of claim 4, which is R or S configuration of the compound selected from the group consisting of:

4-[1-[4-[1-(4-isobutylphenyl)propyloxy]benzoyl]-indolizin-3-yl]butyric acid,

4-[1-[4-[1-(4-isobutylphenyl)butyloxy]benzoyl]-indolizin-3-yl]butyric acid, and

4-[1[4-[1-(4-isobutylphenyl)pentyloxy]benzoyl]-indolizin-3-yl]butyric acid.

6. A compound of claim 4, which is the S configuration of 4-[1-[4-[1-(4-isobutylphenyl)butyloxy]benzolyl]-indolizin-3-yl]butyric acid.

7. A compound of claim 1, which is represented by the formula:

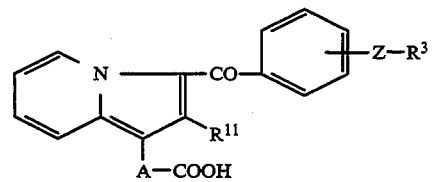

wherein $R^3$ is mono- or diphenyl(lower)alkyl which may be substituted by one or two substituents selected from lower alkyl, halogen, cyano, carboxy, phenyl(lower)alkoxycarbonyl, mono- or di(lower)alkylcarbamoyl, phenylcarbamoyl and lower alkylphenylcarbamoyl, $R^{11}$ is hydrogen or lower alkyl, A is lower alkylene, and Z is lower alkylene,

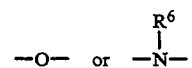

in which $R^6$ is hydrogen, lower alkyl or phenyl(lower)alkyl.

8. A compound of claim 7, wherein $R^3$ is isobutylphenylhexyl or bis(isobutylphenyl)methyl, $R^{11}$ is hydrogen or methyl, A is trimethylene, and Z is —O— or —NH—.

9. A compound of claim 8, which is selected from the group consisting of:

4-[3-[3-[bis(4-isobutylphenyl)methylamino]benzoyl]-indolizin-1-yl]butyric acid, and 4-[3-[3-[bis(4-isobutylphenyl)methoxy]benzoyl]-indolizin-1-yl]butyric acid.

10. A compound of the formula:

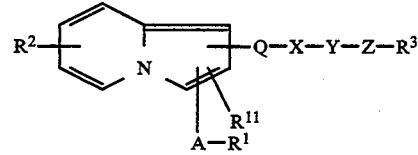

wherein $R^1$ is carboxy or pharmaceutically acceptable protected carboxy, $R^2$ is hydrogen, lower alkyl or halogen, $R^3$ is aryl or ar(lower)alkyl, each of which may have suitable substituent(s) selected from the group consisting of lower alkyl, halogen, cyano, carboxy, pharmaceutically acceptable esterified carboxy, pharmaceutically acceptable amidated carboxy, lower alkoxy, hydroxy(lower)alkyl, pharmaceutically acceptable protected hydroxy(lower)alkyl, cyclo(lower)alkyl(lower)alkyl, lower alkenyl and lower alkynyl, carbamoyl (lower)alkyl, in which the carbamoyl moiety is substituted by suitable substituents, selected from the group consisting of lower alkyl and lower alkylaryl, $R^{11}$ is hydrogen or lower alkyl, A is lower alkylene which may be substituted by oxo, or lower alkenylene, Q is carbonyl or lower alkylene, X is 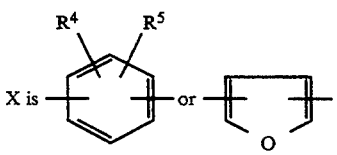

in which
R⁴ is hydrogen or lower alkyl, and
R⁵ is hydrogen, lower alkyl or Y—Z—R³,
Y is bond or lower alkylene,
Z is lower alkylene, lower alkenylene,

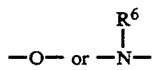

in which R⁶ is hydrogen, lower alkyl, ar(lower)alkyl which may have suitable substituent(s) selected from the group consisting of lower alkyl, halogen, cyano, carboxy, pharmaceutically acceptable esterified carboxy, pharmaceutically acceptable amidated carboxy, lower alkoxy, hydroxy(lower)alkyl, pharmaceutically acceptable protected hydroxy(lower)alkyl, cyclo(lower)alkyl-(lower)alkyl, lower alkenyl and lower alkynyl, or a pharmaceutically acceptable amino protective group, and pharmaceutically acceptable salts thereof.

11. A pharmaceutical composition comprising a compound of claim 10 or pharmaceutically acceptable salt thereof in association with a pharmaceutically acceptable, substantially non-toxic carrier or excipient.

12. A method for treating or preventing testosteron 5α-reductase-mediated diseases, which comprises administering a compound of claim 10 or pharmaceutically acceptable salt thereof to human beings or animals.

* * * * *